(12) United States Patent
Steyaert et al.

(10) Patent No.: US 10,054,598 B2
(45) Date of Patent: Aug. 21, 2018

(54) PROTEIN BINDING DOMAINS STABILIZING FUNCTIONAL CONFORMATIONAL STATES OF GPCRS AND USES THEREOF

(71) Applicants: VIB VZW, Ghent (BE); Vrije Universiteit Brussel, Brussels (BE); The Board of Trustees of the Leland Stanford Junior University, Palo Alto, CA (US)

(72) Inventors: Jan Steyaert, Beersel (BE); Els Pardon, Wezemaal (BE); Soren G. F. Rasmussen, Frederiksberg (DK); Juan Jose Fung, San Jose, CA (US); Brian Kobilka, Palo Alto, CA (US); Toon Laeremans, Dworp (BE)

(73) Assignees: VIB VZW, Gent (BE); VRIJE UNIVERSITEIT BRUSSEL, Brussels (BE); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 15/819,500

(22) Filed: Nov. 21, 2017

(65) Prior Publication Data
US 2018/0100865 A1 Apr. 12, 2018

Related U.S. Application Data

(63) Continuation of application No. 15/409,285, filed on Jan. 18, 2017, now Pat. No. 9,863,959, which is a continuation of application No. 15/236,398, filed on Aug. 13, 2016, now Pat. No. 9,689,872, which is a continuation of application No. 13/810,652, filed as application No. PCT/EP2011/062287 on Jul. 18, 2011, now Pat. No. 9,453,065.

(60) Provisional application No. 61/399,781, filed on Jul. 16, 2010.

(30) Foreign Application Priority Data

Sep. 6, 2010 (GB) .................................. 1014715.5

(51) Int. Cl.
*C07K 16/28* (2006.01)
*C07K 14/72* (2006.01)
*G01N 33/68* (2006.01)
*G01N 23/20* (2018.01)

(52) U.S. Cl.
CPC ....... *G01N 33/6872* (2013.01); *C07K 14/723* (2013.01); *C07K 16/28* (2013.01); *G01N 23/20* (2013.01); *G01N 33/6857* (2013.01); *C07K 2317/22* (2013.01); *C07K 2317/51* (2013.01); *C07K 2317/56* (2013.01); *C07K 2317/569* (2013.01); *G01N 2333/726* (2013.01)

(58) Field of Classification Search
CPC .................. C07K 14/723; C07K 16/28; C07K 2317/569; C07K 2317/22
See application file for complete search history.

(56) References Cited

U.S. PATENT DOCUMENTS

| 7,947,807 B2 | 5/2011 | Kobilka et al. |
|---|---|---|
| 9,453,065 B2 | 9/2016 | Steyaert et al. |
| 9,689,872 B2 | 6/2017 | Steyaert et al. |
| 2002/0192711 A1 | 12/2002 | Nestor et al. |
| 2003/0096297 A1 | 5/2003 | Gilchrist et al. |
| 2003/0129649 A1 | 7/2003 | Kobilka et al. |
| 2004/0018558 A1 | 1/2004 | Gilchrist et al. |
| 2004/0157268 A1 | 8/2004 | Kobilka et al. |
| 2007/0077597 A1 | 4/2007 | Gilchrist et al. |
| 2007/0231830 A1 | 10/2007 | Gilchrist et al. |
| 2008/0280308 A1 | 11/2008 | Gilchrist et al. |
| 2009/0298162 A1 | 12/2009 | Bouvier et al. |

(Continued)

FOREIGN PATENT DOCUMENTS

| GB | 2447786 | 9/2008 |
|---|---|---|
| WO | 9937681 | 7/1999 |

(Continued)

OTHER PUBLICATIONS

Burg et al., Structural basis for chemokine recognition and activation of a viral G protein-coupled receptor, Science, Mar. 6, 2015, pp. 1113-1117, vol. 347 issue 6226.

Ghosh et al., Methodological advances: the unsung heroes of the GPCR structural revolution, Nature Reviews Molecular Cell Biology, Jan. 15, 2014, pp. 1-13, advanced online publication, Macmillan Publishers Limited.

Gupta et al., Confirmation State-sensitive Antibodies to G-protein-coupled Receptors, Journal of Biological Chemistry, Feb. 23, 2007, pp. 5116-5124, vol. 282, No. 8.

(Continued)

*Primary Examiner* — Ruixiang Li
(74) *Attorney, Agent, or Firm* — TraskBritt, P.C.

(57) ABSTRACT

The present invention relates to the field of GPCR structure biology and signaling. In particular, the present invention relates to protein binding domains directed against or capable of specifically binding to a functional conformational state of a G-protein-coupled receptor (GPCR). More specifically, the present invention provides protein binding domains that are capable of increasing the stability of a functional conformational state of a GPCR, in particular, increasing the stability of a GPCR in its active conformational state. The protein binding domains of the present invention can be used as a tool for the structural and functional characterization of G-protein-coupled receptors bound to various natural and synthetic ligands, as well as for screening and drug discovery efforts targeting GPCRs. Moreover, the invention also encompasses the diagnostic, prognostic and therapeutic usefulness of these protein binding domains for GPCR-related diseases.

4 Claims, 27 Drawing Sheets
(25 of 27 Drawing Sheet(s) Filed in Color)

(56) References Cited

U.S. PATENT DOCUMENTS

| | | | |
|---|---|---|---|
| 2010/0062004 A1 | 3/2010 | Adams | |
| 2010/0190188 A1 | 7/2010 | Henderson et al. | |
| 2017/0153245 A1 | 6/2017 | Steyaert et al. | |

FOREIGN PATENT DOCUMENTS

| | | |
|---|---|---|
| WO | 0043507 | 7/2000 |
| WO | 0190190 | 11/2001 |
| WO | 02072778 | 9/2002 |
| WO | 02086507 | 10/2002 |
| WO | 03025020 | 3/2003 |
| WO | 03035694 A2 | 5/2003 |
| WO | 2004035614 | 4/2004 |
| WO | 2004092199 | 10/2004 |
| WO | 2006086883 | 8/2006 |
| WO | 2007042289 | 4/2007 |
| WO | 2009051633 | 4/2009 |
| WO | 2009081136 | 7/2009 |
| WO | 2010043650 | 4/2010 |
| WO | 2010066740 | 6/2010 |
| WO | 2012007593 | 1/2012 |
| WO | 2012007594 | 1/2012 |
| WO | 2014122183 A1 | 8/2014 |
| WO | 2015121092 A1 | 8/2015 |

OTHER PUBLICATIONS

Manglik et al., Structural insights into the Dynamic Process of B2-Adrenergic Receptor Signaling, Cell, May 21, 2015, pp. 1101-1111, vol. 161, Elseveir Inc.

Notice of Rejection dated Sep. 8, 2015, JP2013-520116.

Nygaard et al, The Dynamic Process of B2-Adrenergic Receptor Activation, Cell, Jan. 31, 2013, pp. 532-542, vol. 152, Elseveir Inc.

Pardon et al., A general protocol for the generation of Nanobodies for structural biology, Nature Protocols, 2014, pp. 674-693, vol. 9, No. 3, Nature America, Inc.

Patent Examination Report No. 2 dated May 22, 2015, AU2011278244.

PCT International Preliminary Report on Patentability, PCT/EP2011/062287 dated Jan. 22, 2013.

PCT International Search Report and Written Opinion, PCT/EP2011/062287, dated Sep. 5, 2011.

Rasmussen et al., Crystal structure of the B2 adrenergic receptor-Gs protein complex, Nature, Sep. 29, 2011, pp. 549-555, vol. 477, Macmillan Publishers Limited.

Rasmussen et al., Crystal structure of the human β2 adrenergic G-Protein-coupled receptor, Nature, 2007, pp. 383-88, Nature Publishing Group.

Rasmussen et al., Structure of a nanoody-stabilized active state of the beta2 adrenoceptor, Nature, Jan. 13, 2011, pp. 175-180, vol. 469, No. 7329.

Ring et al., Adrenaline-activated structure of B2-adrenoceptor stabilized by an engineered nanobody, Nature, 2013, pp. 1-5, Macmillan Publishers Limited.

Irannejad et al., Conformational biosensors reveal GPCR signalling from endosomes, Nature, Mar. 28, 2013, pp. 534-538, vol. 495, Macmillan Publishers Limited.

Japanese Notice of Rejection dated May 17, 2016, Japanese Patent Application No. 2014-516358.

Kobilka et al., G-protein-coupled receptors, KUNGL. Vetenskaps-Akademien The Royal Swedish Academy of Sciences, Oct. 10, 2012, pp. 1-15.

Kobilka, The structural basis of G-Protein-Coupled Receptor Signaling, Angewandte Chemie International Edition, 2013, pp. 2-11, vol. 52, Wiley-VCH Verlag GmbH & Co.

Kruse et al., Activation and allosteric modulation of muscarinic acetylcholine receptor, Nature, Dec. 5, 2013, pp. 101-106, vol. 504, No. 7478.

Mancia et al., Production and characterization of monoclonal antibodies sensitive to conformation in the 5HT2c serotonin receptor, PNAS, Mar. 13, 2007, pp. 4303-4308, vol. 104, No. 11.

Huang et al., Structural insights into u-opioid receptor activation, Nature, 2015, pp. 1-7, vol. 000, Macmillan Publishers Limited.

Seifert et al., Reconstitution of beta2-adrenoceptor-GTP-binding-protein interaction in Sf9 cells—high coupling efficiency in a beta2-adrenoceptor-G(s alpha) fusion protein. Eur. J. Biochem. 255(2):369-382, 1998.

Shohei Koide, Engineering of recombinant crystallization chaperones, Current Opinion in Structural Biology, 2009, pp. 449-457, vol. 19, Elsevier.

Sounier et al., Propagation of conformational changes during μ-opioid receptor activation, Nature, 2015, pp. 1-4, Macmillan Publishers Limited.

Srivastava et al., High-resolution structure of the human GPR40 receptor bound to allosteric agonist TAK-875, Nature, 2014, pp. 1-4, vol. 000, Macmillan Publishers Limited.

Staus et al., Regulation of beta2-Adrenergic Receptor Function by Conformationally Selective Single-Domain Intrabodies, Molecular Pharmacology, Mar. 2014, pp. 472-481, vol. 85, No. 3.

Steyaert et al., Nanobody stabilization of G protein-coupled receptor conformational states, Current Opinion in Structural Biology, 2011, pp. 567-572, vol. 21, Elsevier Ltd.

Wesolowski et al., Single domain antibodies: promising experimental and therapeutic tools in infection and immunity. Med. Microbial. Immunol. 198:157-174, 2009; Epub Jun. 16, 2009.

Paul, William E., Fundamental Immunology, 3rd Edition, 1993, pp. 292-295.

Vajdos et al., Comprehensive Functional Maps of the Antigen-binding Site of an Anti-ErbB2 Antibody Obtained with Shotgun Scanning Mutagenesis, J. Mol. Biol., 2002, pp. 415-428, vol. 320.

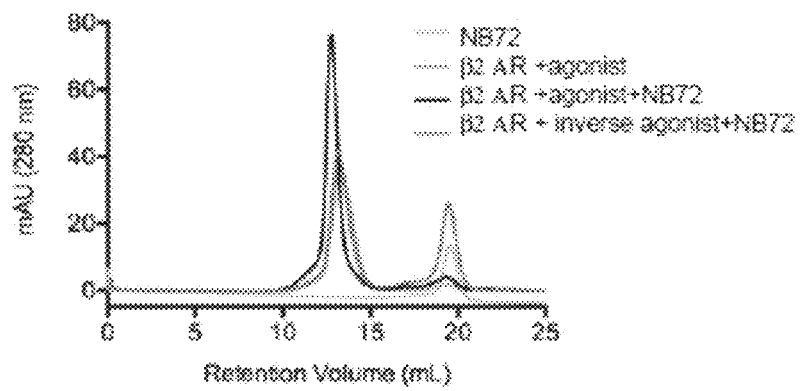
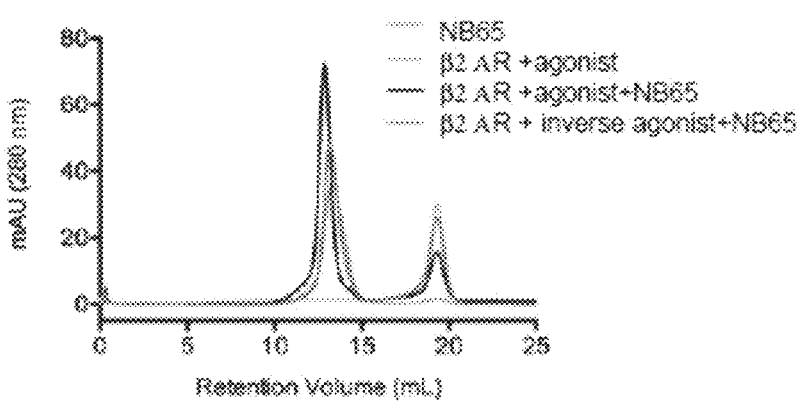
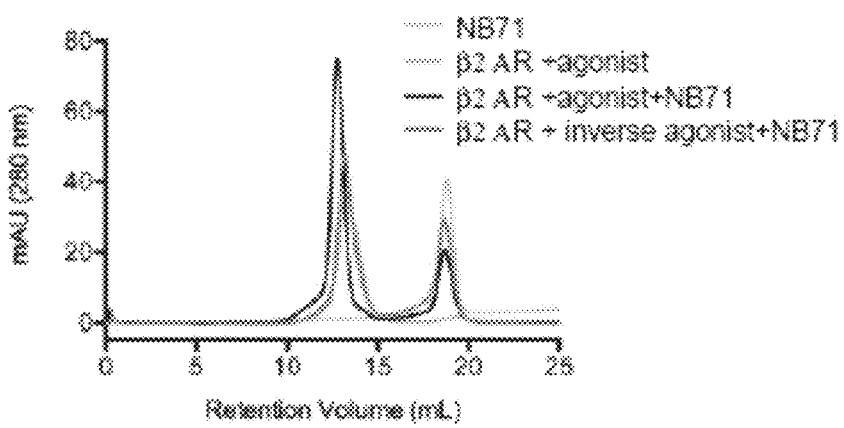
*FIG. 3A*

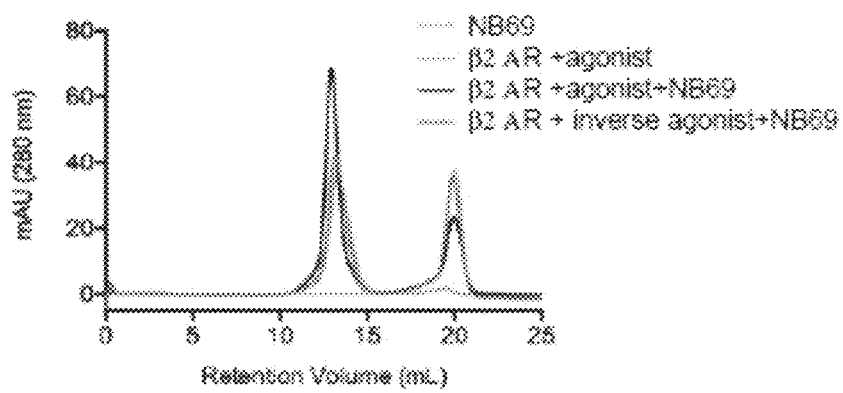
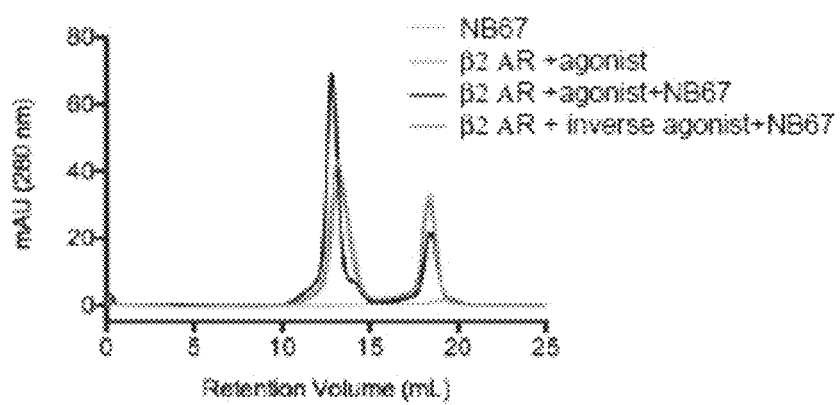
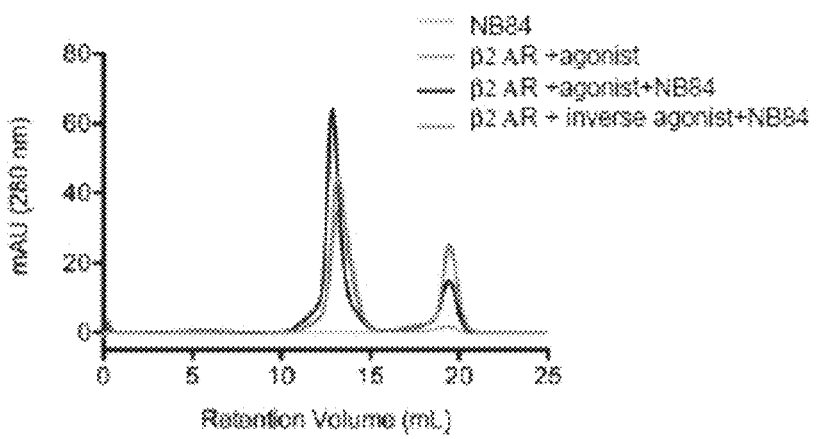
*FIG. 3B*

FIG. 12

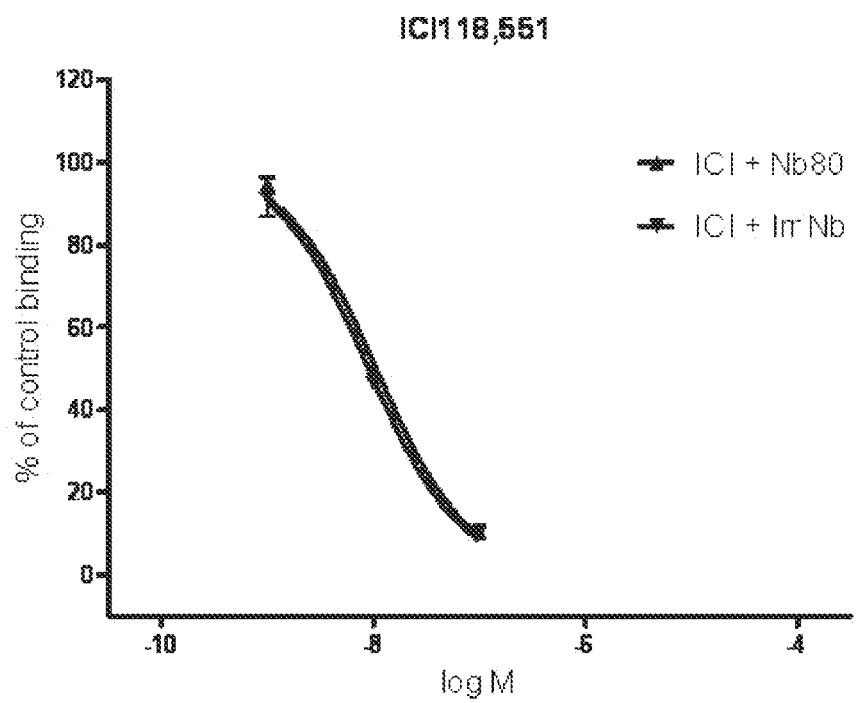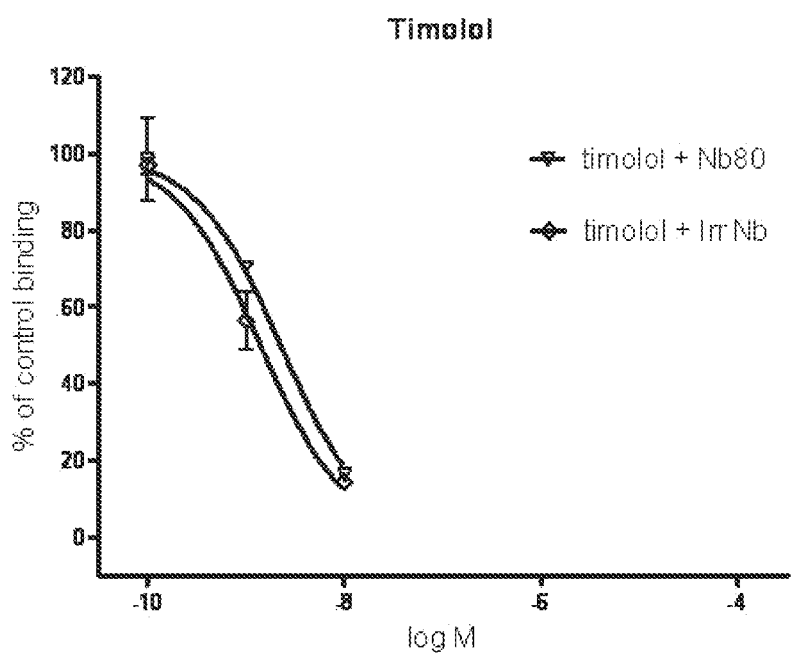
FIG. 16B

```
β2AR  MGQ---------PGNGS--------------AFLLAPNGSHA----PDHDVTQERDEVWVVG        35
β1AR  MGAGVLVLGASEPGNLSSAAPLPDGAATAARLLVPASPPASLLPPASESPEPLSQQWTAG         60
      *** *                                 *  **.*    .: ..:*..*

β2AR  MGIVMSLIVLAIVFGNVLVITAIAKFERLQTVTNYFITSLACADLVMGLAVVPFGAAHIL         95
β1AR  MGLLMALIVLLIVAGNVLVIVAIAKTPRLQTLTNLFIMSLASADLVMGLLVVPFGATIVV        120
      **::*:*** **:** ******.****  ***:**:* *:**:******* ******   ::

β2AR  MKMWTFGNFWCEFWTSIDVLCVTASIETLCVIAVDRYFAITSPFKYQSLLTKNKARVIIL        155
β1AR  WGRWEYGSFFCELWTSVDVLCVTASIETLCVIALDRYLAITSPFRYQSLLTRARARGLVC        180
       : *: *.*:**:***:***************:***:******:******:: ** :

β2AR  MVWIVSGLTSFLPIQMHWYRATHQEAINCYANETCCDFFTNQAYAIASSIVSFYVPLVIM        215
β1AR  TVWAISALVSFLPILMHWWRAESDEARRCYNDPKCCDFVTNRAYAIASSVVSFYVPLCIM        240
       ** :*.* *****: *** **.::**.***:  ****.**:*******:****** **

β2AR  VFVYSRVFQEEAKRQLQKIDKSEGRFH------VQNLSQVEQ-----------------        250
β1AR  AFVYLRVFREAQKQVKKIDSCERRFLGGPARPPSPSPSPVPAPAPPGPPRPAAAATAP        300
      .*** ***:* *::*::***. * **                *

β2AR  --DGRTGHGLRRSSKFCLKEHKALKTLGIIMGTFTLCWLPFFIVNIVHVIQDNLIRKEVY        308
β1AR  LANGRAGK--RRPSRLVALREQKALKTLGIIMGVFTLCWLPFFLANVVKAFHRELVPDRLF       359
         **:**   **.*::.*::::*:***********.:*********:.**:   *::*   :

β2AR  ILLNWIGYVNSGFNPLIYCRSPDFRIAFQELLCLRRSSLK---AYGNGYSSNGNTGEQ-        363
β1AR  VFFNWLGYANSAFNPIIYCRSPDFRKAFQRLLCCARRAARRRHATHGDRPRASGCLARPG       419
      :::**:***.**.***:*******:***.***  *.::  * :*  ..  :    .

β2AR  ---SGYHVQEKENKLLCEDLPG--TEDFVGHQGTVPSDNIDSQGRNCS---TNDSLL           413
β1AR  PPPSPGAASDDDDDDVVGATPPARLLEPWAGCNGGAAADSDSSLDEPCRPGFASESKV         477
         *    :    .   :  **    :*        ..     .:    *   : .  *          :
```

FIG. 17

SEQUENCE LISTING

```
<160> NUMBER OF SEQ ID NOS: 71

<210> SEQ ID NO 1
<211> LENGTH: 120
<212> TYPE: PRT
<213> ORGANISM: Lama glama

<400> SEQUENCE: 1

Gln Val Gln Leu Gln Glu Ser Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
            35                  40                  45

Ala Ala Ile His Ser Gly Gly Ser Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Lys Asp Tyr Gly Ala Val Leu Tyr Glu Tyr Asp Tyr Trp Gly Gln
                100                 105                 110

Gly Thr Gln Val Thr Val Ser Ser
            115                 120

<210> SEQ ID NO 2
<211> LENGTH: 120
```

```
<212> TYPE: PRT
<213> ORGANISM: Lama glama

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Ala Ile His Ser Gly Gly Ser Thr Asn Tyr Ala Asn Ser Val Lys
    50                  55                  60

Gly Arg Phe Thr Ile Ser Arg Asp Asn Ala Ala Asn Thr Val Tyr Leu
65                  70                  75                  80

Gln Met Asn Ser Leu Lys Pro Glu Asp Thr Ala Val Tyr Tyr Cys Asn
                85                  90                  95

Val Lys Asp Tyr Gly Ala Val Leu Tyr Glu Tyr Asp Tyr Trp Gly Gln
            100                 105                 110

Gly Thr Gln Val Thr Val Ser Ser
        115                 120

<210> SEQ ID NO 3
<211> LENGTH: 120
<212> TYPE: PRT
<213> ORGANISM: Lama glama

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Arg Arg Glu Leu Val
        35                  40                  45

Ala Ala Ile His Ser Gly Gly Ser Thr Asn Tyr Ala Asn Ser Val Lys
    50                  55                  60

Gly Arg Phe Thr Ile Ser Arg Asp Asn Ala Ala Asn Thr Val Tyr Leu
65                  70                  75                  80

Gln Met Asn Ser Leu Lys Pro Glu Asp Thr Ala Val Tyr Tyr Cys Asn
                85                  90                  95

Val Lys Asp Tyr Gly Ala Val Leu Tyr Glu Tyr Asp Tyr Trp Gly Gln
            100                 105                 110

Gly Thr Gln Val Thr Val Ser Ser
        115                 120

<210> SEQ ID NO 4
<211> LENGTH: 120
<212> TYPE: PRT
<213> ORGANISM: Lama glama

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Ala Ile His Ser Gly Gly Ser Thr Asn Tyr Ala Asn Ser Val Lys
```

```
            50                  55                  60
Gly Arg Phe Thr Ile Ser Arg Asp Asn Ala Ala Asn Thr Val Tyr Leu
 65                  70                  75                  80

Gln Met Asn Ser Leu Lys Pro Glu Asp Thr Ala Val Tyr Tyr Cys Asn
                 85                  90                  95

Val Lys Asp Tyr Gly Ala Val Leu Tyr Glu Tyr Asp Tyr Trp Gly Gln
                100                 105                 110

Gly Thr Gln Val Thr Val Ser Ser
            115                 120
```

<210> SEQ ID NO 5
<211> LENGTH: 120
<212> TYPE: PRT
<213> ORGANISM: Lama glama

<400> SEQUENCE: 5

```
Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ser Ile Phe Ser Ile Asn
                 20                  25                  30

Thr Met Gly Trp Tyr Arg Gln Ala Pro Gly Lys Gln Arg Glu Leu Val
                 35                  40                  45

Ala Ala Ile His Ser Gly Gly Ser Thr Asn Tyr Ala Asp Ser Val Arg
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Val Lys Asp Tyr Gly Ala Val Leu Tyr Glu Tyr Asp Tyr Trp Gly Gln
                100                 105                 110

Gly Thr Gln Val Thr Val Ser Ser
            115                 120
```

<210> SEQ ID NO 6
<211> LENGTH: 119
<212> TYPE: PRT
<213> ORGANISM: Lama glama

<400> SEQUENCE: 6

```
Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ser Ile Phe Ser Leu Asn
                 20                  25                  30

Asp Met Gly Trp Tyr Arg Gln Ala Pro Gly Lys Gln Arg Glu Leu Val
                 35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Val Val Ala Gly Thr Phe Ser Thr Tyr Asp Tyr Trp Gly Gln Gly
                100                 105                 110

Thr Gln Val Thr Val Ser Ser
            115
```

-continued

<210> SEQ ID NO 7
<211> LENGTH: 119
<212> TYPE: PRT
<213> ORGANISM: Lama glama

<400> SEQUENCE: 7

Gln Val Gln Leu Gln Glu Ser Gly Gly Gly Leu Val Gln Ala Gly Gly
1               5                   10                  15

Pro Leu Arg Leu Ser Cys Ala Ala Ser Gly Ser Ile Phe Ser Leu Asn
            20                  25                  30

Asp Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Val Ala Gly Thr Phe Ser Thr Tyr Asp Tyr Trp Gly Gln Gly
            100                 105                 110

Thr Gln Val Thr Val Ser Ser
        115

<210> SEQ ID NO 8
<211> LENGTH: 119
<212> TYPE: PRT
<213> ORGANISM: Lama glama

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Leu Asn
            20                  25                  30

Asp Met Gly Trp Tyr Arg Gln Ala Pro Gly Lys Gln Arg Glu Leu Val
        35                  40                  45

Ala Ala Ile Ser Ser Gly Gly Arg Leu Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Val Ala Gly Thr Phe Ser Thr Tyr Asp Tyr Trp Gly Gln Gly
            100                 105                 110

Thr Gln Val Thr Val Ser Ser
        115

<210> SEQ ID NO 9
<211> LENGTH: 119
<212> TYPE: PRT
<213> ORGANISM: Lama glama

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Leu Asn
            20                  25                  30

Asp Met Gly Trp Tyr Arg Gln Ala Pro Gly Lys Gln Arg Glu Leu Val
        35                  40                  45

```
Ala Ala Ile Ser Ser Gly Gly Arg Leu Asn Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Val Val Ala Gly Thr Phe Ser Thr Tyr Asp Tyr Trp Gly Gln Gly
            100                 105                 110

Thr Gln Val Thr Val Ser Ser
        115

<210> SEQ ID NO 10
<211> LENGTH: 119
<212> TYPE: PRT
<213> ORGANISM: Lama glama

<400> SEQUENCE: 10

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Ser Ile Phe Ser Leu Asn
             20                  25                  30

Asp Met Gly Trp Tyr Arg Gln Ala Pro Gly Lys Gln Arg Asp Leu Val
             35                  40                  45

Ala Ala Ile Thr Ser Gly Gly Ser Thr Lys Tyr Ala Asp Ser Val Lys
         50                  55                  60

Gly Arg Phe Thr Val Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Lys Val Ala Gly Thr Phe Ser Ile Tyr Asp Tyr Trp Gly Gln Gly
            100                 105                 110

Thr Gln Val Thr Val Ser Ser
        115

<210> SEQ ID NO 11
<211> LENGTH: 119
<212> TYPE: PRT
<213> ORGANISM: Lama glama

<400> SEQUENCE: 11

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Ser Ile Phe Ser Leu Asn
             20                  25                  30

Asp Met Gly Trp Tyr Arg Gln Ala Pro Gly Lys Leu Arg Glu Leu Val
             35                  40                  45

Ala Ala Val Thr Ser Gly Gly Ser Thr Asn Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Lys Val Ala Gly Thr Phe Ser Ile Tyr Asp Tyr Trp Gly Gln Gly
            100                 105                 110

Thr Gln Val Thr Val Ser Ser
        115
```

<210> SEQ ID NO 12
<211> LENGTH: 119
<212> TYPE: PRT
<213> ORGANISM: Lama glama

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Leu Asn
            20                  25                  30

Asp Met Gly Trp Tyr Arg Gln Ala Pro Gly Lys Leu Arg Glu Leu Val
        35                  40                  45

Ala Ala Ile Thr Ser Gly Gly Ser Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ala Glu Asp Thr Ala Val Tyr Tyr Cys Asn
                85                  90                  95

Ala Lys Val Ala Gly Thr Phe Ser Ile Tyr Asp Tyr Trp Gly Gln Gly
            100                 105                 110

Thr Gln Val Thr Val Ser Ser
        115

<210> SEQ ID NO 13
<211> LENGTH: 119
<212> TYPE: PRT
<213> ORGANISM: Lama glama

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Leu Asn
            20                  25                  30

Asp Met Gly Trp Tyr Arg Gln Ala Pro Gly Lys Leu Arg Glu Leu Val
        35                  40                  45

Ala Ala Ile Thr Ser Gly Gly Ser Thr Lys Tyr Ala Asp Pro Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ala Glu Asp Thr Ala Val Tyr Tyr Cys Asn
                85                  90                  95

Ala Lys Val Ala Gly Thr Phe Ser Ile Tyr Asp Tyr Trp Gly Gln Gly
            100                 105                 110

Thr Gln Val Thr Val Ser Ser
        115

<210> SEQ ID NO 14
<211> LENGTH: 119
<212> TYPE: PRT
<213> ORGANISM: Lama glama

<400> SEQUENCE: 14

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Leu Asn
            20                  25                  30

Asp Met Gly Trp Tyr Arg Gln Ala Pro Gly Lys Leu Arg Glu Leu Val
            35                  40                  45

Ala Ala Ile Thr Ser Gly Gly Ser Thr Lys Tyr Ala Asp Ser Val Lys
 50                  55                  60

Gly Arg Phe Thr Ile Ser Arg Asp Asn Ala Lys Asn Thr Val Tyr Leu
65                  70                  75                  80

Gln Met Asn Ser Leu Lys Ala Glu Asp Thr Ala Val Tyr Tyr Cys Asn
                85                  90                  95

Ala Lys Val Ala Gly Thr Phe Ser Ile Tyr Asp Tyr Trp Gly Gln Gly
            100                 105                 110

Thr Gln Val Thr Val Ser Ser
            115

<210> SEQ ID NO 15
<211> LENGTH: 119
<212> TYPE: PRT
<213> ORGANISM: Lama glama

<400> SEQUENCE: 15

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Leu Asn
            20                  25                  30

Asp Met Gly Trp Tyr Arg Gln Ala Pro Gly Lys Gln Arg Glu Leu Val
            35                  40                  45

Ala Ala Ile Thr Ser Gly Arg Ser Thr Asn Tyr Ala Asp Ser Val Lys
 50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Val Ala Gly Thr Phe Ser Ile Tyr Asp Tyr Trp Gly Gln Gly
            100                 105                 110

Thr Gln Val Thr Val Ser Ser
            115

<210> SEQ ID NO 16
<211> LENGTH: 119
<212> TYPE: PRT
<213> ORGANISM: Lama glama

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Ser Gly Ser Ile Phe Ser Leu Asn
            20                  25                  30

Asp Met Gly Trp Tyr Arg Gln Ala Pro Gly Lys Gln Arg Glu Leu Val
            35                  40                  45

Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Val Ala Gly Thr Phe Ser Ile Tyr Asp Tyr Trp Gly Gln Gly
            100                 105                 110

```
Thr Gln Val Thr Val Ser Ser
        115

<210> SEQ ID NO 17
<211> LENGTH: 119
<212> TYPE: PRT
<213> ORGANISM: Lama glama

<400> SEQUENCE: 17

Gln Val Gln Leu Gln Glu Ser Gly Gly Gly Leu Val Gln Ala Gly Arg
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Val Pro Gly Lys Gln Arg Glu Leu Val
        35                  40                  45

Ala Ala Ile Thr Ser Gly Gly Ser Val Asn Tyr Ala Glu Pro Val Lys
    50                  55                  60

Gly Arg Phe Thr Ile Ser Arg Asp Asn Gly Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Val Ala Gly Thr Phe Ser Ile Tyr Asp Tyr Trp Gly Gln Gly
            100                 105                 110

Thr Gln Val Thr Val Ser Ser
        115

<210> SEQ ID NO 18
<211> LENGTH: 119
<212> TYPE: PRT
<213> ORGANISM: Lama glama

<400> SEQUENCE: 18

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Ser Asn Asn
            20                  25                  30

Ala Met Gly Trp His Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Leu Met Asn Ser Leu Lys Pro Glu Asp Thr Ala Val Tyr Tyr Cys Asn
                85                  90                  95

Ala Lys Val Pro Gly Thr Phe Ser Ile Tyr Asp Tyr Trp Gly Gln Gly
            100                 105                 110

Thr Gln Val Thr Val Ser Ser
        115

<210> SEQ ID NO 19
<211> LENGTH: 115
<212> TYPE: PRT
<213> ORGANISM: Lama glama

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Val Phe Ser Leu Pro
```

```
                       20                  25                  30
Thr Ala Gly Trp Tyr Arg Gln Ala Pro Gly Lys Gln Arg Glu Leu Val
             35                  40                  45

Ala Leu Ile Thr Gly Ser Gly Ser Thr His Tyr Ala Asp Ser Val Lys
 50                  55                  60

Gly Arg Phe Ala Ile Ser Arg Glu Tyr Ser Lys Lys Thr Met Asp Leu
 65                  70                  75                  80

Gln Met Asn Ser Leu His Arg Glu Asp Thr Ala Val Tyr Phe Cys Tyr
                 85                  90                  95

Tyr Arg Ser Thr Phe Thr Glu Tyr Trp Gly Gln Gly Thr Gln Val Thr
             100                 105                 110

Val Ser Ser
         115

<210> SEQ ID NO 20
<211> LENGTH: 120
<212> TYPE: PRT
<213> ORGANISM: Lama glama

<400> SEQUENCE: 20

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Thr Ile Ser Ser Phe Ile
             20                  25                  30

Ala Met Gly Trp Tyr Arg Gln Ser Pro Gly Lys Gln Arg Glu Leu Val
             35                  40                  45

Ala Gly Ile Thr Ser Gly Gly Glu Thr Asn Tyr Glu Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Thr Leu Lys Pro Glu Asp Thr Ala Val Tyr Tyr Cys Asn
                 85                  90                  95

Ala Gln Val Phe Ala Asp Ile Phe Asn Leu Ile Asn Tyr Trp Gly Gln
             100                 105                 110

Gly Thr Gln Val Thr Val Ser Ser
         115                 120

<210> SEQ ID NO 21
<211> LENGTH: 118
<212> TYPE: PRT
<213> ORGANISM: Lama glama

<400> SEQUENCE: 21

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Thr Ile Phe Ser Pro Asn
             20                  25                  30

Thr Met Ala Trp Tyr Arg Gln Ala Pro Gly Lys Gln Arg Glu Leu Val
             35                  40                  45

Ala Leu Ile Thr Ser Gly Gly Ser Arg Asn Tyr Ala Asp Tyr Val Lys
 50                  55                  60

Gly Arg Phe Thr Ile Ser Arg Asp Asn Ala Lys Asn Thr Leu Tyr Leu
 65                  70                  75                  80

Gln Met Asn Asn Leu Lys Pro Glu Asp Thr Ala Val Tyr Tyr Cys Asn
                 85                  90                  95

Tyr Gln Thr Val Phe Phe Gly Asn Ala Glu Ala Trp Gly Gln Gly Thr
```

```
                 100                 105                 110

Gln Val Thr Val Ser Ser
            115

<210> SEQ ID NO 22
<211> LENGTH: 122
<212> TYPE: PRT
<213> ORGANISM: Lama glama

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ser Thr Ser Gly Asp Ile Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Gly Val Tyr Tyr Cys Asn
                85                  90                  95

Ala Arg Gly Ile Tyr Ser Asp Tyr Ala Phe Ala Asp Phe Asn Ser Trp
            100                 105                 110

Gly Gln Gly Thr Gln Val Thr Val Ser Ser
        115                 120

<210> SEQ ID NO 23
<211> LENGTH: 114
<212> TYPE: PRT
<213> ORGANISM: Lama glama

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Ser Ser Gly Ser Arg Phe Ser Phe Ile
            20                  25                  30

Thr Met Gly Trp Leu Arg Gln Ala Pro Gly Lys Gln Arg Glu Leu Val
        35                  40                  45

Ala Thr Leu Ser Gly Asp Asn Thr Asn Tyr Ser Asp Ala Val Lys Gly
    50                  55                  60

Arg Phe Thr Ile Ser Arg Asp Asn Ala Arg Asn Thr Val Tyr Leu Gln
65                  70                  75                  80

Met Asn Gly Leu Lys Pro Glu Asp Thr Gly Thr Tyr Tyr Cys Arg Gly
                85                  90                  95

Thr Ser Val Leu Tyr Asp Val Trp Gly Gln Gly Thr Gln Val Thr Val
            100                 105                 110

Ser Ser

<210> SEQ ID NO 24
<211> LENGTH: 124
<212> TYPE: PRT
<213> ORGANISM: Lama glama

<400> SEQUENCE: 24

Gln Val Gln Leu Gln Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Gly Tyr
            20                  25                  30

Ala Met Asn Trp Val Arg Gln Ala Pro Gly Lys Gly Pro Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

His Ala Arg Asp Ile Tyr Ser Asp Phe Leu Gly Gln Tyr Glu Tyr Asp
            100                 105                 110

Tyr Trp Gly Gln Gly Thr Gln Val Thr Val Ser Ser
            115                 120
```

<210> SEQ ID NO 25
<211> LENGTH: 116
<212> TYPE: PRT
<213> ORGANISM: Lama glama

<400> SEQUENCE: 25

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Glu Leu Arg Trp Tyr Arg Gln Ala Pro Gly Lys Gln His Glu Leu Val
        35                  40                  45

Ala Gly Ile Thr Thr Gly Gly Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Asn Leu Arg Pro Glu Asp Thr Ala Val Tyr Ala Cys Asn
                85                  90                  95

Ala Asn Trp Asp Leu Leu Ser Asp Tyr Trp Gly Gln Gly Thr Gln Val
            100                 105                 110

Thr Val Ser Ser
            115
```

<210> SEQ ID NO 26
<211> LENGTH: 123
<212> TYPE: PRT
<213> ORGANISM: Lama glama

<400> SEQUENCE: 26

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Asp Leu Val
        35                  40                  45

Ala Ser Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95
```

Val Gln Gly Thr Gly Pro Ser Ser Trp Leu Phe Asn Glu Tyr Asp Tyr
            100                 105                 110

Trp Gly Gln Gly Thr Gln Val Thr Val Ser Ser
        115                 120

<210> SEQ ID NO 27
<211> LENGTH: 123
<212> TYPE: PRT
<213> ORGANISM: Lama glama

<400> SEQUENCE: 27

Gln Val Gln Leu Gln Glu Ser Gly Gly Gly Leu Val Gln Pro Gly Gly
1               5                   10                  15

Ser Leu Gly Leu Ser Cys Ala Ala Ser Gly Ser Ile Phe Ser Ile Asn
            20                  25                  30

Ser Met Gly Trp Tyr Arg Gln Ala Pro Gly Lys Gln Arg Glu Leu Val
        35                  40                  45

Ala Ala Ile Thr Ser Asp Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Val Cys Asn
                85                  90                  95

Ala Asp Ser Val Tyr Ser Asp Phe Leu Gly Lys Tyr Gly Tyr Asp Tyr
            100                 105                 110

Trp Gly Gln Gly Thr Gln Val Thr Val Ser Ser
        115                 120

<210> SEQ ID NO 28
<211> LENGTH: 123
<212> TYPE: PRT
<213> ORGANISM: Lama glama

<400> SEQUENCE: 28

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Leu Asn
            20                  25                  30

Ala Met Arg Trp Tyr Arg Gln Ala Pro Gly Lys Gln Arg Glu Leu Val
        35                  40                  45

Ala Ala Ile Thr Ser Asp Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ser Val Tyr Ser Asp Phe Leu Gly Lys Tyr Glu Tyr Asp Tyr
            100                 105                 110

Trp Gly Gln Gly Thr Gln Val Thr Val Ser Ser
        115                 120

<210> SEQ ID NO 29
<211> LENGTH: 123
<212> TYPE: PRT
<213> ORGANISM: Lama glama

<400> SEQUENCE: 29

Gln Val Gln Leu Gln Glu Ser Gly Gly Gly Leu Val Gln Ala Gly Gly

```
                1               5                   10                  15
            Ser Leu Arg Leu Ser Cys Ala Ala Ser Gly Ser Ile Phe Ser Ile Asn
                            20                  25                  30
            Ala Met Gly Trp Tyr Arg Gln Ala Pro Gly Lys Gln Arg Glu Leu Val
                            35                  40                  45
            Ala Ala Ile Thr Ser Gly Gly Ser Thr Thr Tyr Ala Asp Ser Val Lys
                            50                  55                  60
            Gly Arg Phe Thr Val Ser Arg Asp Asn Ala Lys Asn Thr Val Tyr Leu
             65                 70                  75                  80
            Gln Met Ile Arg Leu Lys Pro Glu Asp Thr Ala Val Tyr Tyr Cys His
                            85                  90                  95
            Val Arg Asp Ile Tyr Ser Asp Phe Leu Gly Gln Tyr Glu Tyr Asp Tyr
                            100                 105                 110
            Trp Gly Gln Gly Thr Gln Val Thr Val Ser Ser
                            115                 120
```

<210> SEQ ID NO 30
<211> LENGTH: 8
<212> TYPE: PRT
<213> ORGANISM: Lama glama

<400> SEQUENCE: 30

```
Gly Ser Ile Phe Ser Ile Asn Thr
1               5
```

<210> SEQ ID NO 31
<211> LENGTH: 8
<212> TYPE: PRT
<213> ORGANISM: Lama glama

<400> SEQUENCE: 31

```
Gly Ser Ile Phe Ser Leu Asn Asp
1               5
```

<210> SEQ ID NO 32
<211> LENGTH: 8
<212> TYPE: PRT
<213> ORGANISM: Lama glama

<400> SEQUENCE: 32

```
Gly Ser Ile Phe Ser Ile Asn Asp
1               5
```

<210> SEQ ID NO 33
<211> LENGTH: 8
<212> TYPE: PRT
<213> ORGANISM: Lama glama

<400> SEQUENCE: 33

```
Gly Thr Ile Phe Ser Asn Asn Ala
1               5
```

<210> SEQ ID NO 34
<211> LENGTH: 8
<212> TYPE: PRT
<213> ORGANISM: Lama glama

<400> SEQUENCE: 34

```
Gly Ser Val Phe Ser Leu Pro Thr
1               5
```

```
<210> SEQ ID NO 35
<211> LENGTH: 8
<212> TYPE: PRT
<213> ORGANISM: Lama glama

<400> SEQUENCE: 35

Gly Thr Ile Ser Ser Phe Ile Ala
1               5

<210> SEQ ID NO 36
<211> LENGTH: 8
<212> TYPE: PRT
<213> ORGANISM: Lama glama

<400> SEQUENCE: 36

Gly Thr Ile Phe Ser Pro Asn Thr
1               5

<210> SEQ ID NO 37
<211> LENGTH: 8
<212> TYPE: PRT
<213> ORGANISM: Lama glama

<400> SEQUENCE: 37

Gly Ser Ile Phe Ser Ile Asn Ala
1               5

<210> SEQ ID NO 38
<211> LENGTH: 8
<212> TYPE: PRT
<213> ORGANISM: Lama glama

<400> SEQUENCE: 38

Gly Ser Arg Phe Ser Phe Ile Thr
1               5

<210> SEQ ID NO 39
<211> LENGTH: 8
<212> TYPE: PRT
<213> ORGANISM: Lama glama

<400> SEQUENCE: 39

Gly Phe Thr Phe Ser Gly Tyr Ala
1               5

<210> SEQ ID NO 40
<211> LENGTH: 8
<212> TYPE: PRT
<213> ORGANISM: Lama glama

<400> SEQUENCE: 40

Gly Phe Ala Phe Ser Ser Tyr Glu
1               5

<210> SEQ ID NO 41
<211> LENGTH: 8
<212> TYPE: PRT
<213> ORGANISM: Lama glama

<400> SEQUENCE: 41

Gly Ser Ile Phe Ser Ile Asn Ser
1               5

<210> SEQ ID NO 42
<211> LENGTH: 8
```

<212> TYPE: PRT
<213> ORGANISM: Lama glama

<400> SEQUENCE: 42

Gly Ser Ile Phe Ser Leu Asn Ala
1               5

<210> SEQ ID NO 43
<211> LENGTH: 7
<212> TYPE: PRT
<213> ORGANISM: Lama glama

<400> SEQUENCE: 43

Ile His Ser Gly Gly Ser Thr
1               5

<210> SEQ ID NO 44
<211> LENGTH: 7
<212> TYPE: PRT
<213> ORGANISM: Lama glama

<400> SEQUENCE: 44

Ile Thr Ser Gly Gly Ser Thr
1               5

<210> SEQ ID NO 45
<211> LENGTH: 7
<212> TYPE: PRT
<213> ORGANISM: Lama glama

<400> SEQUENCE: 45

Ile Ser Ser Gly Gly Arg Leu
1               5

<210> SEQ ID NO 46
<211> LENGTH: 7
<212> TYPE: PRT
<213> ORGANISM: Lama glama

<400> SEQUENCE: 46

Val Thr Ser Gly Gly Ser Thr
1               5

<210> SEQ ID NO 47
<211> LENGTH: 7
<212> TYPE: PRT
<213> ORGANISM: Lama glama

<400> SEQUENCE: 47

Ile Thr Ser Gly Arg Ser Thr
1               5

<210> SEQ ID NO 48
<211> LENGTH: 7
<212> TYPE: PRT
<213> ORGANISM: Lama glama

<400> SEQUENCE: 48

Ile Thr Ser Gly Gly Ser Val
1               5

<210> SEQ ID NO 49
<211> LENGTH: 7
<212> TYPE: PRT
<213> ORGANISM: Lama glama

```
<400> SEQUENCE: 49

Ile Thr Gly Ser Gly Ser Thr
1               5

<210> SEQ ID NO 50
<211> LENGTH: 7
<212> TYPE: PRT
<213> ORGANISM: Lama glama

<400> SEQUENCE: 50

Ile Thr Ser Gly Gly Glu Thr
1               5

<210> SEQ ID NO 51
<211> LENGTH: 7
<212> TYPE: PRT
<213> ORGANISM: Lama glama

<400> SEQUENCE: 51

Ile Thr Ser Gly Gly Ser Arg
1               5

<210> SEQ ID NO 52
<211> LENGTH: 7
<212> TYPE: PRT
<213> ORGANISM: Lama glama

<400> SEQUENCE: 52

Ser Thr Ser Gly Asp Ile Thr
1               5

<210> SEQ ID NO 53
<211> LENGTH: 6
<212> TYPE: PRT
<213> ORGANISM: Lama glama

<400> SEQUENCE: 53

Leu Ser Gly Asp Asn Thr
1               5

<210> SEQ ID NO 54
<211> LENGTH: 8
<212> TYPE: PRT
<213> ORGANISM: Lama glama

<400> SEQUENCE: 54

Ile Asn Ser Gly Gly Gly Ser Thr
1               5

<210> SEQ ID NO 55
<211> LENGTH: 7
<212> TYPE: PRT
<213> ORGANISM: Lama glama

<400> SEQUENCE: 55

Ile Thr Thr Gly Gly Asn Thr
1               5

<210> SEQ ID NO 56
<211> LENGTH: 7
<212> TYPE: PRT
<213> ORGANISM: Lama glama

<400> SEQUENCE: 56
```

```
Ile Thr Ser Asp Gly Ser Thr
1               5
```

\<210\> SEQ ID NO 57
\<211\> LENGTH: 14
\<212\> TYPE: PRT
\<213\> ORGANISM: Lama glama

\<400\> SEQUENCE: 57

```
Asn Val Lys Asp Tyr Gly Ala Val Leu Tyr Glu Tyr Asp Tyr
1               5                   10
```

\<210\> SEQ ID NO 58
\<211\> LENGTH: 13
\<212\> TYPE: PRT
\<213\> ORGANISM: Lama glama

\<400\> SEQUENCE: 58

```
Asn Ala Val Val Ala Gly Thr Phe Ser Thr Tyr Asp Tyr
1               5                   10
```

\<210\> SEQ ID NO 59
\<211\> LENGTH: 13
\<212\> TYPE: PRT
\<213\> ORGANISM: Lama glama

\<400\> SEQUENCE: 59

```
Asn Ala Lys Val Ala Gly Thr Phe Ser Ile Tyr Asp Tyr
1               5                   10
```

\<210\> SEQ ID NO 60
\<211\> LENGTH: 13
\<212\> TYPE: PRT
\<213\> ORGANISM: Lama glama

\<400\> SEQUENCE: 60

```
Asn Ala Lys Val Pro Gly Thr Phe Ser Ile Tyr Asp Tyr
1               5                   10
```

\<210\> SEQ ID NO 61
\<211\> LENGTH: 9
\<212\> TYPE: PRT
\<213\> ORGANISM: Lama glama

\<400\> SEQUENCE: 61

```
Tyr Tyr Arg Ser Thr Phe Thr Glu Tyr
1               5
```

\<210\> SEQ ID NO 62
\<211\> LENGTH: 14
\<212\> TYPE: PRT
\<213\> ORGANISM: Lama glama

\<400\> SEQUENCE: 62

```
Asn Ala Gln Val Phe Ala Asp Ile Phe Asn Leu Ile Asn Tyr
1               5                   10
```

\<210\> SEQ ID NO 63
\<211\> LENGTH: 12
\<212\> TYPE: PRT
\<213\> ORGANISM: Lama glama

\<400\> SEQUENCE: 63

```
Asn Tyr Gln Thr Val Phe Phe Gly Asn Ala Glu Ala
```

```
1               5                   10
```

<210> SEQ ID NO 64
<211> LENGTH: 16
<212> TYPE: PRT
<213> ORGANISM: Lama glama

<400> SEQUENCE: 64

```
Asn Ala Arg Gly Ile Tyr Ser Asp Tyr Ala Phe Ala Asp Phe Asn Ser
1               5                   10                  15
```

<210> SEQ ID NO 65
<211> LENGTH: 9
<212> TYPE: PRT
<213> ORGANISM: Lama glama

<400> SEQUENCE: 65

```
Arg Gly Thr Ser Val Leu Tyr Asp Val
1               5
```

<210> SEQ ID NO 66
<211> LENGTH: 17
<212> TYPE: PRT
<213> ORGANISM: Lama glama

<400> SEQUENCE: 66

```
His Ala Arg Asp Ile Tyr Ser Asp Phe Leu Gly Gln Tyr Glu Tyr Asp
1               5                   10                  15

Tyr
```

<210> SEQ ID NO 67
<211> LENGTH: 10
<212> TYPE: PRT
<213> ORGANISM: Lama glama

<400> SEQUENCE: 67

```
Asn Ala Asn Trp Asp Leu Leu Ser Asp Tyr
1               5                   10
```

<210> SEQ ID NO 68
<211> LENGTH: 17
<212> TYPE: PRT
<213> ORGANISM: Lama glama

<400> SEQUENCE: 68

```
Asn Val Gln Gly Thr Gly Pro Ser Ser Trp Leu Phe Asn Glu Tyr Asp
1               5                   10                  15

Tyr
```

<210> SEQ ID NO 69
<211> LENGTH: 17
<212> TYPE: PRT
<213> ORGANISM: Lama glama

<400> SEQUENCE: 69

```
Asn Ala Asp Ser Val Tyr Ser Asp Phe Leu Gly Lys Tyr Glu Tyr Asp
1               5                   10                  15

Tyr
```

<210> SEQ ID NO 70
<211> LENGTH: 17
<212> TYPE: PRT
<213> ORGANISM: Lama glama

```
<400> SEQUENCE: 70

His Val Arg Asp Ile Tyr Ser Asp Phe Leu Gly Gln Tyr Glu Tyr Asp
1               5                   10                  15
Tyr

<210> SEQ ID NO 71
<211> LENGTH: 11
<212> TYPE: PRT
<213> ORGANISM: Artificial Sequence
<220> FEATURE:
<223> OTHER INFORMATION: HIV-derived TAT peptide

<400> SEQUENCE: 71

Tyr Gly Arg Lys Lys Arg Arg Gln Arg Arg Arg
1               5                   10
```

PROTEIN BINDING DOMAINS STABILIZING FUNCTIONAL CONFORMATIONAL STATES OF GPCRS AND USES THEREOF

CROSS-REFERENCE TO RELATED APPLICATIONS

This application is a continuation of U.S. patent application Ser. No. 15/409,285, filed Jan. 18, 2017, pending, which is a continuation of U.S. patent application Ser. No. 15/236,398, filed Aug. 13, 2016, now U.S. Pat. No. 9,689,872, issued Jun. 27, 2017, which is a continuation of U.S. patent application Ser. No. 13/810,652, filed Mar. 29, 2013, now U.S. Pat. No. 9,453,065, issued Sep. 27, 2016, which is a national phase entry under 35 U.S.C. § 371 of PCT International Patent Application PCT/EP2011/062287, filed Jul. 18, 2011, designating the United States of America and published in English as International Patent Publication WO 2012/007593 A1 on Jan. 19, 2012, which claims the benefit under Article 8 of the Patent Cooperation Treaty and under 35 U.S.C. § 119(e) to U.S. Provisional Patent Application Ser. No. 61/399,781, filed Jul. 16, 2010, and under Article 8 of the Patent Cooperation Treaty to United Kingdom Patent Application Serial No. 1014715.5, filed Sep. 6, 2010.

GOVERNMENT RIGHTS

This invention was made with Government support under Contract No. NS028471 awarded by the National Institutes of Health. The Government has certain rights in this invention.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The disclosure relates to the field of GPCR structure biology and signaling. In particular, the disclosure relates to protein binding domains directed against or capable of specifically binding to a functional conformational state of a G protein-coupled receptor (GPCR). More specifically, the disclosure provides protein binding domains that are capable of increasing the stability of a functional conformational state of a GPCR, in particular, increasing the stability of a GPCR in its active conformational state. The protein binding domains hereof can be used as a tool for the structural and functional characterization of G-protein-coupled receptors bound to various natural and synthetic ligands, as well as for screening and drug discovery efforts targeting GPCRs. Moreover, the invention also encompasses the diagnostic, prognostic and therapeutic usefulness of these protein binding domains for GPCR-related diseases.

BACKGROUND

G protein-coupled receptors (GPCRs) are the largest family of membrane proteins in the human genome. They play essential roles in physiologic responses to a diverse set of ligands, such as biogenic amines, amino acids, peptides, proteins, prostanoids, phospholipids, fatty acids, nucleosides, nucleotides, $Ca^{2+}$ ions, odorants, bitter and sweet tastants, pheromones and protons (Heilker et al. 2009). GPCRs are therapeutic targets for a broad range of diseases. GPCRs are characterized by seven transmembrane domains with an extracellular amino terminus and an intracellular carboxyl terminus, and are also called seven transmembrane or heptahelical receptors (Rosenbaum et al. 2009). Rhodopsin, a GPCR that is highly specialized for the efficient detection of light, has been the paradigm for GPCR signaling and structural biology due to its biochemical stability and natural abundance in bovine retina (Hofmann et al. 2009). In contrast, many GPCRs exhibit complex functional behavior by modulating the activity of multiple G protein isoforms, as well as G protein independent signaling pathways (e.g., β-arrestin). In some cases, a GPCR may exhibit basal activity toward a specific signaling pathway, even in the absence of a ligand. Orthosteric ligands that act on a GPCR can have a spectrum of effects on downstream signaling pathways. Full agonists maximally activate the receptor. Partial agonists elicit a submaximal stimulation, even at saturating concentrations. Inverse agonists inhibit basal activity, while neutral antagonists have no effect on basal activity, but competitively block binding of other ligands.

The complex behavior of GPCRs for hormones and neurotransmitters can be attributed to their structural plasticity (Kobilka and Deupi 2007). Evidence from functional and biophysical studies shows that GPCRs can exist in multiple functionally distinct conformational states (Kobilka and Deupi 2007). While this structural plasticity and dynamic behavior is essential for normal function, it contributes to their biochemical instability and difficulty in obtaining high-resolution crystal structures. To date, crystal structures have been reported for the human $β_2AR$ (Rasmussen et al. 2007; Rosenbaum et al. 2007; Cherezov et al. 2007; Hanson et al. 2008), the avian $β_1AR$ (Warne et al. 2008), and human A2 adenosine receptor (Jaakola et al. 2008). While rhodopsin can be crystallized from unmodified protein isolated from native tissue, these other GPCRs required expression in recombinant systems, stabilization of an inactive state by an inverse agonist and biochemical modifications to stabilize the receptor protein. The first crystal structure of the $β_2AR$ was stabilized by a selective Fab (Rasmussen et al. 2007). Subsequent structures of the $β_2AR$ and the A2 adenosine receptor were obtained with the aid of protein engineering: the insertion of T4Lysozyme into the third intracellular loop as originally described for the $β_2AR$ (Rosenbaum et al. 2007). Finally, crystals of the avian $β_1AR$ were grown from protein engineered with amino and carboxyl terminal truncations and deletion of the third intracellular loop, as well as six amino acid substitutions that enhanced thermostability of the purified protein (Warne et al. 2008).

Obtaining structures of an active state of a GPCR is more difficult because this state is relatively unstable. Fluorescence lifetime studies show that the $β_2AR$ is structurally heterogeneous in the presence of saturating concentrations of a full agonist (Ghanouni et al. 2001). This structural heterogeneity is incompatible with the formation of crystals. Stabilization of the active state of the $β_2AR$ requires the presence of its cognate G protein Gs, the stimulatory protein for adenylyl cyclase (Yao et al. 2009). To date, the only active state structure of GPCR is that of opsin, the ligand free form of rhodopsin (Park et al. 2008). These crystals were grown at acidic pH (5.5) where opsin has been shown to be structurally similar to light-activated rhodopsin (metarhodopsin II) at physiologic pH by FTIR spectroscopy. While the $\beta_2AR$ also exhibits higher basal activity at reduced pH, it is biochemically unstable (Ghanouni et al. 2000).

Unraveling the structures of different functional conformational states of GPCRs in complex with various natural and synthetic ligands and proteins is valuable, both for understanding the mechanisms of GPCR signal transduction as well as for structure-based drug discovery efforts. The development of new straightforward tools for high-resolution structure analysis of individual conformers of GPCRs is, therefore, needed.

BRIEF SUMMARY

A first aspect hereof relates to a protein binding domain capable of specifically binding to a functional conformational state of a GPCR.

In one embodiment, the protein binding domain is capable of stabilizing a functional conformational state of a GPCR upon binding. Preferably, the protein binding domain is capable of inducing a functional conformational state in a GPCR upon binding.

In another embodiment, the functional conformational state of a GPCR is selected from the group consisting of a basal conformational state, or an active conformational state or an inactive conformational state. Preferably, the functional conformational state of a GPCR is an active conformational state.

According to another embodiment, the protein binding domain is capable of specifically binding to an agonist-bound GPCR and/or enhances the affinity of a GPCR for an agonist.

According to another embodiment, the protein binding domain is capable of increasing the thermostability of a functional conformational state of a GPCR upon binding.

In a specific embodiment, the protein binding domain is capable of specifically binding to a conformational epitope of the functional conformational state of a GPCR. Preferably, the conformational epitope is an intracellular epitope. More preferably, the conformational epitope is comprised in a binding site for a downstream signaling protein. Most preferably, the conformational epitope is comprised in the G protein binding site.

Preferably, the protein binding domain hereof comprises an amino acid sequence that comprises four framework regions and three complementarity-determining regions, or any suitable fragment thereof. More preferably, the protein binding domain is derived from a camelid antibody. Most preferably, the protein binding domain comprises a nanobody sequence, or any suitable fragment thereof. For example, the nanobody comprises a sequence selected from the group consisting of SEQ ID NOS:1-29, or any suitable fragment thereof.

According to another embodiment, the GPCR is a mammalian protein, or a plant protein, or a microbial protein, or a viral protein, or an insect protein. The mammalian protein can be a human protein. In particular, the GPCR is chosen from the group comprising a GPCR of the Glutamate family of GPCRs, a GPCR of the Rhodopsin family of GPCRs, a GPCR of the Adhesion family of GPCRs, a GPCR of the Frizzled/Taste2 family of GPCRs, and a GPCR of the Secretin family of GPCRs. More specifically, the GPCR is an adrenergic receptor, such as an $\alpha$-adrenergic receptor or a $\beta$-adrenergic receptor, or wherein the GPCR is a muscarinic receptor, such as an $M_1$-muscarinic receptor or an $M_2$-muscarinic receptor, or an $M_3$-muscarinic receptor, or an $M_4$-muscarinic receptor, or an $M_5$-muscarinic receptor, or wherein the GPCR is an angiotensin receptor, such as an angiotensin II type 1 receptor or an angiotensin II type 2 receptor.

A second aspect hereof relates to a complex comprising: (i) a protein binding domain hereof, (ii) a GPCR in a functional conformational state, and (iii) optionally, a receptor ligand. The receptor ligand can be chosen from the group comprising a small molecule, a protein, a peptide, a protein scaffold, a nucleic acid, an ion, a carbohydrate or an antibody, or any suitable fragment thereof. The complex can be in a solubilized form or immobilized to a solid support. In particular, the complex is crystalline. The invention further encompasses a crystalline form of a complex comprising (i) a protein binding domain, (ii) a GPCR in a functional conformational state, and (iii) optionally, a receptor ligand, wherein the crystalline form is obtained by the use of a protein binding domain hereof.

A third aspect hereof relates to a cellular composition comprising a protein binding domain hereof and/or a complex hereof. Preferably, the protein binding domain comprised in the cellular composition is capable of stabilizing and/or inducing a functional conformational state of a GPCR upon binding of the protein binding domain.

A fourth aspect hereof relates to the use of a protein binding domain hereof or a complex hereof or a cellular composition hereof to stabilize and/or induce a functional conformational state of a GPCR.

According to one embodiment, the protein binding domain or the complex or the cellular composition can be used to crystallize and/or to solve the structure of a GPCR in a functional conformational state.

Also encompassed is a method of determining a crystal structure of a GPCR in a functional conformational state, the method comprising the steps of:
  (i) providing a protein binding domain hereof, a target GPCR, and optionally a receptor ligand,
  (ii) forming a complex of the protein binding domain, the GPCR, and optionally the receptor ligand, and
  (iii) crystallizing the complex of step (ii) to form a crystal, wherein the crystal structure is determined of a GPCR in a functional conformational state.

The above method of determining a crystal structure of a GPCR may further comprise the step of obtaining the atomic coordinates from the crystal.

According to another embodiment, the protein binding domain or the complex or the cellular composition can be used to capture a GPCR in a functional conformational state, optionally with a receptor ligand or with one or more downstream signaling proteins.

Also encompassed is a method of capturing a GPCR in a functional conformational state, the method comprising the steps of:
  (i) providing a protein binding domain hereof and a target GPCR, and
  (ii) forming a complex of the protein binding domain and the GPCR,
wherein a GPCR is captured in a functional conformational state.

Further, also encompassed is a method of capturing a GPCR in a functional conformational state, the method comprising the steps of:
  (i) applying a solution containing a GPCR in a plurality of conformational states to a solid support possessing an immobilized protein binding domain hereof,
  (ii) forming a complex of the protein binding domain and the GPCR, and
  (iii) removing weakly bound or unbound molecules, wherein a GPCR is captured in a functional conformational state.

The above methods of capturing a GPCR in a functional conformational state may comprise the step of purifying the complex.

According to another embodiment, also disclosed is the use of the protein binding domain, or the complex, or the cellular composition, hereof, in screening and/or identification programs for conformation-specific (drug) compounds or ligands of a GPCR.

Also encompassed is a method of identifying compounds capable of binding to a functional conformational state of a GPCR, the method comprising the steps of:
(i) Providing a GPCR and a protein binding domain hereof,
(ii) Providing a test compound, and
(iii) Evaluating whether the test compound binds to the functional conformational state of the GPCR, and
(iv) Selecting a compound that binds to the functional conformational state of the GPCR.

Preferably, the above-described method for identifying compounds further comprises the step of forming a complex comprising the protein binding domain and the GPCR in a functional conformational state, hereof. The complex may further comprise a receptor ligand, which can be chosen from the group comprising a small molecule, a protein, a peptide, a protein scaffold, a nucleic acid, an ion, a carbohydrate or an antibody, or any suitable fragment thereof. Preferably, the receptor ligand is a full agonist, or a partial agonist, or an inverse agonist, or an antagonist. Preferably, the protein binding domain and/or the complex are provided in essentially purified form. Alternatively, the protein binding domain and/or the complex are provided in a solubilized form. Alternatively, the protein binding domain and/or the complex is immobilized to a solid support. Alternatively, the protein binding domain and/or the complex is provided in a cellular composition.

According to another embodiment, the test compound used in the above-described method for identifying compounds is selected from the group comprising a polypeptide, a peptide, a small molecule, a natural product, a peptidomimetic, a nucleic acid, a lipid, a lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or nanobody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, or engineered CH2 domains (nanoantibodies).

Preferably, the test compounds are labeled. Further, a library of test compounds may be used. Further, the above-described method for identifying compounds may be a high-throughput screening method.

According to another specific embodiment, the protein binding domain or the complex or the cellular composition, all hereof, can be used to diagnose or prognose a GPCR-related disease, such as cancer, autoimmune disease, infectious disease, neurological disease, or cardiovascular disease.

A fifth aspect hereof relates to a pharmaceutical composition comprising a therapeutically effective amount of a protein binding domain hereof and at least one of a pharmaceutically acceptable carrier, adjuvant or diluent.

A sixth aspect hereof relates to the use of a protein binding domain hereof or a pharmaceutical composition hereof to modulate GPCR signaling activity, more specifically, to block G-protein-mediated signaling.

The protein binding domain or the pharmaceutical composition hereof may also be used in the treatment of a GPCR-related disease, such as cancer, autoimmune disease, infectious disease, neurological disease, or cardiovascular disease.

A seventh aspect hereof relates to a kit comprising a protein binding domain hereof or a complex hereof or a cellular composition hereof.

Other applications and uses of the amino acid sequences and polypeptides hereof will become clear to the skilled person from the further disclosure herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Panel a: Representative trace of size-exclusion chromatography (SEC) for Nb80. Purified $\beta_2$AR (20 µM) bound to an agonist ($\beta_2$AR-agonist) was incubated with and without 40 µM Nb80 (black and blue, respectively) for two hours at room temperature prior to analyzing by FPLC. In the presence of Nb80, the $\beta_2$AR-agonist elution peak increases in UV absorbance (280 nm) and elutes at an earlier volume than $\beta_2$AR-agonist alone, with a simultaneous decrease in the Nb80 elution peak (green), suggesting $\beta_2$AR-agonist-Nb80 complex formation. Incubation of $\beta_2$AR (20 µM) bound to an inverse agonist with Nb80 (red) resulted in a smaller shift and smaller increase in UV absorbance when compared to the $\beta_2$AR-agonist-Nb80 complex.

Panel b: Dose-response competition binding experiments on Sf9 insect cell membranes expressing $\beta_2$AR. Seven nanobodies that bound $\beta_2$AR by SEC were individually incubated for 90 minutes at room temperature with $\beta_2$AR-expressing membranes. All seven nanobodies increased the affinity of $\beta_2$AR for (−)-isoproterenol (Table 3). Nb80 (blue) was selected as the lead nanobody. Data represent the mean±s.e. of two independent experiments performed in triplicate.

Panel c: A fluorescence-based functional assay using monobromobimane- (mBBR-) labeled purified receptor shows that 1 µM Nb80 (blue) stabilizes a more active state of the $\beta_2$AR (bound to the full agonist (−)-isoproterenol) when compared with receptor in the absence of Nb80 (black). The active state is characterized by a quenching of mBBr fluorescence and a redshift in mBBr fluorescence (Yao et al. 2009).

Figure 2:
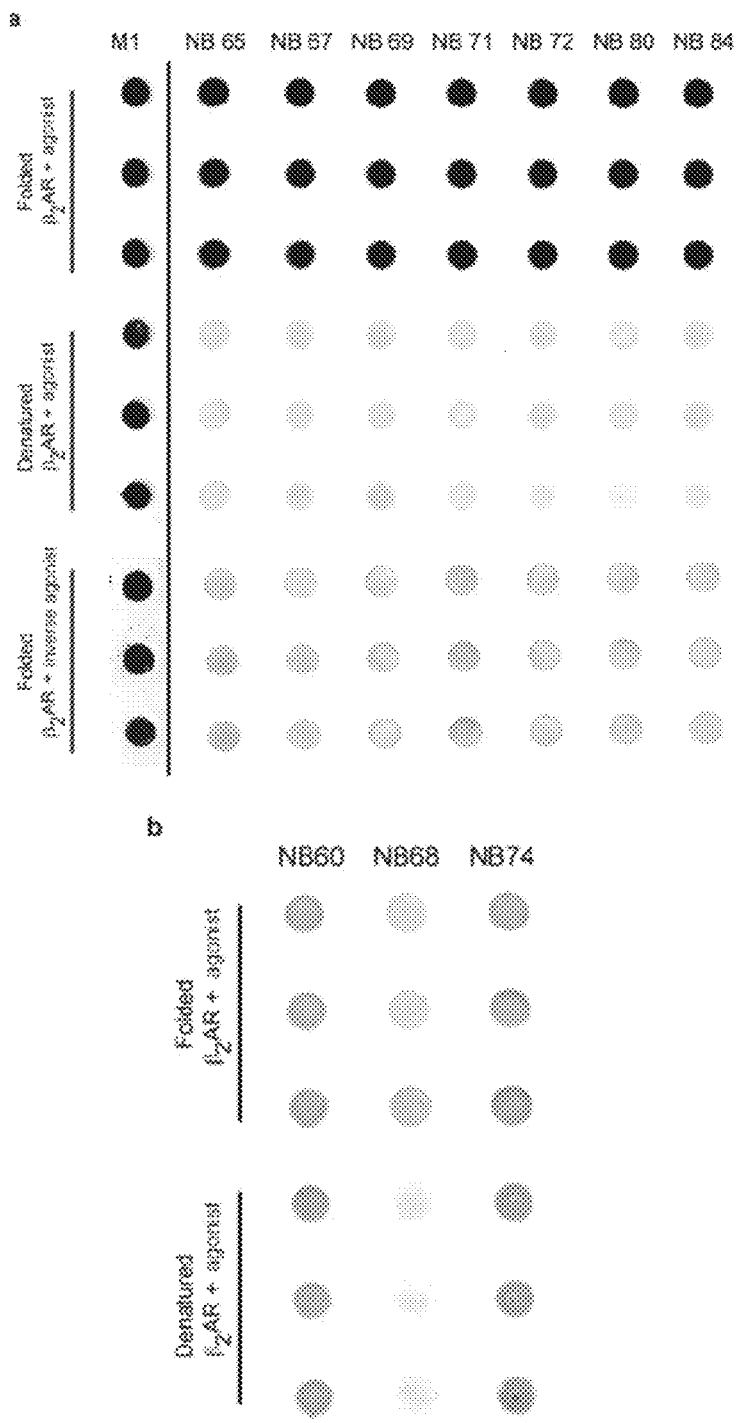

FIG. 2. Representative dot blots showing specificity of nanobodies to the tertiary structure of the $\beta_2$AR:

Panel a: Equal amounts of native or SDS-denatured purified $\beta_2$AR bound to an agonist (top and middle, respectively), or native $\beta_2$AR bound to an inverse agonist (bottom) were spotted in triplicate on nitrocellulose strips. The strips were blocked with 5% nonfat dry milk in PBS (pH 7.4) with 0.05% TWEEN®-20 and then incubated with 1 mg/ml of indicated nanobodies diluted in blocking buffer. Binding of nanobodies was detected by an anti-histidine (a-6His) primary mouse antibody, followed by incubation with goatanti-mouse IR-800-labeled secondary antibody. M1 antibody, which recognizes the linear FLAG epitope, was labeled with Alexa-688 and directly detected $\beta_2AR$. Dot blots were scanned and imaged using the Odyssey Infrared Imaging System (Li-cor Biosciences). Blots detecting nanobodies were processed separately from blots detecting $\beta_2AR$ by M1 since two different channels (800 nm versus 700 nm, respectively) were used for imaging; therefore, blots cannot be directly compared and quantified (i.e., comparison of binding of nanobodies versus M1 binding are only qualitative in nature).

Panel b: Representative dot blots showing nanobodies with reduced binding to natively folded $\beta_2AR$.

FIGS. 3A and 3B. Selective binding of nanobodies to the active state of the receptor: Purified $\beta_2AR$ (20 μM) bound to an agonist was incubated with and without 40 μM nanobodies (black and blue, respectively) for two hours at room temperature prior to analyzing by size exclusion chromatography. Samples of $\beta_2AR$ (20 μM) bound to an inverse agonist in the presence of nanobodies (red) were also analyzed. In the presence of several nanobodies (Nb72, Nb65, Nb71, Nb69, Nb67 and Nb84), the $\beta_2AR$-agonist elution peak increases in UV absorbance (280 nm) and elutes at an earlier volume (black line) than $\beta_2AR$-agonist alone (blue), with a simultaneous decrease in the Nb80 elution peak (green), suggesting $\beta_2AR$-agonist-Nb80 complex formation. The formation of a $\beta_2AR$-inverse agonist-Nb80 complex is not observed (red line).

Figure 4:
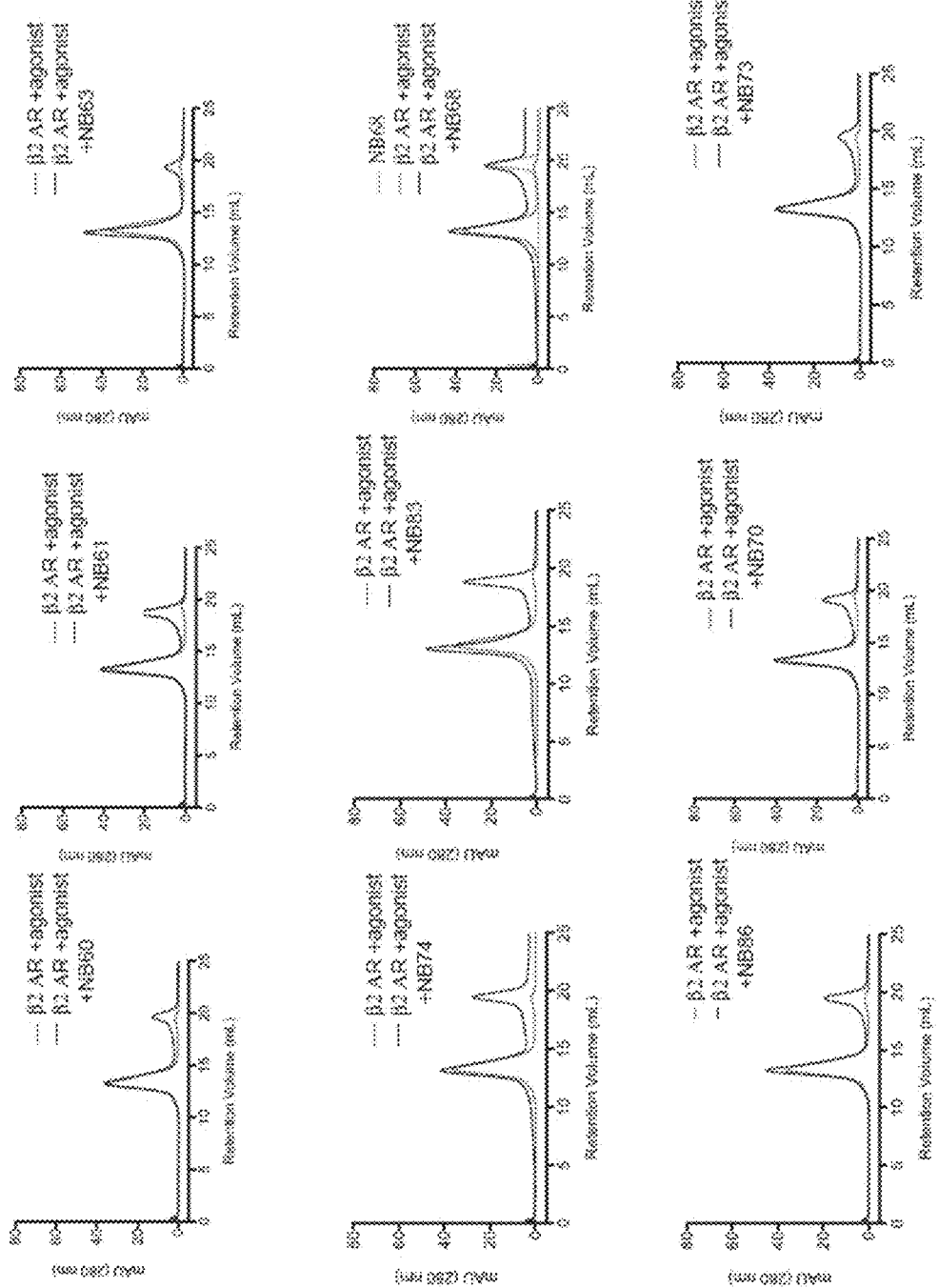
Figure 5A:
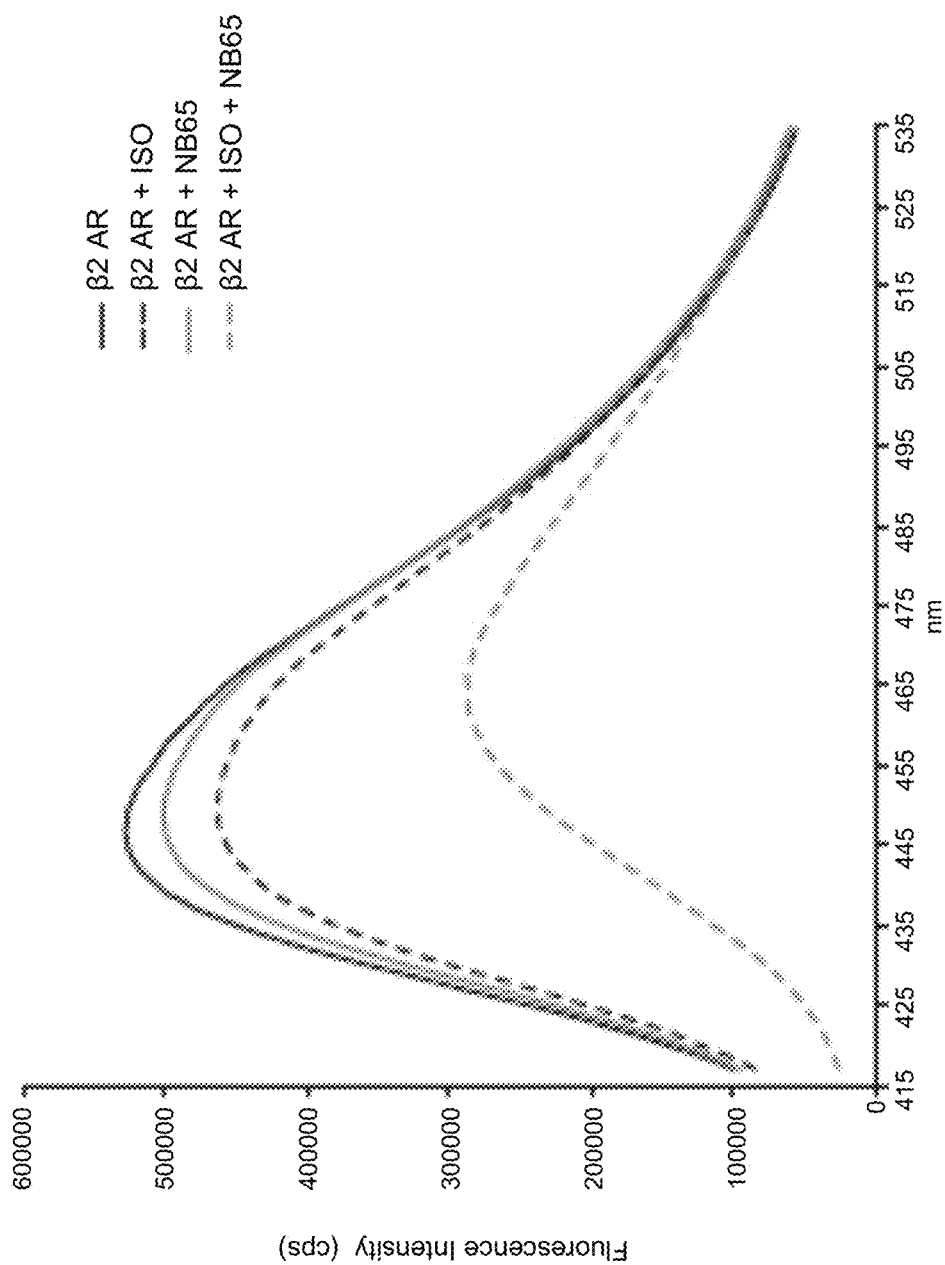
Figure 5B:
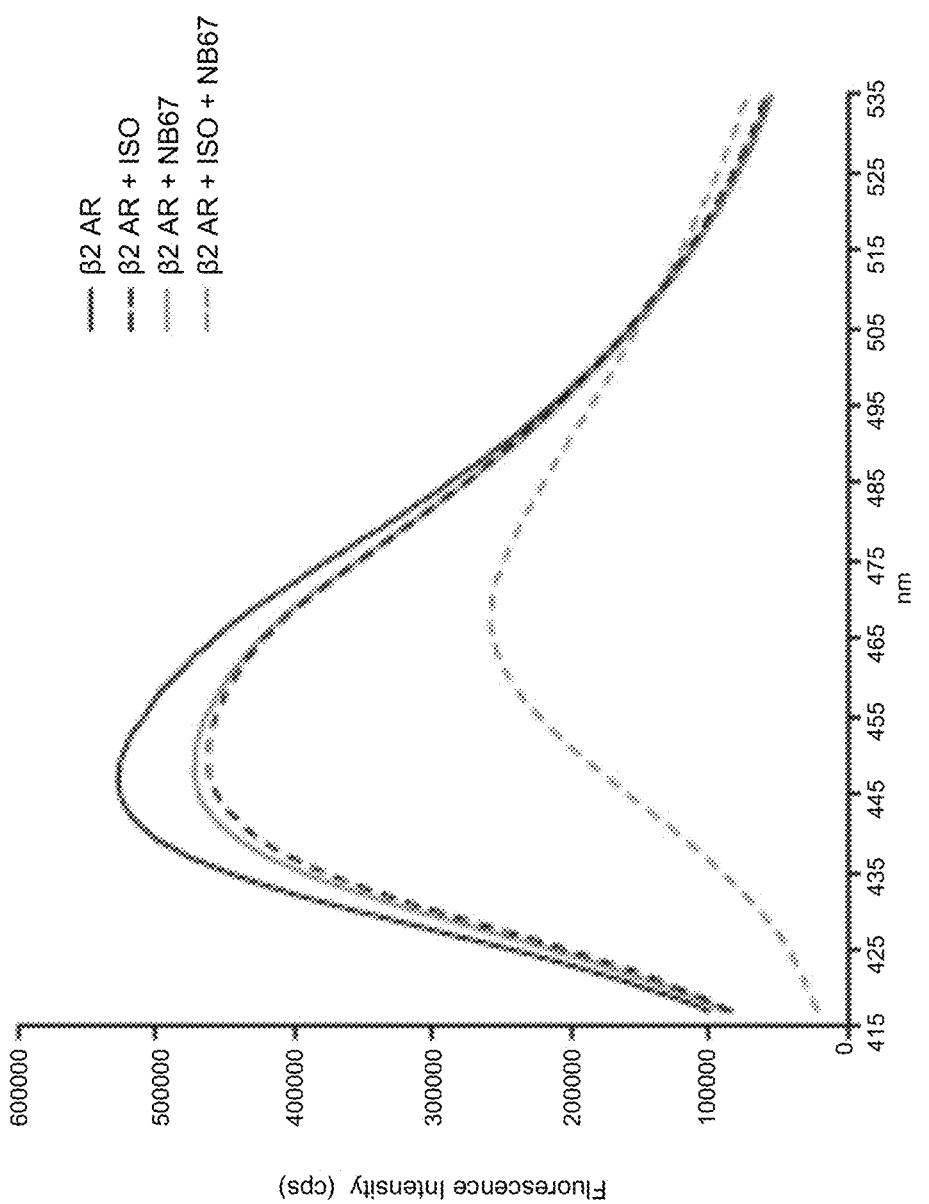
Figure 5C:
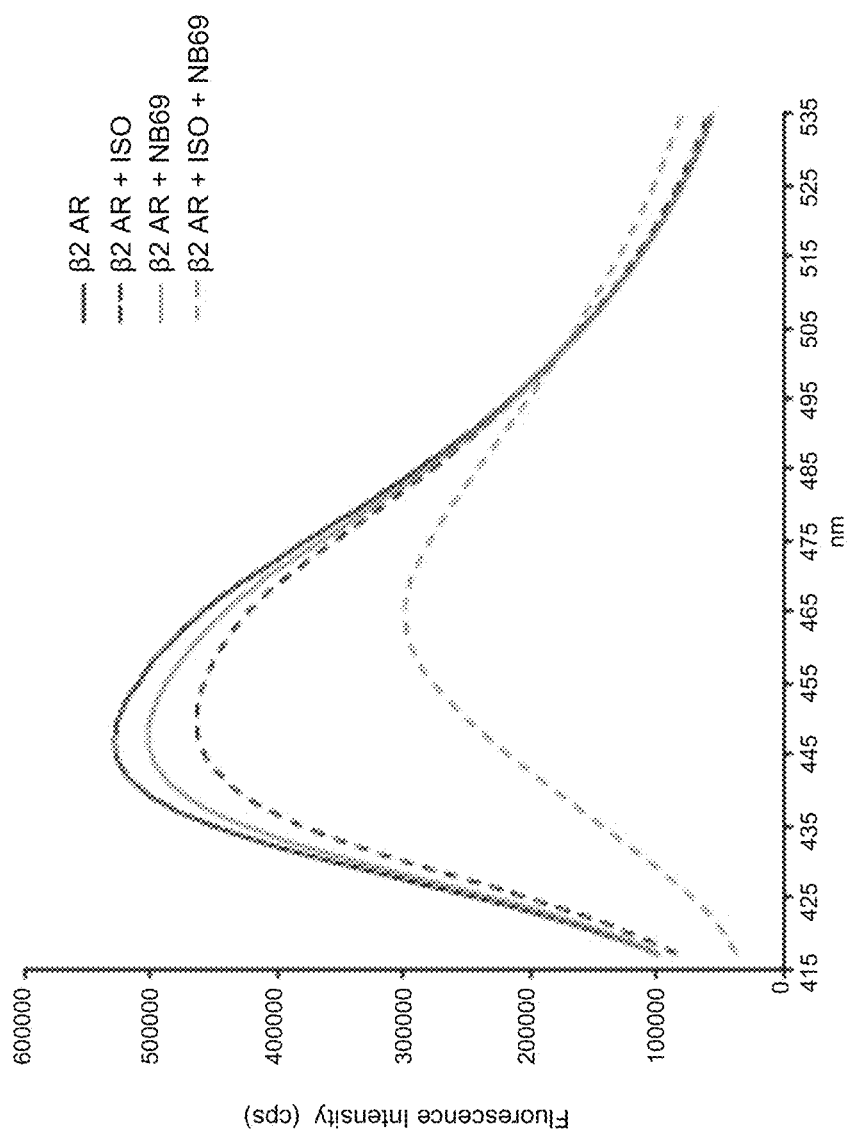
Figure 5D:
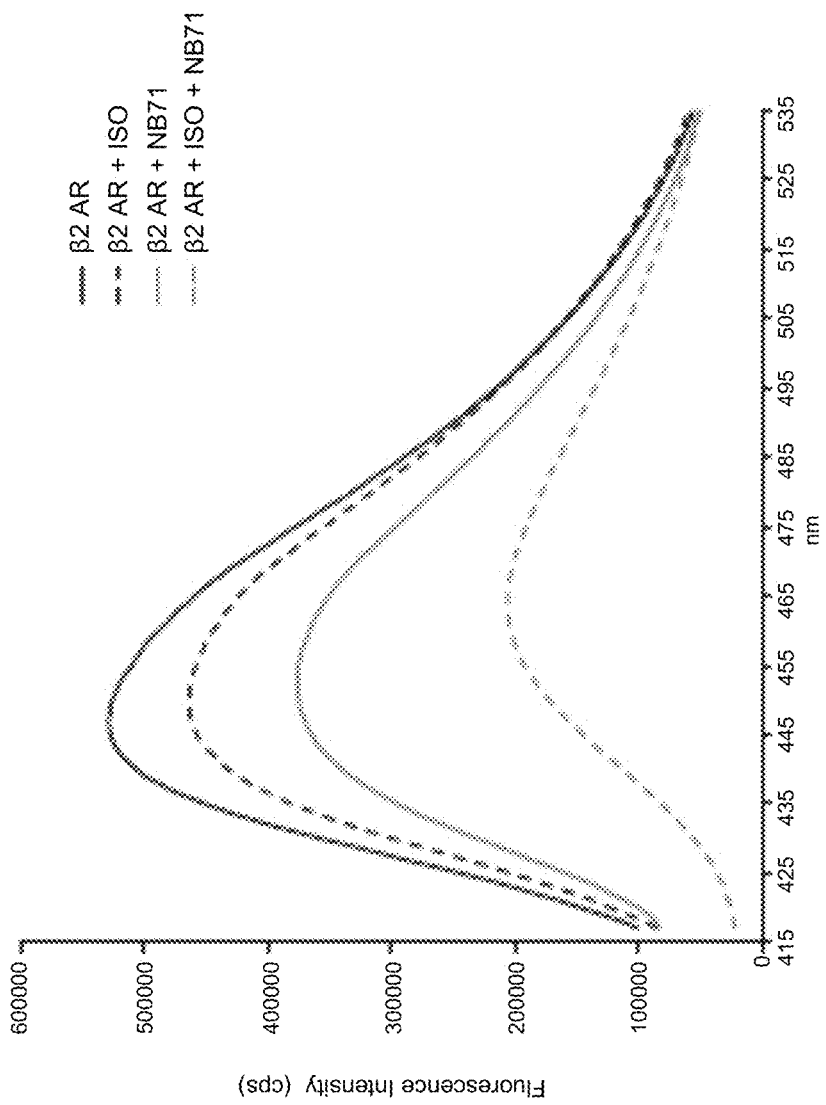
Figure 5E:
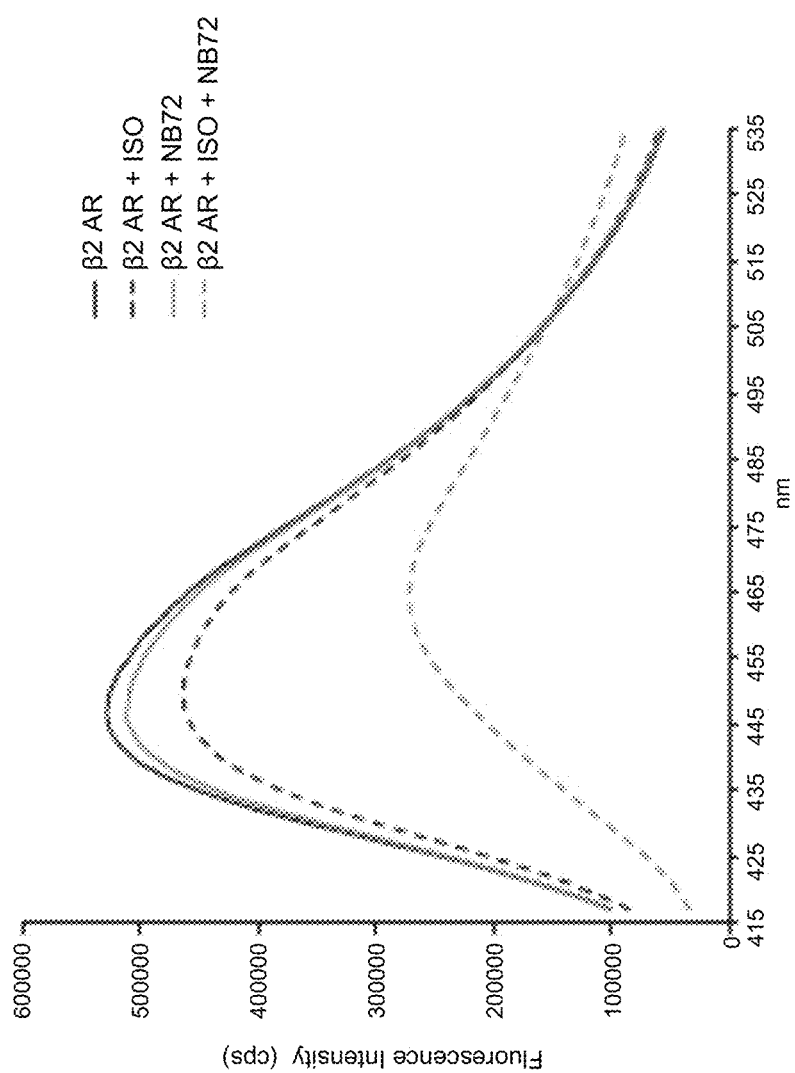
Figure 5F:
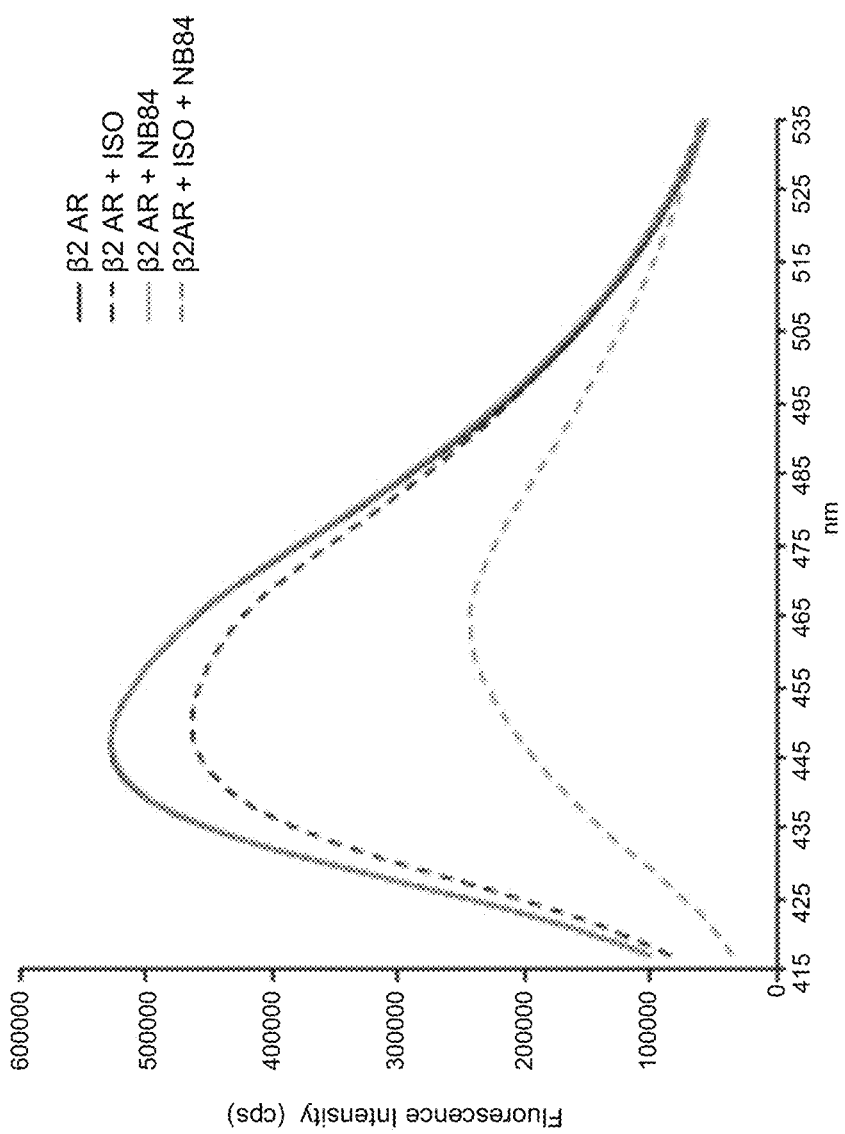

FIG. 4. Selective binding of nanobodies to the active state of the receptor: Purified $\beta_2AR$ (20 μM) bound to an agonist was incubated with and without 40 μM nanobodies (black and blue, respectively) for two hours at room temperature prior to analyzing by size exclusion chromatography.

FIGS. 5A-5F. Fluorescence emission spectra showing nanobody-induced conformational changes of monobromobimane-labeled $\beta_2AR$: Nanobodies that increase agonist binding affinity for the $\beta_2AR$ stabilize an active state of the receptor. A fluorescence-based functional assay using monobromobimane- (mBBr-) labeled purified receptor shows that 1 μM of nanobodies 65, 67, 69, 71, 72 and 84 (red) stabilize a more active state of the $\beta_2AR$ (bound to the full agonist isoproterenol) when compared with receptor in the absence of nanobodies (black). This active state is characterized by a quenching of mBBr fluorescence and a redshift in mBBr fluorescence (Yao et al. 2009).

Figure 6:
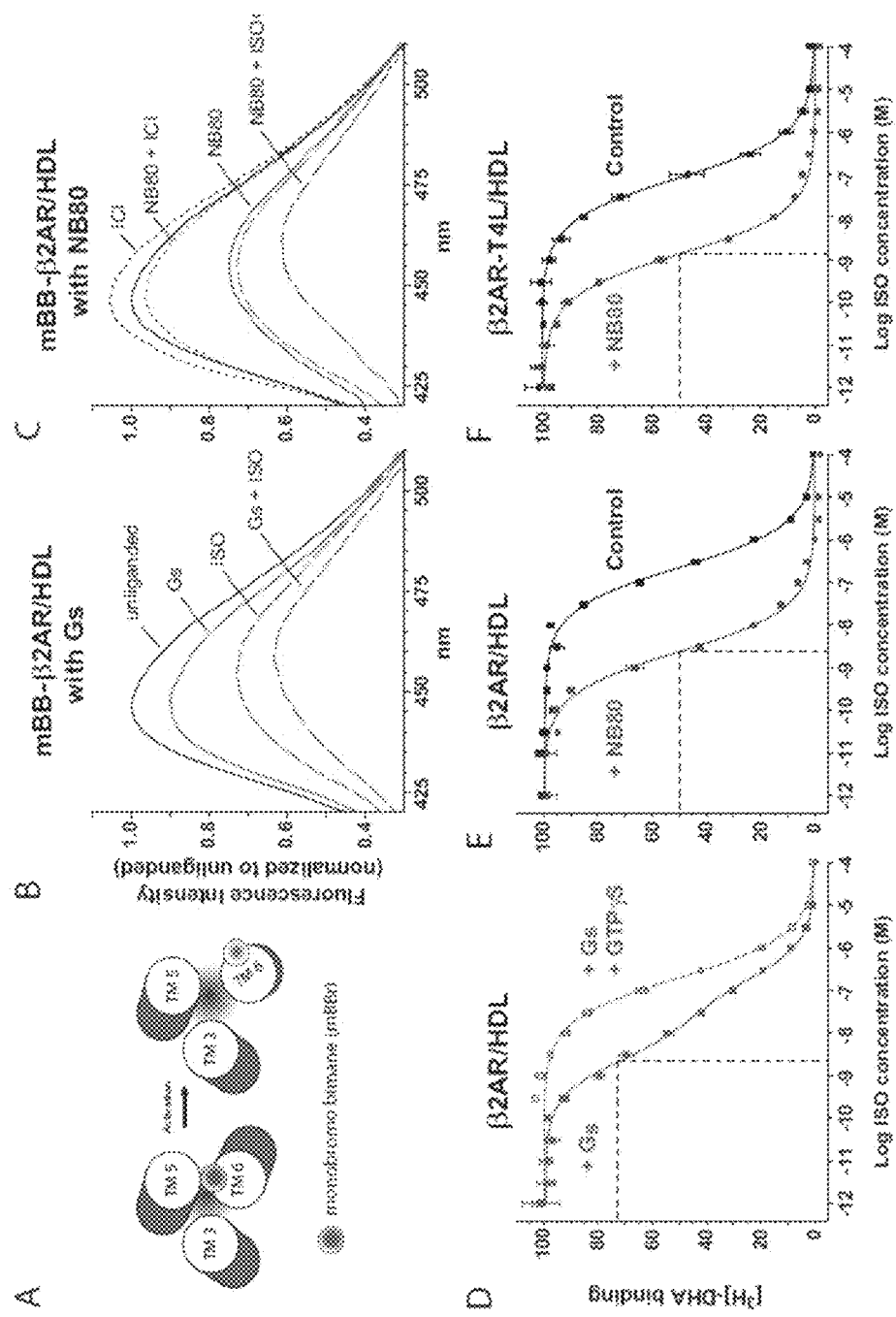

FIG. 6. Effect of Nb80 on $\beta_2AR$ structure and function:

Panel A: The cartoon illustrates the movement of the environmentally sensitive bimane probe attached to $Cys265^{6.27}$ in the cytoplasmic end of TM6 from a more buried, hydrophobic environment to a more polar, solvent-exposed position during receptor activation that results in a decrease in the observed fluorescence in FIG. 6, Panels B and C.

Panels B and C: Fluorescence emission spectra showing ligand-induced conformational changes of monobromobimane-labeled $\beta_2AR$ reconstituted into high density lipoprotein particles (mBB-$\beta_2AR$/HDL) in the absence (black solid line) or presence of full agonist isoproterenol (ISO, green wide dashed line), inverse agonist ICI-118,551 (ICI, black dashed line), $G_s$ heterotrimer (red solid line), nanobody-80 (Nb80, blue solid lines), and combinations of $G_s$ with ISO (red wide dashed line), Nb80 with ISO (blue wide dashed line), and Nb80 with ICI (blue dashed line).

Panels D through F: Ligand binding curves for ISO competing against [$^3$H]-dihydroalprenolol ([$^3$H]-DHA) for Panel D, $\beta_2AR$/HDL reconstituted with $G_s$ heterotrimer in the absence or presence GTPγS, Panel E, $\beta_2AR$/HDL in the absence and presence of Nb80, and Panel F, $\beta_2AR$-T4L/HDL in the absence and presence of Nb80. Error bars represent standard errors.

Figure 7:
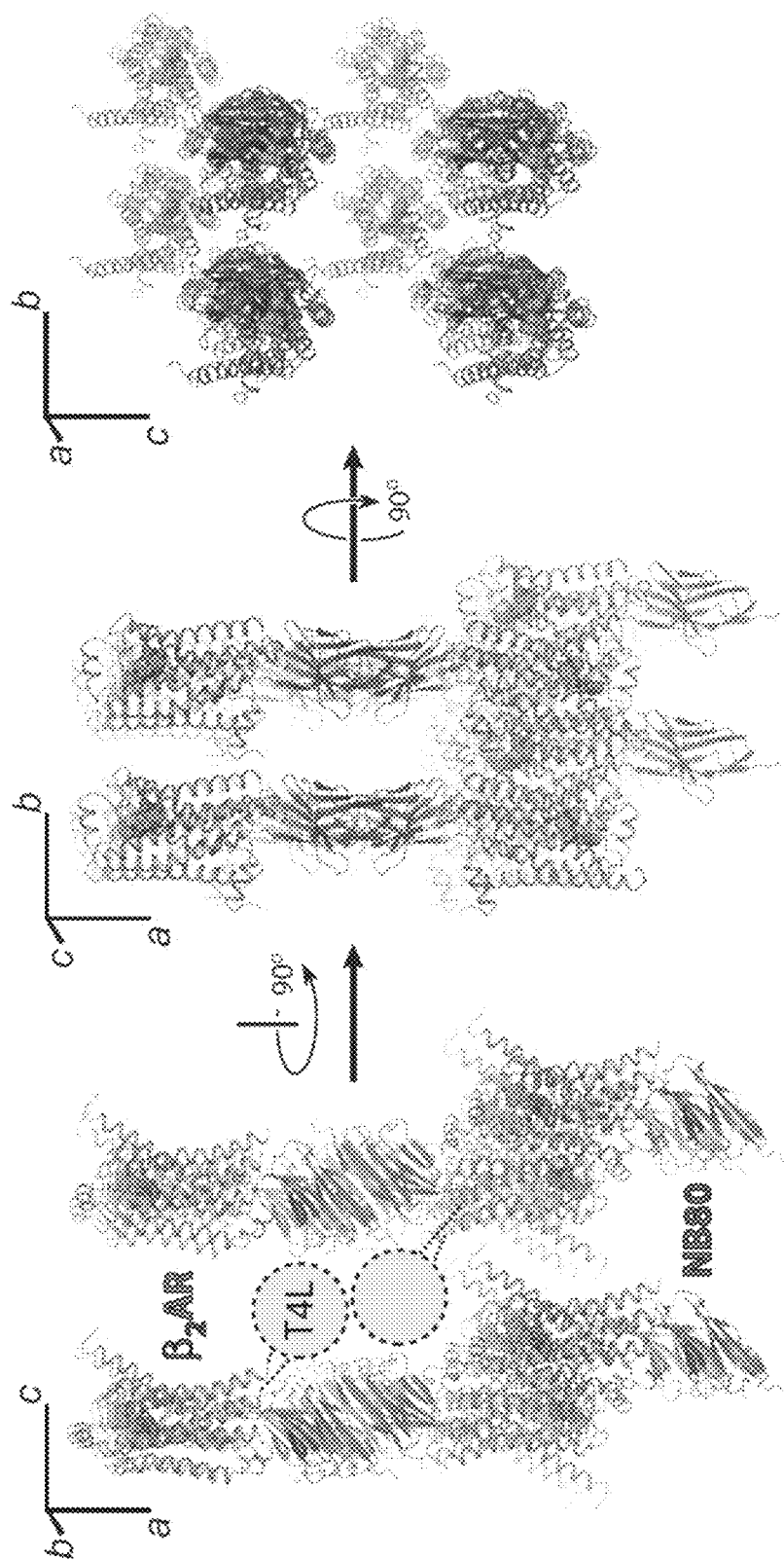

FIG. 7. Packing of the agonist-$\beta_2AR$-T4L-Nb80 complex in crystals formed in lipidic cubic phase: Three different views of the structure of $\beta_2AR$ indicated in orange, Nb80 in blue, and agonist in green. T4 lysozyme (T4L) could not be modeled due to poor electron density; its likely position is indicated by the light blue circle with black dashed lines connected to the intracellular ends of TM5 and TM6 where it is fused in the $\beta_2AR$-T4L construct. PyMOL (http://www.pymol.org) was used for the preparation of all figures.

Figure 8:
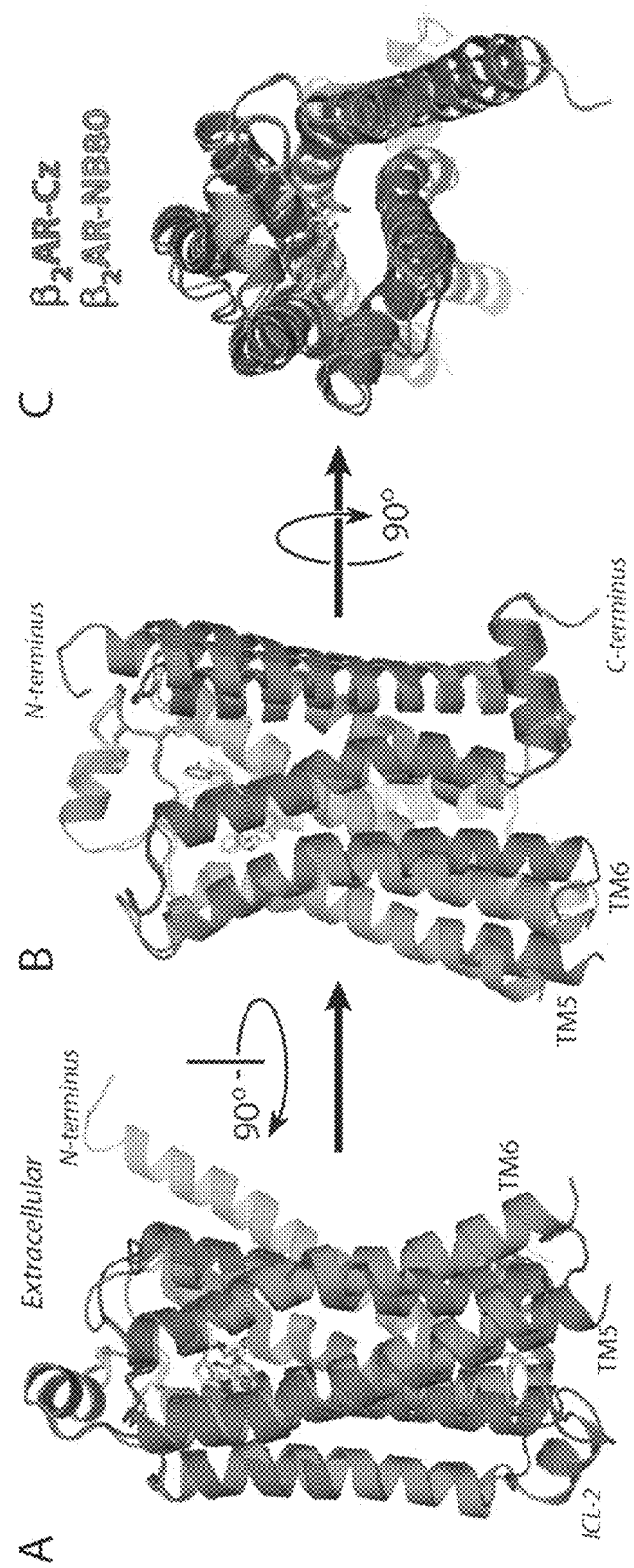

FIG. 8. Comparison of the inverse agonist and agonist-Nb80 stabilized crystal structures of the $\beta_2AR$: The structure of inverse agonist carazolol-bound $\beta_2AR$-T4L ($\beta_2AR$-Cz) is shown in blue with the carazolol in yellow. The structure of agonist bound and Nb80 stabilized $\beta_2AR$-T4L ($\beta_2AR$-Nb80) is shown in orange with agonist in green. These two structures were aligned using Pymol align function.

Panel A: Side view of the superimposed structures showing significant structural changes in the intracellular and G protein facing part of the receptors.

Panel B: Side view following 90 degrees rotation on the vertical axis.

Panel C: Comparison of the extracellular ligand binding domains showing modest structural changes.

Figure 9:
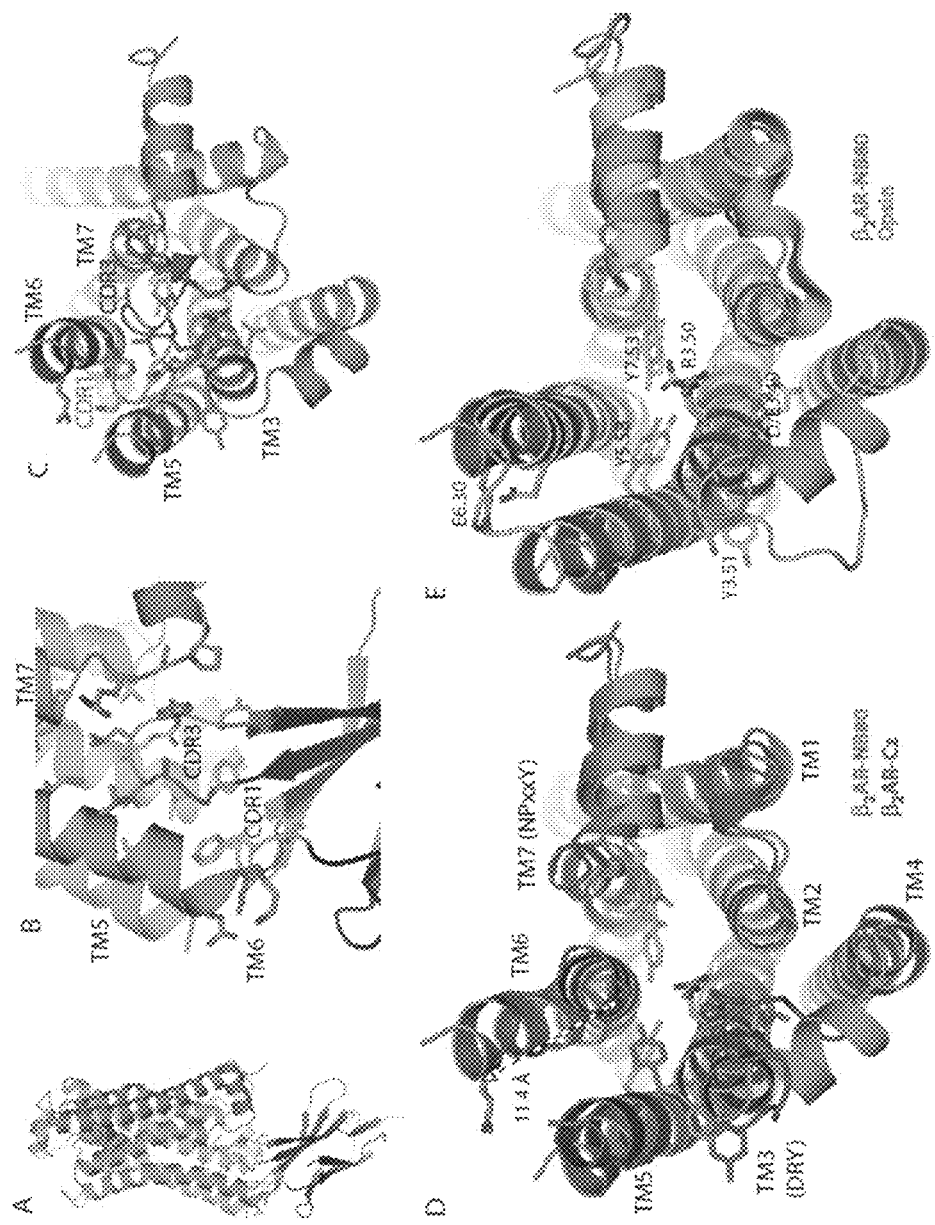

FIG. 9. Nb80 stabilized intracellular domain compared to inactive $\beta_2AR$ and opsin structures:

Panel A: Side view of $\beta_2AR$ (orange) with CDRs of Nb80 in light blue (CDR1) and blue (CDR3) interacting with the receptor.

Panel B: Closer view focusing on CDRs 1 and 3 entering the $\beta_2AR$. Side chains in TM3, 5, 6, and 7 within 4 Å of the CDRs are shown. The larger CDR3 penetrates 13 Å into the receptor.

Panel C: Interaction of CDR1 and CDR3 viewed from the intracellular side.

Panel D: The agonist bound and Nb80 stabilized $\beta_2AR$-T4L ($\beta_2AR$-Nb80) is superimposed with the carazolol-bound inactive structure of $\beta_2AR$-T4L ($\beta_2AR$-Cz). The ionic lock interaction between Asp3.49 and Arg3.50 of the DRY motif in TM3 is broken in the $\beta_2AR$-Nb80 structure. The intracellular end of TM6 is moved outward and away from the core of the receptor. The arrow indicates a 11.4 Å change in distance between the α-carbon of Glu6.30 in the structures of $\beta_2AR$-Cz and $\beta_2AR$-Nb80. The intracellular ends of TM3 and TM7 move toward the core by 4 Å and 2.5 Å, respectively, while TM5 moves outward by 6 Å.

Panel E: The $\beta_2AR$-Nb80 structure superimposed with the structure of opsin crystallized with the C-terminal peptide of $G_t$ (transducin).

Figure 10:
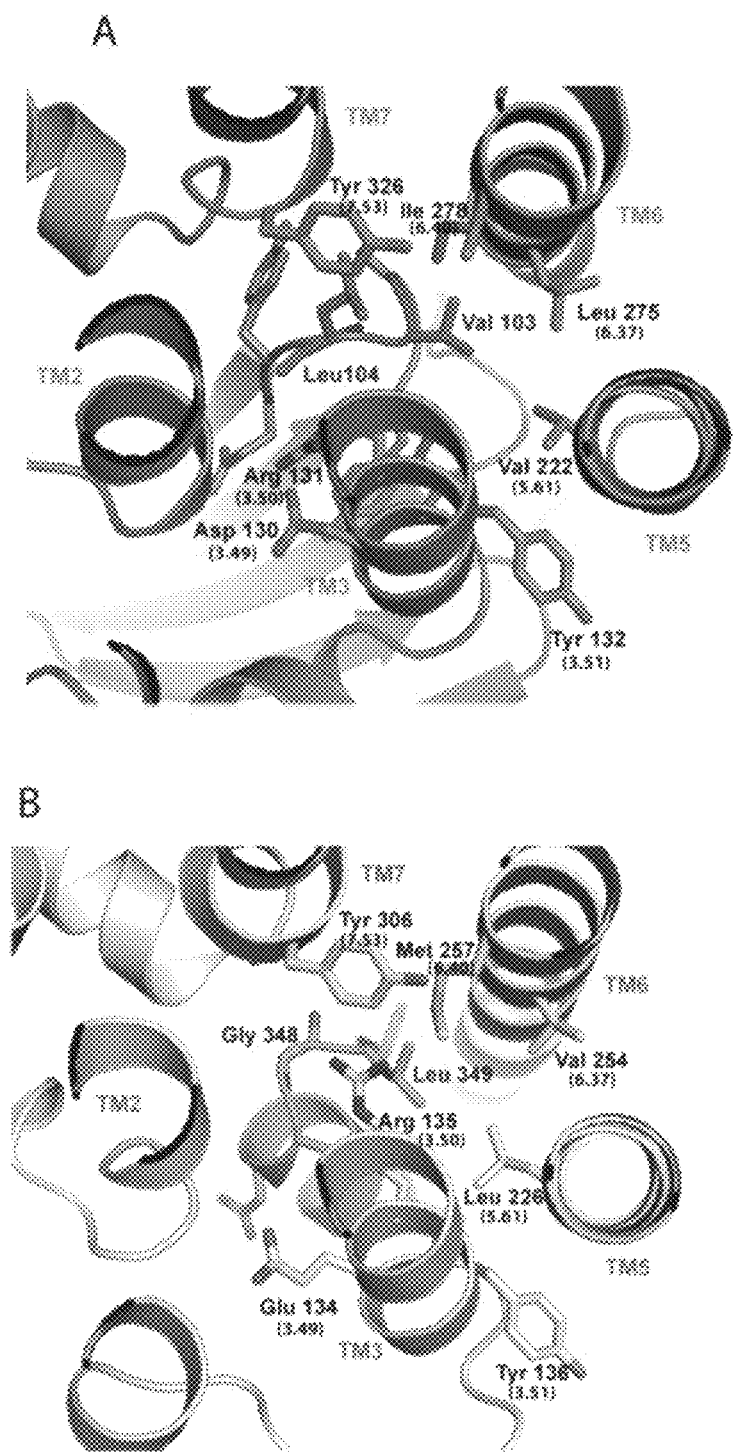

FIG. 10. Nb80 stabilized intracellular domain of $\beta_2AR$ compared to opsin structures:

Panel A: Interactions between the $\beta_2AR$ and Nb80.

Panel B: Interactions between opsin and the carboxyl terminal peptide of transducin.

Figure 11:
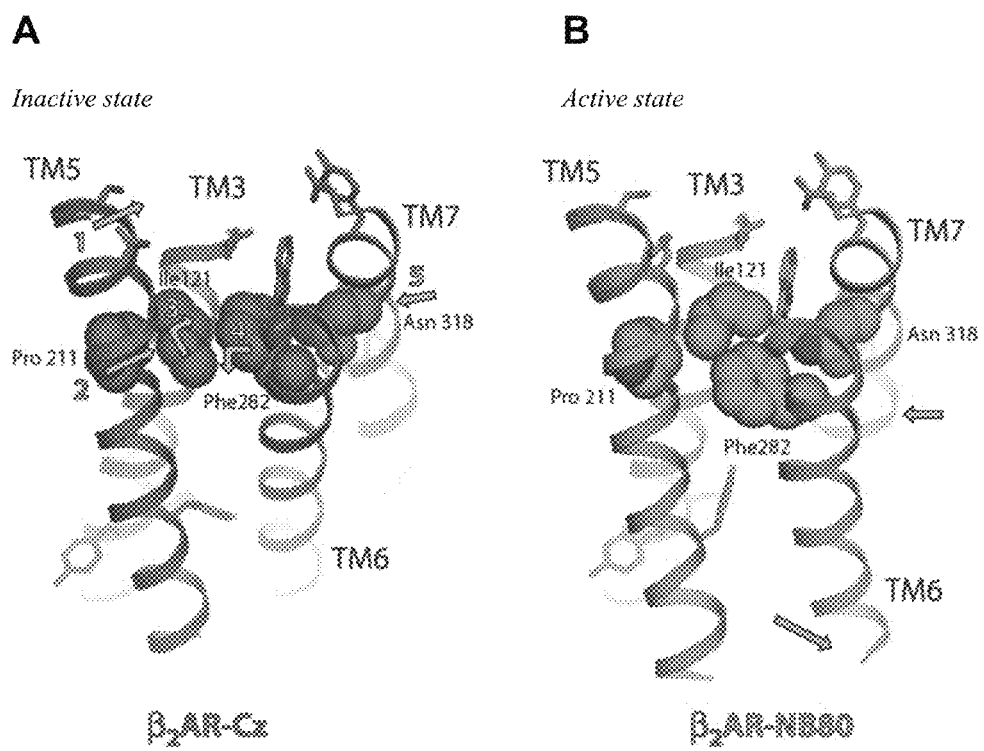

FIG. 11. Rearrangement of transmembrane segment packing interactions upon agonist binding:

Panel A: Packing interactions that stabilize the inactive state are observed between Pro211 in TM5, Ile121 in TM3, Phe282 in TM6 and Asn316 in TM5.

Panel B: The inward movement of TM5 upon agonist binding disrupts the packing of Ile121 and Pro211 resulting in a rearrangement of interactions between Ile121 and Phe282. These changes contribute to a rotation and outward movement of TM6 and an inward movement of TM7.

Figure 12:
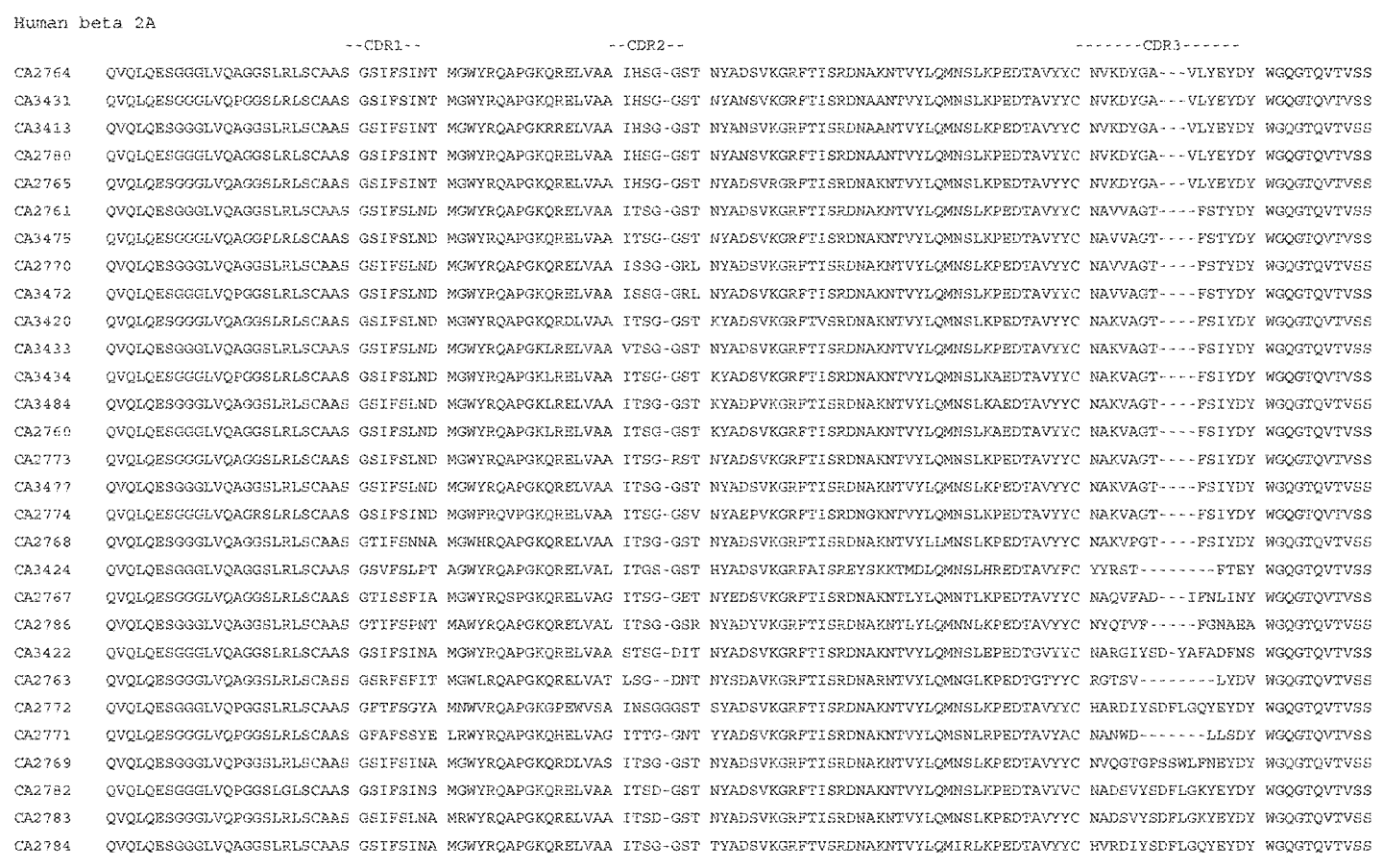

FIG. 12. Amino acid sequences of the different nanobodies raised against β$_2$AR: Sequences have been aligned using standard software tools. CDRs have been defined according to IMGT numbering (Lefranc et al. 2003).

Figure 13:
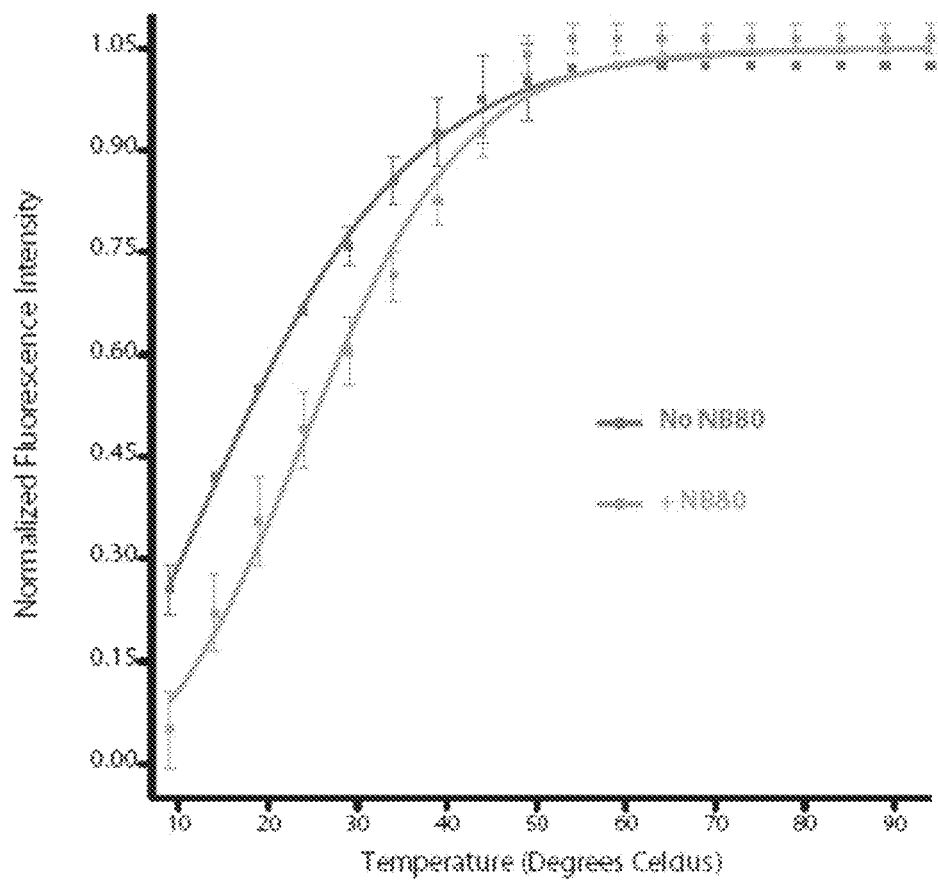

FIG. 13. Effect of Nb80 on the thermal stability of the β$_2$AR receptor: Comparison of the melting curves of detergent-solubilized (DDM) agonist-bound (isoproterenol) β$_2$AR in the presence and absence of Nb80. The apparent melting temperature for β$_2$AR without Nb80 is 12.0° C. The apparent melting temperature for β$_2$AR with Nb80 is 24° C.

Figure 14A:
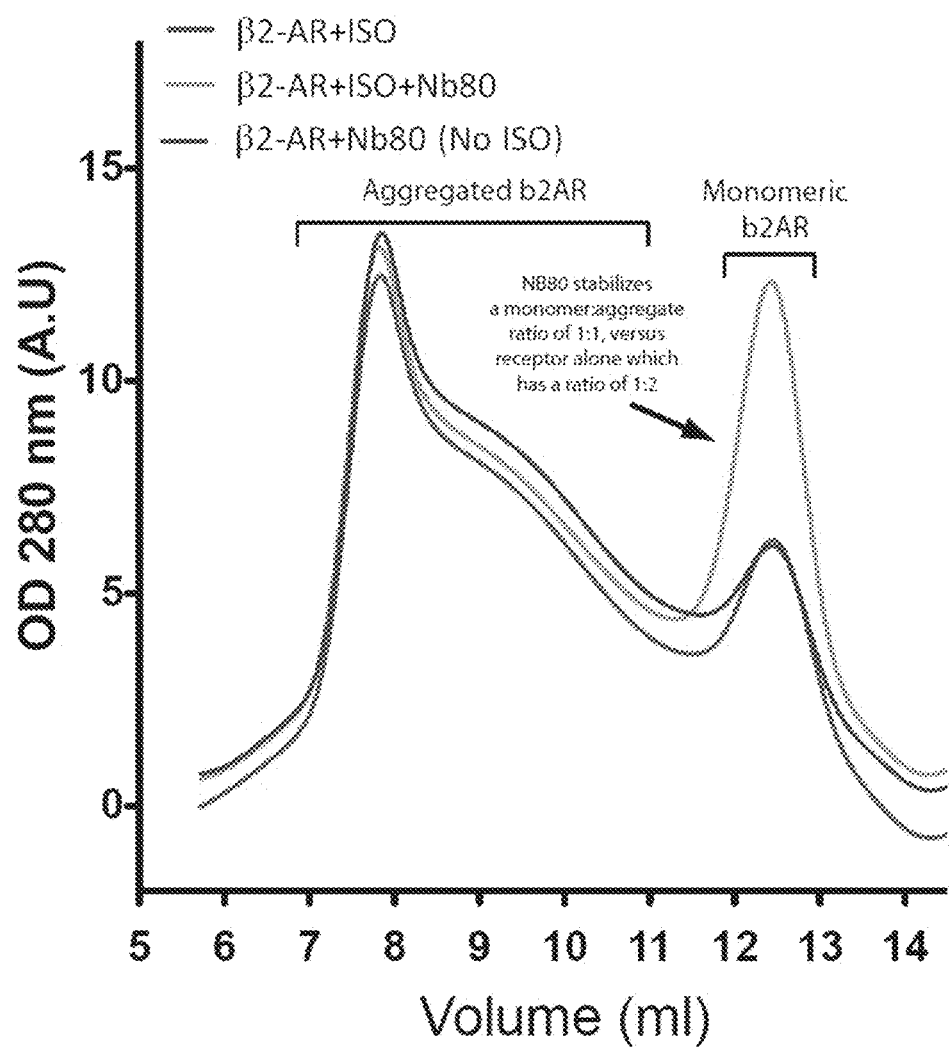
Figure 14B:
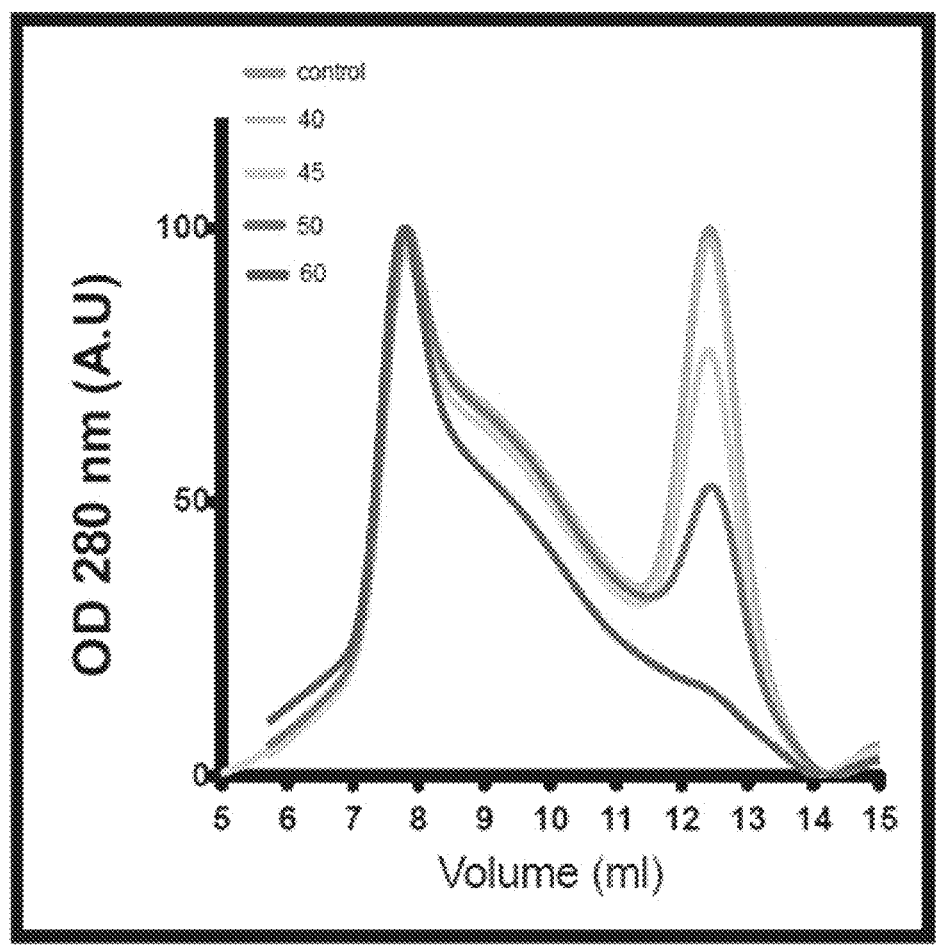

FIGS. 14A and 14B. Effect of Nb80 on the temperature-induced aggregation of the β$_2$AR receptor:

FIG. 14A: Detergent-solubilized (DDM) β$_2$AR was heated for ten minutes at 50° C. in the presence of Nb80 or isoproterenol and the aggregation of the receptor was analyzed by SEC.

FIG. 14B: Temperature dependence of the isoproterenol-bound receptor in the absence of Nb80.

Figure 15:
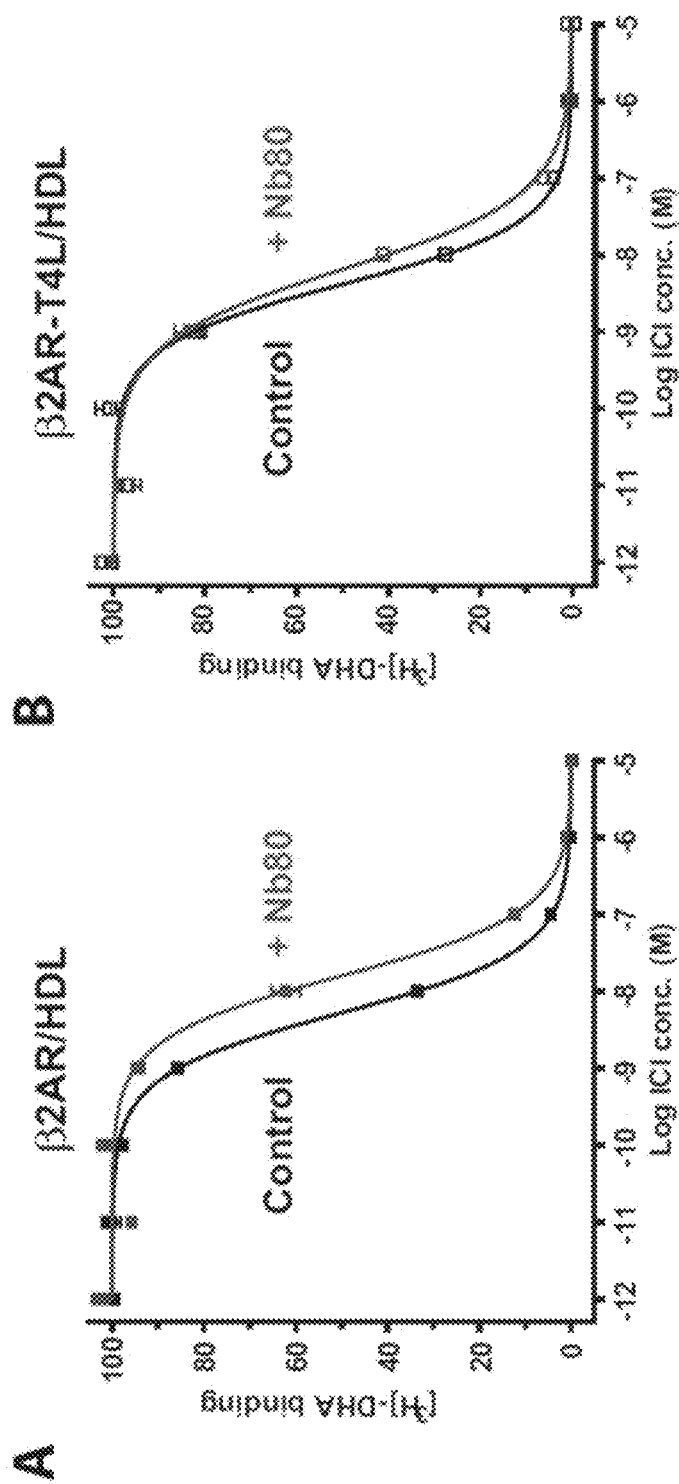

FIG. 15. Nb80 has little effect on β$_2$AR binding to the inverse agonist ICI-118,551: β$_2$AR (Panel A) or β$_2$AR-T4L (Panel B) was reconstituted into HDL particles and agonist competition binding experiments were performed in the absence or presence of Nb80. Ligand binding curves for the inverse agonist ICI-118551 competing against [$^3$H]-dihydroalprenolol ([3H]-DHA) for a, β$_2$AR/HDL in the absence and presence of Nb80, and b, β$_2$AR-T4L/HDL in the absence and presence of Nb80.

Figure 16A:
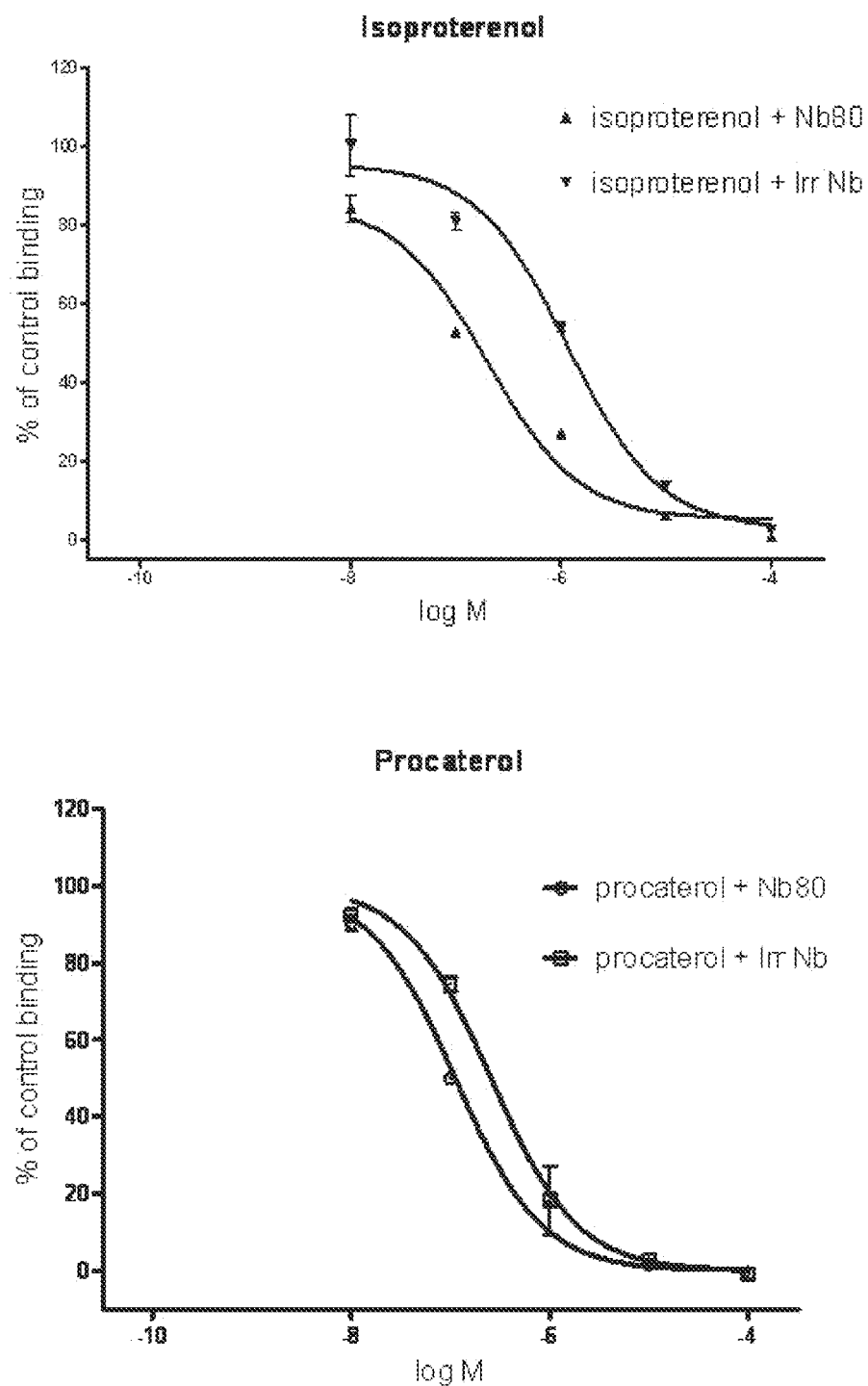

FIGS. 16A and 16B. Nb80 increases β$_2$AR affinity for agonists but not for antagonists: Competitive ligand binding experiments were performed on commercial insect cell-derived membranes containing full-length β$_2$AR in the absence or presence of Nb80. Dose-dependent radio-ligand displacement curves in presence of Nb80 and an irrelevant Nanobody (Irr Nb) for two representative agonists (isoproterenol, procaterol) and two representative antagonists (ICI-118,551 and carvedilol).

FIG. 17. Sequence alignment of human β$_1$AR and human β$_2$AR: Amino acids of the β$_2$-adrenoreceptor that interact with Nb80 in the β$_2$AR-Nb80 interface are underlined.

FIGS. 18A-18D. Nb80 selectively binds the active conformation of the human β$_1$AR receptor: Ligand binding curves for agonists and inverse agonists competing against [$^3$H]-dihydroalprenolol ([$^3$H]-DHA).

Figure 18A:
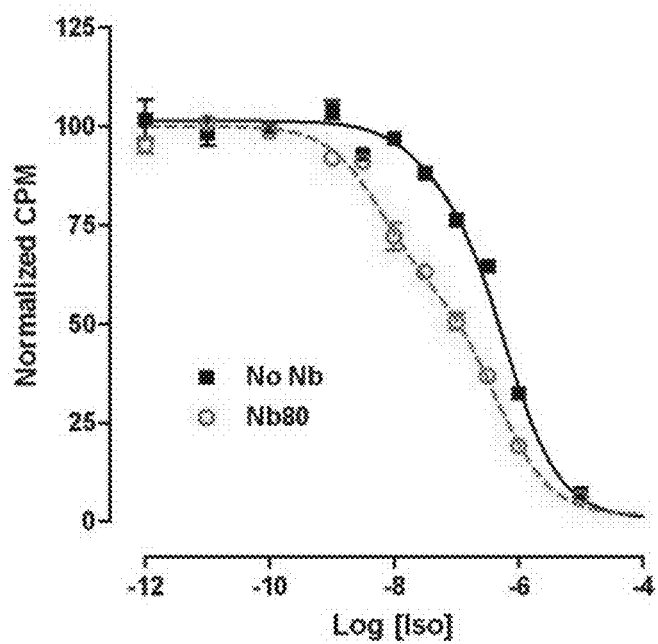

FIG. 18A: Agonist Isoproterenol (ISO) binding to β$_2$AR in the presence and absence of Nb80.

Figure 18B:
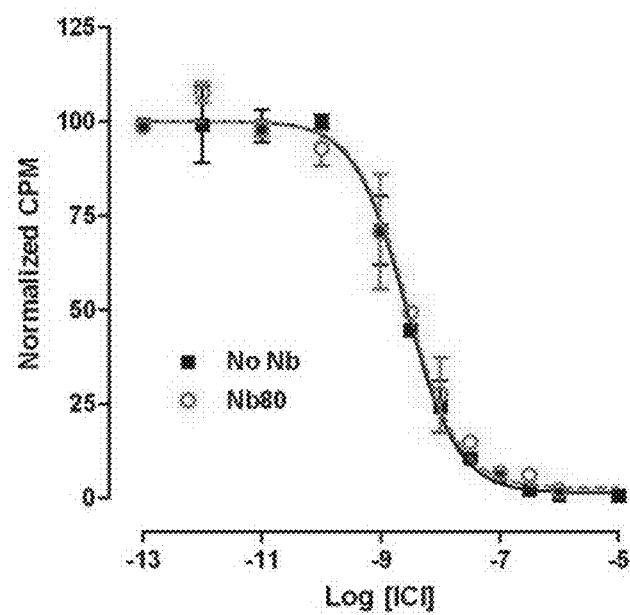

FIG. 18B: Inverse agonist ICI-118,551 (ICI) binding to β$_2$AR in the presence and absence of Nb80.

Figure 18C:
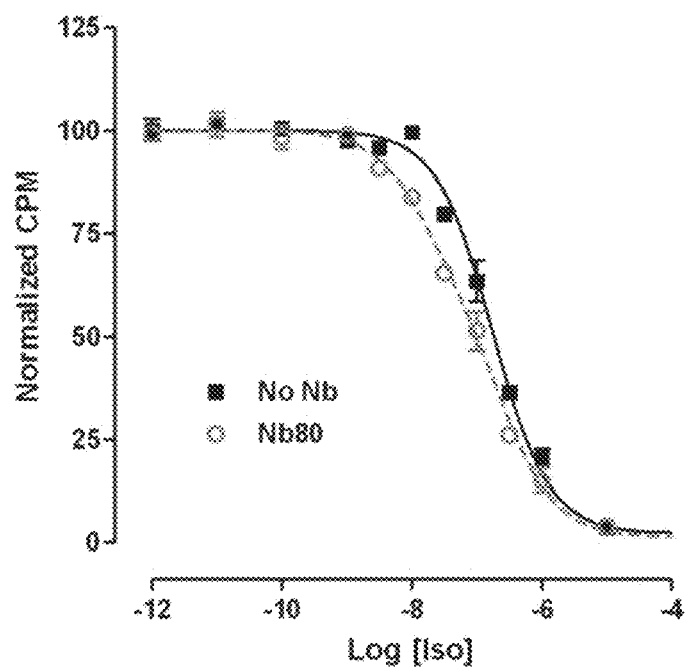

FIG. 18C: Agonist Isoproterenol (ISO) binding to β$_1$AR in the presence and absence of Nb80.

Figure 18D:
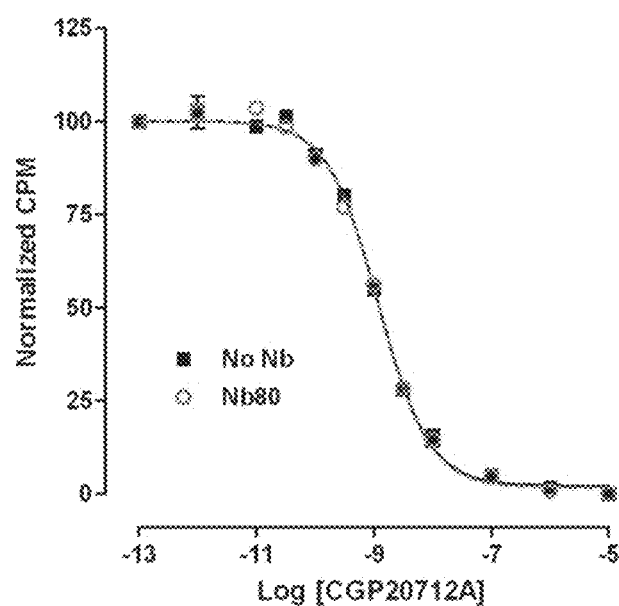

FIG. 18D: Inverse agonist CGP20712A (CPG) binding to β$_1$AR in the presence and absence of Nb80.

DETAILED DESCRIPTION

Definitions

The disclosure is described with respect to particular embodiments and with reference to certain drawings; the invention is not limited thereto, but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms "first," "second," "third," and the like in the description and in the claims, are used for distinguishing between similar elements and not necessarily for describing a sequential or chronological order. It is to be understood that the terms so used are interchangeable under appropriate circumstances and that the embodiments hereof described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, genetics and protein and nucleic acid chemistry and hybridization described herein, are those well known and commonly used in the art. The methods and techniques hereof are generally performed according to conventional methods well known in the art and as described in various general and more specific references that are cited and discussed throughout the present specification unless otherwise indicated. See, for example, Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002).

The term "protein binding domain" refers generally to any non-naturally occurring molecule or part thereof that is able to bind to a protein or peptide using specific intermolecular interactions. A variety of molecules can function as protein binding domains, including, but not limited to, proteinaceous molecules (protein, peptide, protein-like or protein containing), nucleic acid molecules (nucleic acid, nucleic acid-like, nucleic acid containing), and carbohydrate molecules (carbohydrate, carbohydrate-like, carbohydrate containing). A more detailed description can be found further in the specification.

As used herein, the terms "polypeptide," "protein," and "peptide" are used interchangeably herein, and refer to a polymeric form of amino acids of any length, which can include coded and non-coded amino acids, chemically or biochemically modified or derivatized amino acids, and polypeptides having modified peptide backbones.

As used herein, the terms "multiprotein complex" or "protein complex" or simply "complex" refer to a group of two or more associated polypeptide chains. Proteins in a protein complex are linked by non-covalent protein-protein interactions. The "quaternary structure" is the structural arrangement of the associated folded proteins in the protein complex. A "multimeric complex" refers to a protein complex as defined herein, which may further comprise a non-proteinaceous molecule.

As used herein, the terms "nucleic acid molecule," "polynucleotide," "polynucleic acid," and "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "ligand" or "receptor ligand" means a molecule that specifically binds to a GPCR, either intracellularly or extracellularly. A ligand may be, without the purpose of being limitative, a protein, a (poly)peptide, a lipid, a small molecule, a protein scaffold, a nucleic acid, an ion, a carbohydrate, an antibody or an antibody fragment, such as a nanobody (all as defined herein). A ligand may be a synthetic or naturally occurring. A ligand also includes a "native ligand," which is a ligand that is an endogenous, natural ligand for a native GPCR. A "modulator" is a ligand that increases or decreases the signaling activity of a GPCR (i.e., via an intracellular response) when it is in contact with, e.g., binds to, a GPCR that is expressed in a cell. This term includes agonists, full agonists, partial agonists, inverse agonists, and antagonists, of which a more detailed description can be found further in the specification.

The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three-dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, *Biophysical Chemistry, Part I: The Conformation of Biological Macromolecules*, W.H. Freeman and Company, 1980, and Creighton, *Proteins: Structures and Molecular Properties*, W.H. Freeman and Company, 1993. A "specific conformational state" is any subset of the range of conformations or conformational states that a protein may adopt.

A "functional conformation" or a "functional conformational state," as used herein, refers to the fact that proteins possess different conformational states having a dynamic range of activity, in particular, ranging from no activity to maximal activity. It should be clear that "a functional conformational state" is meant to cover any conformational state of a GPCR, having any activity, including no activity; and is not meant to cover the denatured states of proteins.

As used herein, the terms "complementarity-determining region" or "CDR" within the context of antibodies refer to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have three CDR regions, each non-contiguous with the others (termed L1, L2, L3, H1, H2, H3) for the respective light (L) and heavy (H) chains. Nanobodies, in particular, generally comprise a single amino acid chain that can be considered to comprise four "framework sequences or regions" or FRs and three complementarity-determining regions" or CDRs. The nanobodies have three CDR regions, each non-contiguous with the others (termed CDR1, CDR2, CDR3). The delineation of the FR and CDR sequences is based on the IMGT unique numbering system for V-domains and V-like domains (Lefranc et al. 2003).

An "epitope," as used herein, refers to an antigenic determinant of a polypeptide. An epitope could comprise three amino acids in a spatial conformation, which is unique to the epitope. Generally an epitope consists of at least 4, 5, 6, or 7 such amino acids, and more usually, consists of at least 8, 9, or 10 such amino acids. Methods of determining the spatial conformation of amino acids are known in the art and include, for example, x-ray crystallography and two-dimensional nuclear magnetic resonance.

A "conformational epitope," as used herein, refers to an epitope comprising amino acids in a spatial conformation that is unique to a folded three-dimensional conformation of the polypeptide. Generally, a conformational epitope consists of amino acids that are discontinuous in the linear sequence that come together in the folded structure of the protein. However, a conformational epitope may also consist of a linear sequence of amino acids that adopts a conformation that is unique to a folded three-dimensional conformation of the polypeptide (and not present in a denatured state). In multiprotein complexes, conformational epitopes consist of amino acids that are discontinuous in the linear sequences of one or more polypeptides that come together upon folding of the different folded polypeptides and their association in a unique quaternary structure. Similarly, conformational epitopes may here also consist of a linear sequence of amino acids of one or more polypeptides that come together and adopt a conformation that is unique to the quaternary structure.

The term "specificity," as used herein, refers to the ability of a protein binding domain, in particular, an immunoglobulin or an immunoglobulin fragment, such as a nanobody, to bind preferentially to one antigen versus a different antigen, and does not necessarily imply high affinity.

The term "affinity," as used herein, refers to the degree to which a protein binding domain, in particular, an immunoglobulin such as an antibody, or an immunoglobulin fragment such as a nanobody, binds to an antigen so as to shift the equilibrium of antigen and protein binding domain toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M; more preferably, lower than $10^{-7}$ M. Most preferably, the dissociation constant is lower than $10^{-8}$M.

The terms "specifically bind" and "specific binding," as used herein, generally refers to the ability of a protein binding domain, in particular, an immunoglobulin such as an antibody, or an immunoglobulin fragment such as a nanobody, to preferentially bind to a particular antigen that is present in a homogeneous mixture of different antigens. In certain embodiments, a specific binding interaction will discriminate between desirable and undesirable antigens in a sample, in some embodiments more than about ten- to 100-fold or more (e.g., more than about 1000- or 10,000-fold). Within the context of the spectrum of conformational states of GPCRs, the terms particularly refer to the ability of a protein binding domain (as defined herein) to preferentially recognize and/or bind to a particular conformational state of a GPCR as compared to another conformational state. For example, an active state-selective protein binding domain will preferentially bind to a GPCR in an active conformational state and will not, or to a lesser degree, bind to a GPCR in an inactive conformational state, and will thus have a higher affinity for the active conformational state. The terms "specifically bind," "selectively bind," "preferentially bind," and grammatical equivalents thereof, are used interchangeably herein. The terms "conformational specific" or "conformational selective" are also used interchangeably herein.

An "antigen," as used herein, means a molecule capable of eliciting an immune response in an animal. Within the context of the spectrum of conformational states of GPCR, the molecule comprises a conformational epitope of a GPCR in a particular conformational state that is not formed or less accessible in another conformational state of the GPCR.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about two, about five, about ten, up to about twenty, up to about thirty, or up to about fifty or more amino acids. A protein or a fragment thereof may contain more than one deletion. Within the context of a GPCR, a deletion may also be a loop deletion, or an N- and/or C-terminal deletion.

An "insertion" or "addition" is that change in an amino acid or nucleotide sequence that has resulted in the addition of one or more amino acid or nucleotide residues, respectively, as compared to an amino acid sequence or nucleotide sequence of a parental protein. "Insertion" generally refers to addition of one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about one, about three, about five, about ten, up to about twenty, up to about thirty, or up to about fifty or more amino acids. A protein or fragment thereof may contain more than one insertion.

A "substitution," as used herein, results from the replacement of one or more amino acids or nucleotides by different amino acids or nucleotides, respectively, as compared to an amino acid sequence or nucleotide sequence of a parental protein or a fragment thereof. It is understood that a protein or a fragment thereof may have conservative amino acid substitutions that have substantially no effect on the protein's activity. By "conservative substitutions" is intended combinations such as gly, ala; val, ile, leu, met; asp, glu; asn, gln; ser, thr; lys, arg; cys, met; and phe, tyr, trp.

"Crystal" or "crystalline structure," as used herein, refers to a solid material, whose constituent atoms, molecules, or ions are arranged in an orderly repeating pattern extending in all three spatial dimensions. The process of forming a crystalline structure from a fluid or from materials dissolved in the fluid is often referred to as "crystallization" or "crystallogenesis." Protein crystals are almost always grown in solution. The most common approach is to lower the solubility of its component molecules gradually. Crystal growth in solution is characterized by two steps: nucleation of a microscopic crystallite (possibly having only 100 molecules), followed by growth of that crystallite, ideally to a diffraction-quality crystal.

"X-ray crystallography," as used herein, is a method of determining the arrangement of atoms within a crystal, in which a beam of X-rays strikes a crystal and diffracts into many specific directions. From the angles and intensities of these diffracted beams, a crystallographer can produce a three-dimensional picture of the density of electrons within the crystal. From this electron density, the mean positions of the atoms in the crystal can be determined, as well as their chemical bonds, their disorder and various other information.

The term "atomic coordinates," as used herein, refers to a set of three-dimensional coordinates for atoms within a molecular structure. In one embodiment, atomic coordinates are obtained using X-ray crystallography according to methods well known to those of ordinary skill in the art of biophysics. Briefly described, X-ray diffraction patterns can be obtained by diffracting X-rays off a crystal. The diffraction data are used to calculate an electron density map of the unit cell comprising the crystal; the maps are used to establish the positions of the atoms (i.e., the atomic coordinates) within the unit cell. Those skilled in the art understand that a set of structure coordinates determined by X-ray crystallography contains standard errors. In other embodiments, atomic coordinates can be obtained using other experimental biophysical structure determination methods that can include electron diffraction (also known as electron crystallography) and nuclear magnetic resonance (NMR) methods. In yet other embodiments, atomic coordinates can be obtained using molecular modeling tools, which can be based on one or more of ab initio protein folding algorithms, energy minimization, and homology-based modeling. These techniques are well known to persons of ordinary skill in the biophysical and bioinformatic arts.

"Solving the structure," as used herein, refers to determining the arrangement of atoms or the atomic coordinates of a protein, and is often done by a biophysical method, such as X-ray crystallography.

The term "compound" or "test compound" or "candidate compound" or "drug candidate compound," as used herein, describes any molecule, either naturally occurring or synthetic that is tested in an assay, such as a screening assay or drug discovery assay. As such, these compounds comprise organic or inorganic compounds. The compounds include polynucleotides, lipids or hormone analogs that are characterized by low molecular weights. Other biopolymeric organic test compounds include small peptides or peptide-like molecules (peptidomimetics) comprising from about two to about forty amino acids and larger polypeptides comprising from about forty to about five hundred amino acids, such as antibodies, antibody fragments or antibody conjugates. Test compounds can also be protein scaffolds. For high-throughput purposes, test compound libraries may be used, such as combinatorial or randomized libraries that provide a sufficient range of diversity. Examples include, but are not limited to, natural compound libraries, allosteric compound libraries, peptide libraries, antibody fragment libraries, synthetic compound libraries, fragment-based libraries, phage-display libraries, and the like. A more detailed description can be found further in the specification.

As used herein, the terms "determining," "measuring," "assessing," "monitoring" and "assaying" are used interchangeably and include both quantitative and qualitative determinations.

The term "biologically active," with respect to a GPCR, refers to a GPCR having a biochemical function (e.g., a binding function, a signal transduction function, or an ability to change conformation as a result of ligand binding) of a naturally occurring GPCR.

The terms "therapeutically effective amount," "therapeutically effective dose" and "effective amount," as used herein, mean the amount needed to achieve the desired result or results.

The term "pharmaceutically acceptable," as used herein, means a material that is not biologically or otherwise undesirable, i.e., the material may be administered to an individual along with the compound without causing any undesirable biological effects or interacting in a deleterious manner with any of the other components of the pharmaceutical composition in which it is contained.

DESCRIPTION

Structural information on GPCRs will provide insight into the structural, functional and biochemical changes involved in signal transfer from the receptor to intracellular interacting proteins (G proteins, β-arrestins, etc.) and will delineate ways to interfere with these pharmacologically relevant interactions. Efforts to obtain and crystallize GPCRs are, therefore, of great importance. However, this is a particularly difficult endeavor due to the biochemical challenges in working with GPCRs and the inherent instability of these complexes in detergent solutions. Also, the intrinsic conformational flexibility of GPCRs complicates high-resolution structure analysis of GPCRs alone because growing diffraction-quality crystals require stable, conformationally homogenous proteins (Kobilka et al. 2007). Provided are new experimental and analytical tools to capture or "freeze" functional conformational states of a GPCR of interest, in particular, its active conformational state, allowing the structural and functional analysis of the GPCR, including high resolution structural analysis and many applications derived thereof.

Described herein is a protein binding domain that is capable of specifically binding to a functional conformational state of a GPCR.

The protein binding domain hereof can be any non-naturally occurring molecule or part thereof (as defined hereinbefore) that is capable of specifically binding to a functional conformational state of a target GPCR. In one embodiment, the protein binding domains as described herein are protein scaffolds. The term "protein scaffold" refers generally to folding units that form structures, particularly protein or peptide structures, that comprise frameworks for the binding of another molecule, for instance, a protein (see, e.g., J. Skerra, 2000, for review). A protein binding domain can be derived from a naturally occurring molecule, e.g., from components of the innate or adaptive immune system, or it can be entirely artificially designed. A protein binding domain can be immunoglobulin-based or it can be based on domains present in proteins including, but limited to, microbial proteins, protease inhibitors, toxins, fibronectin, lipocalins, single chain antiparallel coiled coil proteins or repeat motif proteins. Examples of protein binding domains that are known in the art include, but are not limited to: antibodies, heavy chain antibodies (hcAb), single domain antibodies (sdAb), minibodies, the variable domain derived from camelid heavy chain antibodies (VHH or nanobodies), the variable domain of the new antigen receptors derived from shark antibodies (VNAR), alphabodies, protein A, protein G, designed ankyrin-repeat domains (DARPins), fibronectin type III repeats, anticalins, knottins, engineered CH2 domains (nanoantibodies), peptides and proteins, lipopeptides (e.g., pepducins), DNA, and RNA (see, e.g., Gebauer & Skerra, 2009; Skerra, 2000; Starovasnik et al. 1997; Binz et al. 2004; Koide et al. 1998; Dimitrov, 2009; Nygren et al. 2008; WO2010066740). Frequently, when generating a particular type of protein binding domain using selection methods, combinatorial libraries comprising a consensus or framework sequence containing randomized potential interaction residues are used to screen for binding to a molecule of interest, such as a protein.

"G-protein-coupled receptors," or "GPCRs," as used herein, are polypeptides that share a common structural motif having seven regions of between 22 to 24 hydrophobic amino acids that form seven alpha helices, each of which spans the membrane. Each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. Any of these regions are readily identifiable by analysis of the primary amino acid sequence of a GPCR.

GPCR structure and classification is generally well known in the art and further discussion of GPCRs may be found in Probst et al. 1992, Marchese et al. 1994, Lagerström & Schiöth 2008, Rosenbaum et al. 2009, and the following books: Jurgen Wess (Ed), *Structure Function Analysis of G Protein-Coupled Receptors* published by Wiley-Liss (first edition; Oct. 15, 1999); Kevin R. Lynch (Ed), *Identification and Expression of G Protein-Coupled Receptors* published by John Wiley & Sons (March 1998); and Tatsuya Haga (Ed), *G Protein-Coupled Receptors*, published by CRC Press (Sep. 24, 1999); and Steve Watson (Ed) *G-Protein Linked Receptor Factsbook*, published by Academic Press (1st edition; 1994).

GPCRs can be grouped on the basis of sequence homology into several distinct families. Although all GPCRs have a similar architecture of seven membrane-spanning α-helices, the different families within this receptor class show no sequence homology to one another, thus suggesting that the similarity of their transmembrane domain structure might define common functional requirements. A comprehensive view of the GPCR repertoire was possible when the first draft of the human genome became available. Fredriksson and colleagues divided 802 human GPCRs into families on the basis of phylogenetic criteria. This showed that most of the human GPCRs can be found in five main families, termed Glutamate, Rhodopsin, Adhesion, Frizzled/Taste2 and Secretin (Fredriksson et al. 2003).

In a preferred embodiment hereof, the protein binding domain is directed against or is capable of specifically binding to a functional conformational state of a GPCR, wherein the GPCR is chosen from the group comprising a GPCR of the Glutamate family of GPCRs, a GPCR of the Rhodopsin family of GPCRs, a GPCR of the Adhesion family of GPCRs, a GPCR of the Frizzled/Taste2 family of GPCRs, and a GPCR of the Secretin family of GPCRs. Preferably, the GPCR is a mammalian protein, or a plant protein, or a microbial protein, or a viral protein, or an insect protein. Even more preferably, the GPCR is a human protein.

Members of the Rhodopsin family (corresponding to class A (Kolakowski, 1994) or Class 1 (Foord et al. (2005) in older classification systems) only have small extracellular loops and the interaction of the ligands occurs with residues within the transmembrane cleft. This is by far the largest group (>90% of the GPCRs) and contains receptors for odorants, small molecules such as catecholamines and amines, (neuro)peptides and glycoprotein hormones. Rhodopsin, a representative of this family, is the first GPCR for which the structure has been solved (Palczewski et al. 2000). $\beta_2$AR, the first receptor interacting with a diffusible ligand for which the structure has been solved (Rosenbaum et al. 2007) also belongs to this family. Based on Phylogenetic analysis, class B GPCRs or Class 2 (Foord et al. 2005) receptors have recently been subdivided into two families: adhesion and secretin (Fredriksson et al. 2003). Adhesion and secretin receptors are characterized by a relatively long amino terminal extracellular domain involved in ligand-binding. Little is known about the orientation of the transmembrane domains, but it is probably quite different from that of rhodopsin. Ligands for these GPCRs are hormones, such as glucagon, secretin, gonadotropin-releasing hormone and parathyroid hormone. The Glutamate family receptors (Class C or Class 3 receptors) also have a large extracellular domain, which functions like a "Venus fly trap" since it can open and close with the agonist bound inside. Family members are the metabotropic glutamate, the $Ca^{2+}$-sensing and the $\gamma$-aminobutyric acid (GABA)-B receptors.

GPCRs include, without limitation, serotonin olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, the protease-activated receptors, the rhodopsins and other G-protein-coupled seven transmembrane segment receptors. GPCRs also include these GPCR receptors associated with each other as homomeric or heteromeric dimers or as higher-order oligomers. The amino acid sequences (and the nucleotide sequences of the cDNAs that encode them) of GPCRs are readily available, for example by reference to GenBank (on the World Wide Web at ncbi.nlm.nih.gov/entrez).

According to a preferred embodiment, the GPCR is chosen from the group comprising the adrenergic receptors, preferably the $\alpha$-adrenergic receptors, such as the $\alpha_1$-adrenergic receptors and the $\alpha_2$-adrenergic receptors, and the $\beta$-adrenergic receptors, such as the $\beta_1$-adrenergic receptors, the $\beta_2$-adrenergic receptors and the $\beta_3$-adrenergic receptors; or from the group comprising the muscarinic receptors, preferably the $M_1$-muscarinic receptors, the $M_2$-muscarinic receptors, the $M_3$-muscarinic receptors, the $M_4$-muscarinic receptors and the $M_5$-muscarinic receptors; or from the group of the angiotensin receptors, preferably the angiotensin II type 1 receptor, the angiotensin II type 2 receptor and other atypical angiotensin II receptors; all of which are well known in the art.

A GPCR, as used herein, may be any naturally occurring or non-naturally occurring (i.e., altered by man) polypeptide. The term "naturally occurring" in reference to a GPCR means a GPCR that is naturally produced (for example and without limitation, by a mammal, more specifically by a human, or by a virus, or by a plant, or by an insect, amongst others). Such GPCRs are found in nature. The term "non-naturally occurring" in reference to a GPCR means a GPCR that is not naturally occurring. Wild-type GPCRs that have been made constitutively active through mutation, and variants of naturally occurring GPCRs are examples of non-naturally occurring GPCRs. Non-naturally occurring GPCR may have an amino acid sequence that is at least 80% identical to, at least 90% identical to, at least 95% identical to or at least 99% identical to, a naturally occurring GPCR. Taking the $\beta_2$-adrenergic receptor as a particular non-limiting example of a GPCR within the scope hereof, it should be clear from the above that in addition to the human $\beta_2$-adrenergic receptor (e.g., the sequence described by Genbank accession number NP 000015), the mouse $\beta_2$-adrenergic receptor (e.g., as described by Genbank accession no. NM 007420) or other mammalian $\beta_2$-adrenergic receptor may also be employed. In addition, the term is intended to encompass wild-type polymorphic variants and certain other active variants of the $\beta_2$-adrenergic receptor from a particular species. For example, a "human $\beta_2$-adrenergic receptor" has an amino acid sequence that is at least 95% identical to (e.g., at least 95% or at least 98% identical to) the naturally occurring "human $\beta_2$-adrenoreceptor" of Genbank accession number NP 000015.

Further, it will be appreciated that the disclosure also envisages GPCRs with a loop deletion, or an N- and/or C-terminal deletion, or a substitution, or an insertion or addition in relation to its amino acid or nucleotide sequence, or any combination thereof (as defined hereinbefore, and see also Example section). It is further expected that the protein binding domains hereof will generally be capable of binding to all naturally occurring or synthetic analogs, variants, mutants, or alleles of the GPCR.

Various methods may be used to determine specific binding between the protein binding domain and a target GPCR, including, for example, enzyme linked immunosorbent assays (ELISA), surface Plasmon resonance assays, phage display, and the like, which are common practice in the art, for example, and discussed in Sambrook et al. (2001), *Molecular Cloning, A Laboratory Manual*, Third Ed., Cold Spring Harbor Laboratory Press, Cold Spring Harbor, N.Y. It will be appreciated that for this purpose, a unique label or tag will often be used, such as a peptide label, a nucleic acid label, a chemical label, a fluorescent label, or a radio frequency tag, as described further herein.

It should be clear that GPCRs are conformationally complex membrane proteins that exhibit a spectrum-functional behavior in response to natural and synthetic ligands. Defining the pathway from agonist binding to protein activation will require a combination of crystal structures of different conformational states of the receptor under investigation in complex with various natural or synthetic ligands (including structures of active agonist-bound states and GPCR-G protein complexes), which will provide snapshots along the activation pathway.

Thus, in a preferred embodiment, the protein binding domain is capable of stabilizing or otherwise increasing the stability of a particular functional conformational state of a GPCR. Preferably, the protein binding domain is capable of inducing the formation of a functional conformational state in a GPCR upon binding the GPCR. The functional conformation state of the GPCR can be a basal conformational state, or an active conformational state or an inactive conformational state. Preferably, the protein binding domain is capable of stabilizing a GPCR in its active conformational state and/or is capable of forcing the GPCR to adopt its active conformational state upon binding.

The wording "inducing" or "forcing" or "locking" or "trapping" or "fixing" or "freezing" with respect to a functional conformational state of a GPCR (as defined herein), as used herein, refers to the retaining or holding of a GPCR in a subset of the possible conformations that it could otherwise assume, due to the effects of the interaction of the GPCR with the protein binding domain hereof. Accordingly, a protein that is "conformationally trapped" or "conformationally fixed" or "conformationally locked" or "conformationally frozen," as used herein, is one that is held in a subset of the possible conformations that it could otherwise assume, due to the effects of the interaction of the GPCR with the protein binding domain hereof. Within this context, a protein binding domain that specifically or selectively binds to a specific conformation or conformational state of a protein refers to a protein binding domain that binds with a higher affinity to a protein in a subset of conformations or conformational states than to other conformations or conformational states that the protein may assume. One of skill in the art will recognize that protein binding domains that specifically or selectively bind to a specific conformation or conformational state of a protein will stabilize this specific conformation or conformational state.

The term "a functional conformational state," as used herein, refers to the fact that proteins, in particular, membrane proteins such as GPCRs, possess many different conformational states having a dynamic range of activity, in particular, ranging from no activity to maximal activity (reviewed in Kobilka and Deupi, 2007). It should be clear that "a functional conformational state" is not meant to cover the denatured states of proteins. The functional versatility of GPCRs is inherently coupled to the flexibility of these proteins resulting in such a spectrum of conformations. The conformational energy landscape is intrinsically coupled to such factors as the presence of bound ligands (effector molecules, agonists, antagonists, inverse agonists, etc.), the lipid environment or the binding of interacting proteins. For example, a "basal conformational state" can be defined as a low energy state of the receptor in the absence of a ligand (as defined hereinbefore, e.g., effector molecules, agonists, antagonists, inverse agonists).

The probability that a protein will undergo a transition to another conformational state is a function of the energy difference between the two states and the height of the energy barrier between the two states. In the case of a receptor protein, such as a GPCR, the energy of ligand binding can be used either to alter the energy barrier between the two states, or to change the relative energy levels between the two states, or both. Changing of the energy barrier would have an effect on the rate of transition between the two states, whereas changing the energy levels would have an effect on the equilibrium distribution of receptors in two states. Binding of an agonist or partial agonist would lower the energy barrier and/or reduce the energy of the more active conformational state relative to the inactive conformational state. An inverse agonist would increase the energy barrier and/or reduce the energy of the "inactive state conformation" relative to the "active conformation." Coupling of the receptor to its G protein could further alter the energy landscape. The activities of integral membrane proteins, including GPCRs, are also affected by the structures of the lipid molecules that surround them in the membrane. Membrane proteins are not rigid entities, and deform to ensure good hydrophobic matching to the surrounding lipid bilayer. One important parameter is the hydrophobic thickness of the lipid bilayer, defined by the lengths of the lipid fatty acyl chains. Also, the structure of the lipid headgroup region is likely to be important in defining the structures of those parts of a membrane protein that are located in the lipid headgroup region. Among other lipids, palmitoylation and binding of cholesterol to GPCRs may also play a structural role inside monomeric receptors and contribute to the formation/stabilization of receptor oligomers (Lee 2004; Chini and Parenti 2009).

"Receptor ligands," or simply "ligands," as defined hereinbefore, may be "orthosteric" ligands (both natural and synthetic), meaning that they bind to the receptor's active site and are further classified according to their efficacy or, in other words, to the effect they have on receptor signaling through a specific pathway. As used herein, an "agonist" refers to a ligand that, by binding a receptor, increases the receptor's signaling activity. Full agonists are capable of maximal receptor stimulation; partial agonists are unable to elicit full activity even at saturating concentrations. Partial agonists can also function as "blockers" by preventing the binding of more robust agonists. An "antagonist" refers to a ligand that binds a receptor without stimulating any activity. An "antagonist" is also known as a "blocker" because of its ability to prevent binding of other ligands and, therefore, block agonist-induced activity. Further, an "inverse agonist" refers to an antagonist that, in addition to blocking agonist effects, reduces receptors' basal or constitutive activity below that of the unliganded receptor.

The canonical view of how GPCRs regulate cellular physiology is that the binding of ligands (such as hormones, neurotransmitters or sensory stimuli) stabilizes an active conformational state of the receptor, thereby allowing interactions with heterotrimeric G proteins. In addition to interacting with G proteins, agonist-bound GPCRs associate with GPCR kinases (GRKs), leading to receptor phosphorylation. A common outcome of GPCR phosphorylation by GRKs is a decrease in GPCR interactions with G proteins and an increase in GPCR interactions with arrestins, which sterically interdict further G-protein signaling, resulting in receptor desensitization. As β-arrestins turn off G-protein signals, they can simultaneously initiate a second, parallel set of signal cascades, such as the MAPK pathway. GPCRs also associate with various proteins outside the families of general GPCR-interacting proteins (G proteins, GRKs, arrestins and other receptors). These GPCR-selective partners can mediate GPCR signaling, organize GPCR signaling through G proteins, direct GPCR trafficking, anchor GPCRs, in particular, subcellular areas and/or influence GPCR pharmacology (Ritter and Hall 2009). In this regard, "ligands," as used herein, may also be "biased ligands" with the ability to selectively stimulate a subset of a receptor's signaling activities, for example, the selective activation of G-protein or β-arrestin function. Such ligands are known as "biased ligands," "biased agonists" or "functionally selective agonists." More particularly, ligand bias can be an imperfect bias characterized by a ligand stimulation of multiple receptor activities with different relative efficacies for different signals (non-absolute selectivity) or can be a perfect bias characterized by a ligand stimulation of one receptor activity without any stimulation of another known receptor activity.

The signaling activities of GPCRs (and thus their conformational behavior) may also be affected by the binding of another kind of ligands known as allosteric regulators. "Allosteric regulators" or otherwise "allosteric modulators," "allosteric ligands" or "effector molecules" bind at an allosteric site of a GPCR (that is, a regulatory site physically distinct from the protein's active site). In contrast to orthosteric ligands, allosteric modulators are non-competitive because they bind receptors at a different site and modify receptor function even if the endogenous ligand also is binding. Because of this, allosteric modulators are not limited to simply turning a receptor on or off, the way most drugs are. Instead, they act more like a dimmer switch, offering control over the intensity of activation or deactivation, while allowing the body to retain its natural control over initiating receptor activation. Allosteric regulators that enhance the protein's activity are referred to herein as "allosteric activators" or "positive allosteric modulators," whereas, those that decrease the protein's activity are referred to herein as "allosteric inhibitors" or otherwise "negative allosteric modulators."

Preferably, the protein binding domain hereof is capable of specifically binding to an agonist-bound GPCR and/or enhances the affinity of a GPCR for an agonist. It is preferred that the protein binding domain is capable of increasing the affinity for the agonist at least two-fold, at least five-fold and, more preferably, at least ten-fold upon binding to the receptor as measured by a decrease in $EC_{50}$, $IC_{50}$, $K_d$, or any other measure of affinity or potency known to one of skill in the art.

It will be appreciated that having increased stability with respect to structure and/or a particular biological activity of a GPCR may also be a guide to the stability of other denaturants or denaturing conditions including heat, a detergent, a chaotropic agent and an extreme pH. Accordingly, in a further embodiment, the protein binding domain hereof is capable of increasing the stability of a functional conformational state of a GPCR under non-physiological conditions induced by dilution, concentration, buffer composition, heating, cooling, freezing, detergent, chaotropic agent, or pH. In contrast to water-soluble proteins, thermodynamic studies of membrane protein folding and stability have proven to be extremely challenging, and complicated by the difficulty of finding conditions for reversible folding. Unfolding of helical membrane proteins induced by most methods, such as thermal and chemical approaches, is irreversible as reviewed by Stanley and Fleming (2008). The term "thermostabilize," "thermostabilizing," "increasing the thermostability of," as used herein, therefore, refers to the functional rather than to the thermodynamic properties of a GPCR and to the protein's resistance to irreversible denaturation induced by thermal and/or chemical approaches including, but not limited to, heating, cooling, freezing, chemical denaturants, pH, detergents, salts, additives, proteases or temperature. Irreversible denaturation leads to the irreversible unfolding of the functional conformations of the protein, loss of biological activity and aggregation of the denaturated protein. The terms "(thermo)stabilize," "(thermo)stabilizing," "increasing the (thermo)stability of," as used herein, apply to GPCRs embedded in lipid particles or lipid layers (for example, lipid monolayers, lipid bilayers, and the like) and to GPCRs that have been solubilized in detergent.

Preferably, the protein binding domain hereof is capable of increasing the thermostability of a functional conformational state of a GPCR, preferably, an active conformational state of a GPCR. In relation to an increased stability to heat, this can be readily determined by measuring ligand binding or by using spectroscopic methods such as fluorescence, CD or light scattering that are sensitive to unfolding at increasing temperatures (see also Example section). It is preferred that the protein binding domain is capable of increasing the stability as measured by an increase in the thermal stability of a GPCR in a functional conformational state with at least 2° C., at least 5° C., at least 8° C., and more preferably at least 10° C. or 15° C. or 20° C. According to another preferred embodiment, the protein binding domain is capable of increasing the thermal stability of a functional conformation of a GPCR in complex with a ligand such as, but not restricted to, an agonist, an inverse agonist, an antagonist and/or a modulator or an inhibitor of the GPCR or the GPCR-dependent signaling pathway. According to another preferred embodiment, the protein binding domain hereof is capable of increasing the stability in the presence of a detergent or a chaotrope of a functional conformational state of a GPCR. Preferably, the protein binding domain is capable of increasing the stability to denaturation induced by thermal or chemical approaches of the active conformational state of a GPCR. In relation to an increased stability to heat a detergent or to a chaotrope, the GPCR is typically incubated for a defined time in the presence of a test detergent or a test chaotropic agent and the stability is determined using, for example, ligand binding or a spectroscoptic method, optionally at increasing temperatures as discussed above. According to still another preferred embodiment, the protein binding domain hereof is capable of increasing the stability to extreme pH of a functional conformational state of a GPCR. Preferably, the protein binding domain is capable of increasing the stability to extreme pH of the active conformational state of a GPCR. In relation to an extreme of pH, a typical test pH would be chosen, for example, in the range 6 to 8, the range 5.5 to 8.5, the range 5 to 9, the range 4.5 to 9.5, more specifically in the range 4.5 to 5.5 (low pH) or in the range 8.5 to 9.5 (high pH).

The protein binding domains hereof may generally be directed against any desired GPCR and may, in particular, be directed against any conformational epitope of any GPCR, preferably a functional conformational state of any GPCR, more preferably an active conformational state of a GPCR (all as defined hereinbefore). More particularly, the conformational epitope can be part of an intracellular or extracellular region, or an intramembranous region, or a domain or loop structure of any desired GPCR. According to particular embodiments, the protein binding domains may be directed against any suitable extracellular region, domain, loop or other extracellular conformational epitope of a GPCR, but is preferably directed against one of the extracellular parts of the transmembrane domains or more preferably against one of the extracellular loops that link the transmembrane domains. Alternatively, the protein binding domains may be directed against any suitable intracellular region, domain, loop or other intracellular conformational epitope of a GPCR, but is preferably directed against one of the intracellular parts of the transmembrane domains or, more preferably, against one of the intracellular loops that link the transmembrane domains. A protein binding domain that specifically binds to a "three-dimensional" epitope or "conformational" epitope specifically binds to a tertiary (i.e., three-dimensional) structure of a folded protein, and binds at much reduced (i.e., by a factor of at least 2, 5, 10, 50 or 100) affinity to the linear (i.e., unfolded, denatured) form of the protein. It is further expected that the protein binding domains hereof will generally bind to all naturally occurring or synthetic analogs, variants, mutants, or alleles of the GPCR.

In a specific embodiment, the protein binding domain hereof is capable of specifically binding to an intracellular conformational epitope of a GPCR. Preferably, the protein binding domain is capable of specifically binding a conformational epitope that is comprised in, located at, or overlaps with, the G protein binding site of a GPCR. More preferably, the protein binding domains may occupy the G protein binding site of a functional conformational state of a GPCR, more preferably, of an active conformational state of a GPCR. Most preferably, the protein binding domains show G protein-like behavior. The term "G protein-like behavior" as used herein refers to the property of protein binding domains to preferentially bind agonist-bound receptor versus, for example, inverse agonist-bound receptor. Protein binding domains showing G protein-like behavior also enhance the affinity of the receptor for agonists, which is attributed to the cooperative interaction between agonist-occupied receptor and G protein (see also Example section).

In a preferred embodiment, the protein binding domain is derived from an innate or adaptive immune system. Preferably, the protein binding domain is derived from an immunoglobulin. Preferably, the protein binding domain hereof is an antibody or a derivative thereof. The term "antibody" (Ab) refers generally to a polypeptide encoded by an immunoglobulin gene, or functional fragments thereof, that specifically binds and recognizes an antigen, and is known to the person skilled in the art. A conventional immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains, respectively. The term "antibody" is meant to include whole antibodies, including single-chain whole antibodies, and antigen-binding fragments. In some embodiments, antigen-binding fragments may be antigen-binding antibody fragments that include, but are not limited to, Fab, Fab' and F(ab')2, Fd, single-chain Fvs (scFv), single-chain antibodies, disulfide-linked Fvs (dsFv) and fragments comprising or consisting of either a VL or VH domain, and any combination of those or any other functional portion of an immunoglobulin peptide capable of binding to the target antigen. The term "antibodies" is also meant to include heavy chain antibodies, or functional fragments thereof, such as single domain antibodies, more specifically, nanobodies, as defined further herein.

Preferably, the protein binding domain comprises an amino acid sequence comprising four framework regions and three complementarity-determining regions, preferably in a sequence FR1-CDR1-FR2-CDR2-FR3-CDR3-FR4, or any suitable fragment thereof (which will then usually contain at least some of the amino acid residues that form at least one of the complementarity-determining regions). Protein binding domains comprising four FRs and three CDRs are known to the person skilled in the art and have been described, as a non-limiting example, in Wesolowski et al. (2009).

Preferably, the protein binding domain hereof is derived from a camelid antibody. More preferably, the protein binding domain hereof comprises an amino acid sequence of a nanobody, or any suitable fragment thereof. More specifically, the protein binding domain is a nanobody or any suitable fragment thereof. A "nanobody" (Nb), as used herein, refers to the smallest antigen binding fragment or single variable domain ("VHH") derived from naturally occurring heavy chain antibody and is known to the person skilled in the art. They are derived from heavy chain only antibodies, seen in camelids (Hamers-Casterman et al. 1993; Desmyter et al. 1996). In the family of "camelids," immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a nanobody or a VHH antibody. Nanobody™, Nanobodies™ and Nanoclone™ are trademarks of Ablynx NV (Belgium). The small size and unique biophysical properties of Nbs excel conventional antibody fragments for the recognition of uncommon or hidden epitopes and for binding into cavities or active sites of protein targets. Further, Nbs can be designed as bispecific and bivalent antibodies or attached to reporter molecules (Conrath et al. 2001). Nbs are stable and rigid single domain proteins that can easily be manufactured and survive the gastro-intestinal system. Therefore, Nbs can be used in many applications including drug discovery and therapy (Saerens et al. 2008), but also as a versatile and valuable tool for purification, functional study and crystallization of proteins (Conrath et al. 2009).

The nanobodies hereof generally comprise a single amino acid chain that can be considered to comprise four "framework sequences" or FRs and three "complementarity-determining regions" or CDRs (as defined hereinbefore). Non-limiting examples of nanobodies hereof are described in more detail further herein. It should be clear that framework regions of nanobodies may also contribute to the binding of their antigens (Desmyter et al. 2002; Korotkov et al. 2009).

Non-limiting examples of the nanobodies hereof include, but are not limited to, nanobodies as defined by SEQ ID NOS:1-29 (see FIG. 12, Table 1). The delineation of the CDR sequences is based on the IMGT unique numbering system for V-domains and V-like domains (Lefranc et al. 2003). In a specific embodiment, the above nanobodies can comprise at least one of the complementarity-determining regions (CDRs) with an amino acid sequence selected from SEQ ID NOS:30-70 (see FIG. 12; Table 2). More specifically, the above nanobodies can be selected from the group comprising SEQ ID NOS:1-29, or a functional fragment thereof. A "functional fragment" or a "suitable fragment," as used herein, may, for example, comprise one of the CDR loops. Preferably, the functional fragment comprises CDR3. More specifically, the nanobodies consist of any of SEQ ID NOS:1-29 and the functional fragment of the nanobodies consist of any of SEQ ID NOS:30-70. In still another embodiment, a nucleic acid sequence encoding any of the above nanobodies or functional fragments is also part hereof. Further, also envisaged are expression vectors comprising nucleic acid sequences encoding any of the above nanobodies or functional fragments thereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the nanobodies can be done according to techniques known by the skilled person in the art.

It should be noted that the term "nanobody," as used herein in its broadest sense, is not limited to a specific biological source or to a specific method of preparation. For example, the nanobodies hereof can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding such a humanized VHH domain; (4) by "camelization" of a naturally occurring VH domain from any animal species, and, in particular, from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing.

One preferred class of nanobodies corresponds to the VHH domains of naturally occurring heavy chain antibodies directed against a functional conformational state of a GPCR. Although naive or synthetic libraries of nanobodies (for examples of such libraries, see WO9937681, WO0043507, WO0190190, WO03025020 and WO03035694) may contain conformational binders against a GPCR in a functional conformational state, a preferred embodiment of this invention includes the immunization of a Camelidae with a GPCR in a functional conformational state, optionally bound to a receptor ligand, to expose the immune system of the animal with the conformational epitopes that are unique to the GPCR (for example, agonist-bound GPCR so as to raise antibodies directed against a GPCR in its active conformational state). Thus, as further described herein, such VHH sequences can preferably be generated or obtained by suitably immunizing a species of Camelid with a GPCR, preferably a GPCR in a functional conformational state, more preferably an active conformational state (i.e., so as to raise an immune response and/or heavy chain antibodies directed against the GPCR), by obtaining a suitable biological sample from the Camelid (such as a blood sample, or any sample of B-cells), and by generating $V_HH$ sequences directed against the GPCR, starting from the sample. Such techniques will be clear to the skilled person. Yet another technique for obtaining the desired VHH sequences involves suitably immunizing a transgenic mammal that is capable of expressing heavy chain antibodies (i.e., so as to raise an immune response and/or heavy chain antibodies directed against a GPCR in a functional conformational state), obtaining a suitable biological sample from the transgenic mammal (such as a blood sample, or any sample of B-cells), and then generating VHH sequences directed against the GPCR starting from the sample, using any suitable technique known per se. For example, for this purpose, the heavy chain antibody-expressing mice and the further methods and techniques described in WO02085945 and in WO04049794 can be used.

Accordingly, the invention encompasses methods of generating protein binding domains hereof. As a non-limiting example, a method is provided of generating nanobodies specifically binding to a conformational epitope of a functional conformational state of a GPCR, comprising:
(i) immunizing an animal with a GPCR, and
(ii) screening for nanobodies specifically binding to a conformational epitope of a functional conformational state of the GPCR.

Preferably, immunization of an animal will be done with a GPCR in the presence of a receptor ligand, wherein the ligand induces a particular functional conformational state of the GPCR. For example, nanobodies may be generated that are specifically binding to a conformational epitope of an active conformational state of a GPCR by immunizing an animal with a GPCR in the presence of an agonist that induces the formation of an active conformational state of the GPCR (see also Example section).

For the immunization of an animal with a GPCR, the GPCR may be produced and purified using conventional methods that may employ expressing a recombinant form of the GPCR in a host cell, and purifying the GPCR using affinity chromatography and/or antibody-based methods. In particular embodiments, the baculovirus/Sf-9 system may be employed for expression, although other expression systems (e.g., bacterial, yeast or mammalian cell systems) may also be used. Exemplary methods for expressing and purifying GCPRs are described in, for example, Kobilka (1995), Eroglu et al. (2002), Chelikani et al. (2006) and the book *Identification and Expression of G Protein-Coupled Receptors* (Kevin R. Lynch (Ed.), 1998), among many others. A GPCR may also be reconstituted in phospholipid vesicles. Likewise, methods for reconstituting an active GPCR in phospholipid vesicles are known, and are described in: Luca et al. (2003), Mansoor et al. (2006), Niu et al. (2005), Shimada et al. (2002), and Eroglu et al. (2003), among others. In certain cases, the GPCR and phospholipids may be reconstituted at high density (e.g., 1 mg receptor per mg of phospholipid). In particular embodiments, the phospholipids vesicles may be tested to confirm that the GPCR is active. In many cases, a GPCR may be present in the phospholipid vesicle in both orientations (in the normal orientation, and in the "upside down" orientation in which the intracellular loops are on the outside of the vesicle). Other immunization methods with a GPCR include, without limitation, the use of complete cells expressing a GPCR, vaccination with a nucleic acid sequence encoding a GPCR (e.g., DNA vaccination), immunization with viruses or virus-like particles expressing a GPCR, amongst others.

Any suitable animal, e.g., a warm-blooded animal, in particular, a mammal such as a rabbit, mouse, rat, camel, sheep, cow, shark, or pig or a bird such as a chicken or turkey, may be immunized using any of the techniques well known in the art suitable for generating an immune response.

The screening for nanobodies, as a non-limiting example, specifically binding to a conformational epitope of a functional conformational state of the GPCR may, for example, be performed by screening a set, collection or library of cells that express heavy chain antibodies on their surface (e.g., B-cells obtained from a suitably immunized Camelid), or bacteriophages that display a fusion of genIII and nanobody at their surface, by screening of a (naïve or immune) library of VHH sequences or nanobody sequences, or by screening of a (naïve or immune) library of nucleic acid sequences that encode VHH sequences or nanobody sequences, which may all be performed in a manner known per se, and which method may optionally further comprise one or more other suitable steps, such as, for example and without limitation, a step of affinity maturation, a step of expressing the desired amino acid sequence, a step of screening for binding and/or for activity against the desired antigen (in this case, the GPCR), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

A particularly preferred class of protein binding domains hereof comprises nanobodies with an amino acid sequence that corresponds to the amino acid sequence of a naturally occurring VHH domain, but that has been "humanized," i.e., by replacing one or more amino acid residues in the amino acid sequence of the naturally occurring VHH sequence (and, in particular, in the framework sequences) by one or more of the amino acid residues that occur at the corresponding position(s) in a VH domain from a conventional four-chain antibody from a human being. This can be performed in a manner known per se, which will be clear to the skilled person, on the basis of the further description herein and the prior art on humanization. Again, it should be noted that such humanized Nanobodies hereof can be obtained in any suitable manner known per se (i.e., as indicated under points (1)-(8) above) and, thus, are not strictly limited to polypeptides that have been obtained using a polypeptide that comprises a naturally occurring VHH domain as a starting material. Humanized nanobodies may have several advantages, such as a reduced immunogenicity, compared to the corresponding naturally occurring VHH domains. Such humanization generally involves replacing one or more amino acid residues in the sequence of a naturally occurring VHH with the amino acid residues that occur at the same position in a human VH domain, such as a human VH3 domain. The humanizing substitutions should be chosen such that the resulting humanized nanobodies still retain the favorable properties of nanobodies as defined herein. The skilled person will be able to select humanizing substitutions or suitable combinations of humanizing substitutions that optimize or achieve a desired or suitable balance between the favorable properties provided by the humanizing substitutions on the one hand and the favorable properties of naturally occurring VHH domains on the other hand.

Another particularly preferred class of protein binding domains hereof comprises nanobodies with an amino acid sequence that corresponds to the amino acid sequence of a naturally occurring VH domain, but that has been "camelized," i.e., by replacing one or more amino acid residues in the amino acid sequence of a naturally occurring VH domain from a conventional four-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues, as defined herein (see, for example, WO9404678). Preferably, the VH sequence that is used as a starting material or starting point for generating or designing the camelized nanobody is preferably a VH sequence from a mammal, more preferably the VH sequence of a human being, such as a VH3 sequence. However, it should be noted that such camelized nanobodies hereof can be obtained in any suitable manner known per se (i.e., as indicated under points (1)-(8) above) and thus are not strictly limited to polypeptides that have been obtained using a polypeptide that comprises a naturally occurring VH domain as a starting material.

For example, both "humanization" and "camelization" can be performed by providing a nucleotide sequence that encodes a naturally occurring VHH domain or VH domain, respectively, and then changing, in a manner known per se, one or more codons in the nucleotide sequence in such a way that the new nucleotide sequence encodes a "humanized" or "camelized" nanobody hereof, respectively. This nucleic acid can then be expressed in a manner known per se, so as to provide the desired nanobody hereof. Alternatively, based on the amino acid sequence of a naturally occurring VHH domain or VH domain, respectively, the amino acid sequence of the desired humanized or camelized nanobody hereof, respectively, can be designed and then synthesized de novo using techniques for peptide synthesis known per se. Also, based on the amino acid sequence or nucleotide sequence of a naturally occurring VHH domain or VH domain, respectively, a nucleotide sequence encoding the desired humanized or camelized nanobody hereof, respectively, can be designed and then synthesized de novo using techniques for nucleic acid synthesis known per se, after which the nucleic acid thus obtained can be expressed in a manner known per se, so as to provide the desired nanobody hereof.

Other suitable methods and techniques for obtaining the nanobodies hereof and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a nanobody hereof or a nucleotide sequence or nucleic acid encoding the same.

It is also within the scope hereof to use natural or synthetic analogs, mutants, variants, alleles, homologs and orthologs (herein collectively referred to as "analogs") of the protein binding domains hereof, preferably to the nanobodies, and in particular analogs of the nanobodies of SEQ ID NOS:1-29 (see Table 1, FIG. 12). Thus, according to one embodiment hereof, the term "nanobody hereof" in its broadest sense also covers such analogs. Generally, in such analogs, one or more amino acid residues may have been replaced, deleted and/or added, compared to the nanobodies hereof as defined herein. Such substitutions, insertions, deletions or additions may be made in one or more of the framework regions and/or in one or more of the CDRs and, in particular, analogs of the CDRs of the nanobodies of SEQ ID NOS:1-29, the CDRs corresponding with SEQ ID NOS: 30-70 (see Table 2, FIG. 12). "Analogs," as used herein, are sequences wherein each or any framework region and each or any complementarity-determining region shows at least 80% identity, preferably at least 85% identity, more preferably 90% identity, even more preferably, 95% identity with the corresponding region in the reference sequence (i.e., FR1_analog versus FR1_reference, CDR1_analog versus CDR1_reference, FR2_analog versus FR2_reference, CDR2_analog versus CDR2_reference, FR3_analog versus FR3_reference, CDR3_analog versus CDR3_reference, FR4_analog versus FR4_reference), as measured in a BLASTp alignment (Altschul et al. 1987; FR and CDR definitions according to IMGT unique numbering system for V-domains and V-like domains (Lefranc et al. 2003)).

By means of non-limiting examples, a substitution may, for example, be a conservative substitution (as described herein) and/or an amino acid residue may be replaced by another amino acid residue that naturally occurs at the same position in another VHH domain. Thus, any one or more substitutions, deletions or insertions, or any combination thereof, that either improve the properties of the nanobody hereof or that at least do not detract too much from the desired properties or from the balance or combination of desired properties of the nanobody hereof (i.e., to the extent that the nanobody is no longer suited for its intended use), are included within the scope hereof. A skilled person will generally be able to determine and select suitable substitutions, deletions, insertions, additions, or suitable combinations thereof, based on the disclosure herein and optionally after a limited degree of routine experimentation, which may, for example, involve introducing a limited number of possible substitutions and determining their influence on the properties of the nanobodies thus obtained.

For example, and depending on the host organism used to express the protein binding domain hereof, preferably the nanobody, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example, to allow site-specific pegylation.

Examples of modifications, as well as examples of amino acid residues within the protein binding domain sequence, preferably the nanobody sequence, that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the nanobody hereof invention and, in particular, of one or more functional groups, residues or moieties that confer one or more desired properties or functionalities to the nanobody hereof. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins and, in particular, for the modification of antibodies or antibody fragments (including ScFvs and single domain antibodies), for which reference is, for example, made to *Remington's Pharmaceutical Sciences*, 16th ed., Mack Publishing Co., Easton, Pa. (1980). Such functional groups may, for example, be linked directly (for example, covalently) to a nanobody hereof, or optionally via a suitable linker or spacer, as will again be clear to the skilled person. One of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including, but not limited to, single domain antibodies and ScFvs); reference is made to, for example, Chapman, *Nat. Biotechnol.* 54, 531-545 (2002); by Veronese and Harris, *Adv. Drug Deliv. Rev.* 54, 453-456 (2003); by Harris and Chess, *Nat. Rev. Drug Discov.* 2 (2003); and in WO04060965. Various reagents for pegylation of proteins are also commercially available, for example, from Nektar Therapeutics, USA. Preferably, site-directed pegylation is used, in particular, via a cysteine-residue (see, for example, Yang et al., *Protein Engineering* 16 (10):761-770 (2003). For example, for this purpose, PEG may be attached to a cysteine residue that naturally occurs in a nanobody hereof. A nanobody hereof may be modified so as to suitably introduce one or more cysteine residues for attachment of PEG, or an amino acid sequence comprising one or more cysteine residues for attachment of PEG may be fused to the N- and/or C-terminus of a nanobody hereof, all using techniques of protein engineering known per se to the skilled person. Preferably, for the nanobodies and proteins hereof, a PEG is used with a molecular weight of more than 5000, such as more than 10,000 and less than 200,000, such as less than 100,000; for example, in the range of 20,000-80,000. Another, usually less preferred modification comprises N-linked or O-linked glycosylation, usually as part of co-translational and/or post-translational modification, depending on the host cell used for expressing the nanobody or polypeptide hereof. Another technique for increasing the half-life of a nanobody may comprise the engineering into bifunctional nanobodies (for example, one nanobody against the target GPCR and one against a serum protein such as albumin) or into fusions of nanobodies with peptides (for example, a peptide against a serum protein such as albumin).

Yet another modification may comprise the introduction of one or more detectable labels or other signal-generating groups or moieties, depending on the intended use of the labeled protein binding domain, in particular, the nanobody. Suitable labels and techniques for attaching, using and detecting them will be clear to the skilled person, and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled nanobodies and polypeptides hereof may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example to chelate one of the metals or metallic cations referred to above. Suitable chelating groups, for example, include, without limitation, diethylenetriaminepentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the nanobody hereof to another protein, polypeptide or chemical compound that is bound to the other half of the binding pair, i.e., through formation of the binding pair. For example, a nanobody hereof may be conjugated to biotin, and linked to another protein, polypeptide, compound or carrier conjugated to avidin or streptavidin. For example, such a conjugated nanobody may be used as a reporter, for example, in a diagnostic system where a detectable signal-producing agent is conjugated to avidin or streptavidin. Such binding pairs may, for example, also be used to bind the nanobody hereof to a carrier, including carriers suitable for pharmaceutical purposes. One non-limiting example is the liposomal formulations described by Cao and Suresh, *Journal of Drug Targeting* 8 (4):257 (2000). Such binding pairs may also be used to link a therapeutically active agent to the nanobody hereof.

In a particular embodiment, the nanobody hereof is bivalent and formed by bonding together, either chemically or by recombinant DNA techniques, two monovalent single domains of heavy chains. In another particular embodiment, the nanobody hereof is bi-specific and formed by bonding together two variable domains of heavy chains, each with a different specificity. Similarly, polypeptides comprising multivalent or multi-specific nanobodies are included here as non-limiting examples. Preferably, a monovalent nanobody hereof is such that it will bind to an extracellular part, region, domain, loop or other extracellular epitope of a functional conformational state of a GPCR, more preferably, an active conformational state of a GPCR, with an affinity less than 500 nM, preferably less than 200 nM, more preferably less than 10 nM, such as less than 500 pM. Alternatively, a monovalent nanobody hereof is such that it will bind to an intracellular part, region, domain, loop or other intracellular epitope of a functional conformational state of a GPCR, more preferably, an active conformational state of a GPCR with an affinity less than 500 nM, preferably less than 200 nM, more preferably less than 10 nM, such as less than 500 pM. Also, according to this aspect, any multivalent or multispecific (as defined herein) nanobody hereof may also be suitably directed against two or more different extracellular or intracellular parts, regions, domains, loops or other extracellular or intracellular epitopes on the same antigen, for example, against two different extracellular or intracellular loops or against two different extracellular or intracellular parts of the transmembrane domains. Such multivalent or multispecific nanobodies hereof may also have (or be engineered and/or selected for) increased avidity and/or improved selectivity for the desired GPCR, and/or for any other desired property or combination of desired properties that may be obtained by the use of such multivalent or multispecific nanobodies. In a particular embodiment, such multivalent or multispecific nanobodies hereof may also have (or be engineered and/or selected for) improved efficacy in modulating signaling activity of a GPCR (see also further herein). It will be appreciated that the multivalent or multispecific nanobodies hereof may additionally be suitably directed to a different antigen, such as, but not limiting to, a ligand interacting with a GPCR or one or more downstream signaling proteins.

A second aspect hereof relates to a complex comprising (i) a protein binding domain hereof, (ii) a GPCR in a functional conformational state, and optionally, (iii) a receptor ligand. A "receptor ligand" or a "ligand," as defined herein, may be a small compound, a protein, a peptide, a protein scaffold, a nucleic acid, an ion, a carbohydrate or an antibody, or any suitable fragment derived thereof, and the like. Preferentially, the ligand is from the agonist class and the receptor is in an active conformational state. The ligand may also be an inverse agonist, an antagonist, or a biased ligand. The ligands may be orthosteric or allosteric. Ligands also include allosteric modulators, potentiators, enhancers, negative allosteric modulators and inhibitors. They may have biological activity by themselves or they may modulate activity only in the presence of another ligand. Neubig et al. (2003) describe many of the classes of ligands.

Provided for is a complex wherein the protein binding domain is bound to the GPCR; preferably, the protein binding domain is bound to the GPCR, wherein the GPCR is bound to a receptor ligand. To illustrate this further, and without the purpose of being limitative, a stable ternary complex containing a nanobody, a GPCR and an agonist can be purified by affinity chromatography or gel filtration from a mixture, containing (1) a nanobody that is specific for the active conformation of that GPCR, (2) the detergent-solubilized receptor and (3) an agonist.

In another embodiment, the complex is crystalline. So, a crystal of the complex is also provided, as well as methods of making the crystal, which are described in greater detail below. A crystalline form of a complex may comprise (i) a protein binding domain hereof, (ii) a GPCR in a functional conformational state, preferably an active conformational state, and optionally, (iii) a receptor ligand, is envisaged, wherein the crystalline form is obtained by the use of a protein binding domain hereof.

In yet another embodiment, the complex hereof is in a solubilized form, for example, after aqueous solubilization with a detergent. In an alternative preferred embodiment, the complex hereof is immobilized to a solid support. Non-limiting examples of solid supports, as well as methods and techniques for immobilization, are described further in the detailed description. In still another embodiment, the complex hereof is in a "cellular composition," including an organism, a tissue, a cell, a cell line, and a membrane composition derived from the organism, tissue, cell or cell line. The membrane composition is also meant to include any liposomal composition that may comprise natural or synthetic lipids or a combination thereof. Examples of membrane or liposomal compositions include, but are not limited to, organelles, membrane preparations, virus-like lipoparticles, lipid layers (bilayers and monolayers), lipid vesicles, high-density lipoparticles (e.g., nanodisks), and the like. It will be appreciated that a cellular composition, or a membrane-like or liposomal composition, may comprise natural or synthetic lipids.

Accordingly, a third aspect relates to a cellular composition, including a membrane or liposomal composition derived thereof (all as defined hereinabove), comprising a protein binding domain and/or a complex hereof. Preferably, the cellular composition providing and/or expressing the protein binding domain is capable of stabilizing and/or inducing a functional conformational state of a GPCR upon binding of the protein binding domain. It will be understood that it is essential to retain sufficient functionality of the respective proteins, for which methods and techniques are available and known to the person skilled in the art. It will also be appreciated that the cellular composition may provide and/or express a target GPCR endogenously or exogenously.

Preparations of GPCRs formed from membrane fragments or membrane-detergent extracts are reviewed in detail in Cooper (2004), incorporated herein by reference. Non-limiting examples of solubilized receptor preparations are further provided in the Example section.

Transfection of target cells (e.g., mammalian cells) can be carried out following principles outlined by Sambrook and Russel (*Molecular Cloning, A Laboratory Manual*, 3$^{rd}$ Edition, Volume 3, Chapter 16, Sections 16.1-16.54). In addition, viral transduction can also be performed using reagents such as adenoviral vectors. Selection of the appropriate viral vector system, regulatory regions and host cell is common knowledge within the level of ordinary skill in the art. The resulting transfected cells are maintained in culture or frozen for later use according to standard practices. Preferably, cells are eukaryotic cells, for example, yeast cells, or cultured cell lines, for example, mammalian cell lines, preferably human cell lines, that express a GPCR of interest. Preferred cell lines functionally expressing the protein binding domain and/or the GPCR include insect cells (e.g., SF-9), human cell lines (e.g., HEK293), rodent cell lines (e.g., CHO-K1), and camelid cell lines (Dubca).

The protein binding domains or the complexes or the cellular composition as described hereinbefore can be used in a variety of context and applications, which will be described in further detail below.

Crystallization and Resolving the Structure of a GPCR

Crystallization of membrane proteins including GPCRs remains a formidable challenge. Although expression and purification methods are appearing that allow for the generation of milligram quantities, achieving stability with these molecules is perhaps the most difficult hurdle to overcome. Purification necessitates a release of the GPCR from the lipid bilayer by detergent solubilization, a process during which hydrophobic surfaces of the protein are coated with surfactant monomers to form a protein-detergent complex (PDC). However, the detergent belt formed around the protein is a poor replacement for the lipid bilayer, as much of the lateral pressure exerted on the protein by the surrounding lipids is lost. Thus, solubilization of membrane proteins often results in destabilization, unfolding and subsequent aggregation. GPCRs other than rhodopsin typically have poor stability in detergents and are prone to aggregation and proteolysis. Efforts to crystallize GPCRs have been frustrated by other intrinsic characteristics of integral membrane proteins. The seven hydrophobic transmembrane helices of GPCRs make poor surfaces for crystal contacts, and the extracellular and intracellular domains are often relatively short and/or poorly structured. Besides for rhodopsin (an atypical GPCR in terms of natural abundance and stability), the first crystals of GPCRs were obtained from $\beta_2AR$ bound to a Fab fragment that recognized an epitope composed of the amino and carboxyl terminal ends of the third intracellular loop connecting TMs 5 and 6 (Rasmussen, 2007). In the second approach, the third intracellular loop was replaced by T4 lysozyme ($\beta_2AR$-T4L; Rosenbaum, 2007). Finally, the remarkable versatility of GPCRs as signaling molecules can be attributed to its flexible and dynamic three-dimensional structure. Unfortunately, such dynamic behavior is particularly challenging for high-resolution structure analysis. Growing diffraction quality crystals requires stable, conformationally homogenous protein. As such, diffraction-quality crystals of a native, unbound GPCR are difficult to obtain and, even when this goal is achieved, the crystal structure will represent only one of the many native conformations. Many of these problems can be solved in the invention by the use of protein binding domains, in particular, nanobodies, as tools for stabilizing, purifying and crystallizing specific conformational states of GPCRs for high-resolution structure analysis.

It is thus one of the aims hereof to use protein binding domains as tools to stabilize GPCR proteins and further to use these protein binding domains as co-crystallization aids for GPCRs, or in other words, to facilitate crystallogenesis of GPCRs, preferably in a functional conformational state.

Accordingly, a fourth aspect relates to the use of a protein binding domain hereof, or in specific embodiments, a complex comprising the protein binding domain or a cellular composition providing the protein binding domain, to stabilize a GPCR in a functional conformational state, in particular, in an active conformational state; and/or to induce the formation of a particular functional (preferably, active) conformational state within a GPCR. It will be appreciated that such a protein binding domain is a very useful tool to purify, to crystallize and/or to solve the structure of a GPCR in a functional conformational state, in particular, in its active conformational state. As clearly outlined hereinbefore, it should be clear that the protein binding domains hereof invention, which are to be used for purifying, stabilizing, crystallizing and/or solving the structure of a GPCR, may be directed against any desired GPCR and may specifically bind to or recognize a conformational epitope of a functional conformational state, preferably an active conformational state, of any desired GPCR. In particular, the conformational epitope can be part of an intracellular or extracellular region, or an intramembranous region, or a domain or loop structure of any desired GPCR.

First, protein binding domains hereof may increase the thermostability of detergent-solubilized receptors, stabilized in a particular conformational state, protecting them from proteolytic degradation and/or aggregation and facilitating the purification and concentration of homogeneous samples of correctly folded receptor. Persons of ordinary skill in the art will recognize that such samples are the preferred starting point for the generation of diffracting crystals.

The crystallization of the purified receptor is another major bottleneck in the process of macromolecular structure determination by X-ray crystallography. Successful crystallization requires the formation of nuclei and their subsequent growth to crystals of suitable size. Crystal growth generally occurs spontaneously in a supersaturated solution as a result of homogenous nucleation. Proteins may be crystallized in a typical sparse matrix screening experiment, in which precipitants, additives and protein concentration are sampled extensively, and supersaturation conditions suitable for nucleation and crystal growth can be identified for a particular protein. Related to the sparse matrix screening approach is to generate structural variation in the protein itself, for example, by adding ligands that bind the protein, or by making different mutations, preferentially in surface residues of the target protein or by trying to crystallize different species orthologues of the target protein (Chang 1998). One unexpected finding is the usefulness of protein binding domains, such as nanobodies, that specifically bind to a GPCR to introduce a degree of structural variation upon binding while preserving the overall fold of the GPCR. Different nanobodies will generate different quaternary structures providing new distinct interfaces for crystal lattice formation resulting in multiple crystal forms while preserving the overall fold of the GPCR.

Because crystallization involves an unfavorable loss of conformational entropy in the molecule to be assembled in the crystal lattice, methods that reduce the conformational entropy of the target while still in solution should enhance the likelihood of crystallization by lowering the net entropic penalty of lattice formation. The "surface entropy reduction" approach has proved to be highly effective (Derewenda 2004). Likewise, binding partners such as ions, small molecule ligands, and peptides can reduce the conformational heterogeneity by binding to and stabilizing a subset of conformational states of a protein. Although such binding partners are effective, not all proteins have a known binding partner, and even when a binding partner is known, its affinity, solubility, and chemical stability may not be compatible with crystallization trials. Therefore, it was surprisingly found that the protein binding domains hereof, in particular, the nanobodies, can be used as tools to increase the probability of obtaining well-ordered crystals by minimizing the conformational heterogeneity in the target GPCR by binding to a particular conformation of the receptor.

Crystallization of GPCRs for high-resolution structural studies is particularly difficult because of the amphipathic surface of these membrane proteins. Embedded in the membrane bilayer, the contact sites of the protein with the acyl chains of the phospholipids are hydrophobic, whereas the polar surfaces are exposed to the polar head groups of the lipids and to the aqueous phases. To obtain well-ordered three-dimensional crystals—a prerequisite to X-ray structural analysis at high resolution—GPCRs are solubilized with the help of detergents and purified as protein-detergent complexes. The detergent micelle covers the hydrophobic surface of the membrane protein in a belt-like manner (Hunte and Michel 2002; Ostermeier et al. 1995). GPCR-detergent complexes form three-dimensional crystals in which contacts between adjacent protein molecules are made by the polar surfaces of the protein protruding from the detergent micelle (Day et al. 2007). Obviously, the detergent micelle requires space in the crystal lattice. Although attractive interactions between the micelles might stabilize the crystal packing (Rasmussen et al. 2007; Dunn et al. 1997), these interactions do not lead to rigid crystal contacts. Because many membrane proteins, including GPCRs, contain relatively small or highly flexible hydrophilic domains, a strategy to increase the probability of getting well-ordered crystals is to enlarge the polar surface of the protein and/or to reduce their flexibility. In order for the nanobodies hereof to be used to enlarge the polar surfaces of the protein, supplementing the amount of protein surface can facilitate primary contacts between molecules in the crystal lattice. Nanobodies hereof can also reduce the flexibility of its extracellular regions to grow well-ordered crystals. Nanobodies are especially suited for this purpose because they are composed of one single rigid globular domain and are devoid of flexible linker regions unlike conventional antibodies or fragments derived such as Fabs.

In a further embodiment, the complex comprising the protein binding domain hereof and the target GPCR in a functional conformational state, preferably an active conformational state, may be crystallized using any of a variety of specialized crystallization methods for membrane proteins, many of which are reviewed in Caffrey (2003). In general terms, the methods are lipid-based methods that include adding lipid to the GPCR-nanobody complex prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phase crystallization methods are described in, for example, Landau et al. 1996; Gouaux 1998; Rummel et al. 1998; Nollert et al. 2004, which publications are incorporated by reference for disclosure of those methods. Bicelle crystallization methods are described in, for example, Faham et al. 2005; Faham et al. 2002, which publications are incorporated by reference for disclosure of those methods.

Further encompassed is the use of a protein binding domain as described hereinbefore to solve a structure of a GPCR. The structure of a protein, in particular a GPCR, includes the primary, secondary, tertiary and, if applicable, quaternary structure of the protein. "Solving the structure" as used herein refers to determining the arrangement of atoms or the atomic coordinates of a protein, and is often done by a biophysical method, such as X-ray crystallography.

In x-ray crystallography, the diffraction data when properly assembled gives the amplitude of the 3D Fourier transform of the molecule's electron density in the unit cell. If the phases are known, the electron density can be simply obtained by Fourier synthesis. For a protein complex, the success to derive phase information from molecular replacement (MR) alone is questionable when the fraction of proteins with a known structure (the search models) is low (less than 50% of the amino acid content) and/or when the crystals exhibit limited diffraction quality. While the combination of multiple isomorphous replacement (MIR) and MR phasing has proven successful for protein complexes (e.g., Ostermeier et al. 1995; Li et al. 1997; Hunte et al. 2000), the requirement of producing a good heavy atom derivative is almost always problematic. Over the past decade, classical MIR approaches have generally been superseded by the use of anomalous dispersion data principally using selenomethionine (SeMet) incorporation (MAD or SAD) (Hendrickson 1991). In fact, the anomalous experimental data using Se-edge energies generally provide superior and less biased phase information compared with either MIR or model-based MR phasing data. One embodiment relates to the use of nanobodies for the phasing of GPCR-nanobody complexes by MR or MAD. Nanobodies generally express robustly and are suitable for SeMet incorporation. Phasing a GPCR-nanobody complex by introducing all the SeMet sites in the nanobody alone circumvents the need to incorporate SeMet sites in the GPCR.

In many cases, obtaining a diffraction-quality crystal is the chief barrier to solving its atomic-resolution structure. Thus, according to specific embodiments, the protein binding domains as described hereinbefore, in particular, the nanobodies, can be used to improve the diffraction quality of the crystals so that the GPCR protein crystal structure can be solved.

There is great interest in structural information to help guide GPCR drug discovery. For the GPCRs whose structures have now been solved, these modeling efforts have been shown to be imprecise at the level required by in silico drug designers. With the inactive-state structures of $\beta_2AR$, the $\beta_1AR$ and the A2A receptor, pharmaceutical chemists now have experimental data to guide the development of ligands for several active therapeutic targets. However, the value of these high-resolution structures for in silico screening may be limited. Recent molecular docking studies using the $\beta_2AR$ crystal structure as a template identified six new $\beta_2AR$ ligands that bind with affinities ranging from 9 nM to 4 µM; however, every compound exhibited inverse agonist activity. Beyond the crystallization of more GPCRs, methods for acquiring structures of receptors bound to different classes of ligands including agonists, antagonists, allosteric regulators and/or G proteins must be developed. For example, agonist-bound receptor crystals may provide three-dimensional representations of the active states of GPCRs. These structures will help clarify the conformational changes connecting the ligand-binding and G-protein-interaction sites, and lead to more precise mechanistic hypotheses and eventually new therapeutics. Given the conformational flexibility inherent to ligand-activated GPCRs and the greater heterogeneity exhibited by agonist-bound receptors, stabilizing such a state is not easy. Such efforts can benefit from the stabilization of the agonist-bound receptor conformation by the addition of protein binding domains that are specific for an active conformational state of the receptor. Especially suited are nanobodies that show G-protein-like behavior and exhibit cooperative properties with respect to agonist binding, as are provided herein (see Example section).

Accordingly, also provided is a method of determining a crystal structure of a GPCR in a functional conformational state, the method comprising the steps of:
  (i) providing a protein binding domain hereof, a target GPCR, and optionally a receptor ligand,
  (ii) forming a complex of the protein binding domain, the GPCR, and optionally the receptor ligand, and
  (iii) crystallizing the complex of step (ii) to form a crystal, wherein the crystal structure is determined of a GPCR in a functional conformational state, preferably the active conformational state.

Determining the crystal structure may be done by a biophysical method such as X-ray crystallography. The method may further comprises a step of obtaining the atomic coordinates of the crystal (as defined hereinbefore).

Capturing and/or Purifying a GPCR in a Functional Conformational State

In yet another embodiment, provided is a method for capturing and/or purifying a GPCR in a functional conformational state, preferably an active conformational state, by making use of any of the above-described protein binding domains, or complexes or cellular compositions comprising such protein binding domains. Capturing and/or purifying a GPCR in a functional conformational state, preferably an active conformational state, hereof, will allow subsequent crystallization, ligand characterization and compound screening, and immunizations, amongst others. In practice, such methods and techniques include, without limitation, affinity-based methods such as affinity chromatography, affinity purification, immunoprecipitation, protein detection, immunochemistry, and surface-display, amongst others, and are all well known by the skilled in the art.

Thus, described is the use of a protein binding domain hereof, or a complex or a cellular composition comprising the same as described hereinbefore, to capture a GPCR in a functional conformational state, preferably to capture a GPCR in its active conformational state. Optionally, but not necessarily, capturing of a GPCR in its functional conformational state as described above may include capturing a GPCR in a functional conformational state in complex with a receptor ligand or one or more downstream interacting proteins.

Accordingly, also provided is a method of capturing a GPCR in a functional conformational state, the method comprising the steps of:
  (i) providing a protein binding domain hereof and a target GPCR, and,
  (ii) forming a complex of the protein binding domain and the GPCR,
  wherein a GPCR is captured in a functional conformational state, preferably an active conformational state.

More specifically, also provided is a method of capturing a GPCR in a functional conformational state, the method comprising the steps of:
  (i) applying a solution containing a GPCR in a plurality of conformational states to a solid support possessing an immobilized protein binding domain hereof,
  (ii) forming a complex of the protein binding domain and the GPCR, and
  (iii) removing weakly bound or unbound molecules,
  wherein a GPCR is captured in a functional conformational state, preferably an active conformational state.

It will be appreciated that any of the methods as described above may further comprise the step of purifying the complex of the protein binding domain and the GPCR in its functional conformational state.

Therapeutic and Diagnostic Applications

Traditionally, small molecules are used for development of drugs directed against GPCRs, not only because pharmaceutical companies have historical reasons to work with these, but, more importantly, because of the structural constraints of Family 1 GPCRs, which have the ligand binding site within the transmembrane cleft (*Nat. Rev. Drug Discov.* (2004), the state of GPCR research in 2004, Nature Reviews Drug Discovery GPCR Questionnaire Participants 3(7):575, 577-626). For this reason, it proved to be difficult or impossible to generate monoclonal antibodies against this target class. The protein binding domains hereof, in particular, the nanobodies, can solve this particular problem by means of their intrinsic property of binding via extended CDR loops into cavities.

Accordingly, a fifth aspect hereof relates to a pharmaceutical composition comprising a therapeutically effective amount of a protein binding domain hereof and at least one of a pharmaceutically acceptable carrier, adjuvant or diluent.

A "carrier" or "adjuvant," in particular, a "pharmaceutically acceptable carrier" or "pharmaceutically acceptable adjuvant" is any suitable excipient, diluent, carrier and/or adjuvant that, by themselves, do not induce the production of antibodies harmful to the individual receiving the composition nor do they elicit protection. So, pharmaceutically acceptable carriers are inherently non-toxic and nontherapeutic, and they are known to the person skilled in the art. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Carriers or adjuvants may be, as a non-limiting example, Ringer's solution, dextrose solution or Hank's solution. Non-aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

The administration of a protein binding domain hereof or a pharmaceutical composition thereof may be by way of oral, inhaled or parenteral administration. In particular embodiments, the protein binding domain is delivered through intrathecal or intracerebroventricular administration. The active compound may be administered alone or preferably formulated as a pharmaceutical composition. An amount effective to treat a certain disease or disorder that express the antigen recognized by the protein binding domain depends on the usual factors such as the nature and severity of the disorder being treated and the weight of the mammal. However, a unit dose will normally be in the range of 0.1 mg to 1 g, for example, to 0.1 to 500 mg, for example, 0.1 to 50 mg, or 0.1 to 2 mg of protein binding domain or a pharmaceutical composition thereof. Unit doses will normally be administered once a month, once a week, biweekly, once or more than once a day, for example, two, three, or four times a day, more usually one to three times a day. It is greatly preferred that the protein binding domain or a pharmaceutical composition thereof is administered in the form of a unit-dose composition, such as a unit dose oral, parenteral, or inhaled composition. Such compositions are prepared by admixture and are suitably adapted for oral, inhaled or parenteral administration, and as such, may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycolate. Suitable lubricants include, for example, magnesium stearate. Suitable pharmaceutically acceptable wetting agents include sodium lauryl sulphate. These solid oral compositions may be prepared by conventional methods of blending, filling, tableting, or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents (for example, sorbitol, syrup, methyl cellulose, gelatin, hydroxyethylcellulose, carboxymethyl cellulose, aluminium stearate gel or hydrogenated edible fats), emulsifying agents (for example, lecithin, sorbitan monooleate, or acacia), non-aqueous vehicles (which may include edible oils, for example, almond oil, fractionated coconut oil, oily esters such as esters of glycerine, propylene glycol, or ethyl alcohol), preservatives (for example, methyl or propyl p-hydroxybenzoate or sorbic acid), and, if desired, conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case, the particles of active compound suitably have diameters of less than 50 microns, preferably less than 10 microns, for example between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg. For parenteral administration, fluid unit dose forms are prepared containing a compound hereof and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines (such as isoprenaline, isoetharine, salbutamol, phenylephrine and ephedrine), xanthine derivatives (such as theophylline and aminophylline), corticosteroids (such as prednisolone), and adrenal stimulants (such as ACTH) may be included. As is common practice, the compositions will usually be accompanied by written or printed directions for use in the medical treatment concerned.

Delivery of protein binding domains, in particular nanobodies, into cells may be performed as described for peptides, polypeptides and proteins. If the antigen is extracellular or an extracellular domain, the protein binding domain may exert its function by binding to this domain, without need for intracellular delivery. The protein binding domains hereof as described herein may target intracellular conformational epitopes of GPCRs of interest. To use these protein binding domains as effective and safe therapeutics inside a cell, intracellular delivery may be enhanced by protein transduction or delivery systems known in the art. Protein transduction domains (PTDs) have attracted considerable interest in the drug delivery field for their ability to translocate across biological membranes. The PTDs are relatively short (one- to 35-amino acid) sequences that confer this apparent translocation activity to proteins and other macromolecular cargo to which they are conjugated, complexed or fused (Sawant and Torchilin 2010). The HIV-derived TAT peptide (YGRKKRRQRRR (SEQ ID NO:71), for example, has been used widely for intracellular delivery of various agents ranging from small molecules to proteins, peptides, range of pharmaceutical nanocarriers and imaging agents. Alternatively, receptor-mediated endocytic mechanisms can also be used for intracellular drug delivery. For example, the transferrin receptor-mediated internalization pathway is an efficient cellular uptake pathway that has been exploited for site-specific delivery of drugs and proteins (Qian et al. 2002). This is achieved either chemically by conjugation of transferrin with therapeutic drugs or proteins or genetically by infusion of therapeutic peptides or proteins into the structure of transferrin. Naturally existing proteins (such as the iron-binding protein transferrin) are very useful in this area of drug targeting since these proteins are biodegradable, nontoxic, and non-immunogenic. Moreover, they can achieve site-specific targeting due to the high amounts of their receptors present on the cell surface. Still other delivery systems include, without the purpose of being limitative, polymer- and liposome-based delivery systems.

The efficacy of the protein binding domains hereof, and of compositions comprising the same, can be tested using any suitable in vitro assay, cell-based assay, in vivo assay and/or animal model known per se, or any combination thereof, depending on the specific disease or disorder involved.

A sixth aspect hereof relates to the use of the protein binding domain or the pharmaceutical composition as described hereinbefore to modulate GPCR signaling activity.

The protein binding domains hereof as described herein may bind to the GPCR so as to activate or increase receptor signaling, or, alternatively, so as to decrease or inhibit receptor signaling. The protein binding domains hereof may also bind to the GPCR in such a way that they block off the constitutive activity of the GPCR. The protein binding domains hereof may also bind to the GPCR in such a way that they mediate allosteric modulation (e.g., bind to the GPCR at an allosteric site). In this way, the protein binding domains hereof may modulate the receptor function by binding to different regions in the receptor (e.g., at allosteric sites). Reference is made, for example, to George et al. (2002), Kenakin (2002) and Rios et al. (2001). The protein binding domains hereof may also bind to the GPCR in such a way that they prolong the duration of the GPCR-mediated signaling or that they enhance receptor signaling by increasing receptor-ligand affinity. Further, the protein binding domains hereof may also bind to the GPCR in such a way that they inhibit or enhance the assembly of GPCR functional homomers or heteromers.

In one particular embodiment, the protein binding domain or the pharmaceutical composition as described hereinbefore blocks G-protein-mediated signaling.

In another embodiment, also envisaged is the protein binding domain or the pharmaceutical composition as described hereinbefore for use in the treatment of a GPCR-related disease, such as cancer, autoimmune disease, infectious disease, neurological disease, and cardiovascular disease.

Certain of the above-described protein binding domains may have therapeutic utility and may be administered to a subject having a condition in order to treat the subject for the condition. The therapeutic utility for a protein binding domain may be determined by the GPCR to which the protein binding domain binds in that signaling via that GPCR is linked to the condition. In certain cases, the GPCR may be activated in the condition by binding to a ligand. In other embodiments, the GPCR may be mutated to make it constitutively active, for example. A subject protein binding domain may be employed for the treatment of a GPCR-mediated condition such as schizophrenia, migraine headache, reflux, asthma, bronchospasm, prostatic hypertrophy, ulcers, epilepsy, angina, allergy, rhinitis, cancer, e.g., prostate cancer, glaucoma and stroke. Further exemplary GPCR-related conditions at the On-line Mendelian Inheritance in Man database can be found at the world wide website of the NCBI. A particular embodiment hereof also envisions the use of a protein binding domain or of a pharmaceutical composition for the treatment of a GPCR-related disease or disorder.

In a more specific embodiment, the protein binding domain may bind to the $\beta_2$-adrenergic receptor, in which case, it may be employed in the treatment of a condition requiring relaxation of smooth muscle of the uterus or vascular system. Such a protein binding domain may be thus used for the prevention or alleviation of premature labor pains in pregnancy, or in the treatment of chronic or acute asthma, urticaria, psoriasis, rhinitis, allergic conjunctivitis, acinitis, hay fever, or mastocytosis, which conditions have been linked to the $\beta_2$-adrenoreceptor. In these embodiments, the protein binding domain may be employed as co-therapeutic agents for use in combination with other drug substances such as anti-inflammatory, bronchodilatory or anti-histamine drug substances, particularly in the treatment of obstructive or inflammatory airway diseases such as those mentioned hereinbefore, for example, as potentiators of therapeutic activity of such drugs or as a means of reducing required dosaging or potential side effects of such drugs. A subject protein binding domain may be mixed with the other drug substance in a fixed pharmaceutical composition or it may be administered separately, before, simultaneously with or after the other drug substance. In general terms, these protocols involve administering to an individual suffering from a GPCR-related disease or disorder an effective amount of a protein binding domain that modulates a GPCR to modulate the GPCR in the host and treat the individual for the disorder.

In some embodiments, where a reduction in activity of a certain GPCR is desired, one or more compounds that decrease the activity of the GPCR may be administered, whereas when an increase in activity of a certain GPCR is desired, one or more compounds that increase the activity of the GPCR activity may be administered.

A variety of individuals are treatable according to the subject methods. Generally, such individuals are mammals or mammalian, where these terms are used broadly to describe organisms that are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans. Subject treatment methods are typically performed on individuals with such disorders or on individuals with a desire to avoid such disorders.

According to still another embodiment, the protein binding domain or the complex hereof may also be useful for the diagnosis or prognosis of a GPCR-related disease, such as cancer, autoimmune disease, infectious disease, neurological disease, or cardiovascular disease.

Identification of Compounds Selectively Targeting a GPCR in a Functional Conformational State In the process of compound screening, lead optimization and drug discovery, there is a requirement for faster, more effective, less expensive and especially information-rich screening assays that provide simultaneous information on various compound characteristics and their effects on various cellular pathways (i.e., efficacy, specificity, toxicity and drug metabolism). Thus, there is a need to quickly and inexpensively screen large numbers of compounds in order to identify new specific ligands of a GPCR of interest, preferably conformation-specific ligands, which may be potential new drug candidates. The present invention solves this problem by providing protein binding domains that stabilize and/or lock a GPCR in a functional conformational state, preferably an active conformational state, that can then be used as immunogens or selection reagents for screening in a variety of contexts. A major advantage of the protein binding domains hereof is that a GPCR can be kept in a stabilized functional conformation, preferably in an active state conformation. For example, library compounds that selectively bind this active conformation of the receptor have a higher propensity to behave as agonists because orthosteric or allosteric stabilization of the active conformation of the GPCR elicits biological responses. Another advantage is that the protein binding domain increases the thermostability of the active conformation of the GPCR, thus protecting the GPCR against irreversible or thermal denaturation induced by the non-native conditions used in compound screening and drug discovery, without the need to rely on mutant GPCRs with increased stability. Another major advantage of the conformation-selective protein binding domains hereof is that they quickly and reliably screen for and differentiate between receptor agonists, inverse agonists, antagonists and/or modulators as well as inhibitors of GPCRs and GPCR-dependent pathways, thereby increasing the likelihood of identifying a ligand with the desired pharmacological properties.

To illustrate this further, it is a well-established concept that most GPCRs exhibit higher agonist binding affinity when complexed with G protein. This is attributed to the cooperative interaction between agonist-occupied receptor and G protein (Delean et al. 1980). The protein binding domains hereof, in particular, the nanobodies, are capable of stabilizing an active conformational state of a GPCR (and thus show G-protein-like behavior) and destabilizing inactive conformational states, thus increasing the affinity of the GPCR for agonists and decreasing the affinity for inverse agonists or antagonists. It follows that the protein binding domains, such as nanobodies, hereof invention, that recognize the active functional conformation of the GPCR can be efficiently used in high-throughput screening assays to screen for agonists because they increase the affinity of the receptor for agonists, relative to inverse agonists or antagonists. Reciprocally, protein binding domains, in particular, nanobodies, that stabilize the inactive state conformation of a GPCR will increase the affinity for an inverse agonist or an antagonist and decrease the affinity for an agonist. Such protein binding domains may be used, for example, to screen for inverse agonists. Thus, protein binding domains, particularly nanobodies, that recognize particular functional conformational states, thus modulating the affinities for agonists and inverse agonists in a reciprocal way, also form part hereof.

Thus, according to a preferred embodiment, encompassed is the use of the protein binding domains, or the complexes, or the cellular compositions, all as described hereinbefore, in screening and/or identification programs for conformation-specific binding partners of a GPCR, which ultimately might lead to potential new drug candidates.

According to one embodiment, envisaged is a method of identifying compounds capable of selectively binding to a functional conformational state of a GPCR, the method comprising the steps of:
(i) Providing a GPCR and a protein binding domain capable of specifically binding to a functional conformational state of the GPCR hereof,
(ii) Providing a test compound,
(iii) Evaluating whether the test compound binds to the functional conformational state of the GPCR, and
(iv) Selecting a compound that selectively binds to the functional conformational state of the GPCR.

Preferably, the above method further comprises a step of forming a complex comprising the protein binding domain and the GPCR in a functional conformational state, more preferably, in an active conformational state.

Thus, the invention also envisages a method of identifying compounds capable of selectively binding to a functional conformational state of a GPCR, the method comprising the steps of:
(i) Providing a complex comprising a protein binding domain hereof and a GPCR in a functional conformational state,
(ii) Providing a test compound,
(iii) Evaluating whether the test compound binds to the functional conformational state of the GPCR, and
(iv) Selecting a compound that binds to the functional conformational state of the GPCR.

Preferably, the protein binding domain as used in any of the above methods is capable of stabilizing and/or inducing a functional conformational state of a GPCR upon binding. Preferably, the functional conformational state of a GPCR is selected from the group consisting of a basal conformational state, or an active conformational state or an inactive conformational state (as defined hereinbefore). Most preferably, the functional conformational state of a GPCR is an active conformational state.

In one other preferred embodiment, the protein binding domain as used in any of the above screening methods comprises an amino acid sequence that comprises four framework regions and three complementarity-determining regions, or any suitable fragment thereof. Preferably, the protein binding domain is derived from a camelid antibody. More preferably, the protein binding domain comprises a nanobody sequence, or any suitable fragment thereof. In particular, the nanobody comprises a sequence selected from the group consisting of SEQ ID NOS:1-29, or any suitable fragment thereof.

Other preferences for the protein binding domains and/or the complexes are as defined above with respect to the first and second aspect hereof.

In a preferred embodiment, the protein binding domain, the GPCR or the complex comprising the protein binding domain and the GPCR, as used in any of the above screening methods, are provided as whole cells, or cell (organelle) extracts such as membrane extracts or fractions thereof, or may be incorporated in lipid layers or vesicles (comprising natural and/or synthetic lipids), high-density lipoparticles, or any nanoparticle, such as nanodisks, or are provided as VLPs, so that sufficient functionality of the respective proteins is retained. Preparations of GPCRs formed from membrane fragments or membrane-detergent extracts are reviewed in detail in Cooper (2004), incorporated herein by reference. Alternatively, GPCRs and/or the complex may also be solubilized in detergents. Non-limiting examples of solubilized receptor preparations are further provided in the Example section.

Often, high-throughput screening of GPCR targets for conformation-specific binding partners will be preferred. This will be facilitated by immobilization of a protein binding domain hereof, a GPCR in a functional conformational state or a complex comprising them, onto a suitable solid surface or support that can be arrayed or otherwise multiplexed. Non-limiting examples of suitable solid supports include beads, columns, slides, chips or plates.

More particularly, the solid supports may be particulate (e.g., beads or granules, generally used in extraction columns) or in sheet form (e.g., membranes or filters, glass or plastic slides, microtiter assay plates, dipstick, capillary fill devices or the like), which can be flat, pleated, or hollow fibers or tubes. The following matrices are given as examples and are not exhaustive. Such examples could include silica (porous amorphous silica), i.e., the FLASH series of cartridges containing 60 A irregular silica (32-63 µm or 35-70 µm) supplied by Biotage (a division of Dyax Corp.), agarose or polyacrylamide supports, for example, the Sepharose range of products supplied by Amersham Pharmacia Biotech, or the Affi-Gel supports supplied by Bio-Rad. In addition, there are macroporous polymers, such as the pressure-stable Affi-Prep supports as supplied by Bio-Rad. Other supports that could be utilized include dextran, collagen, polystyrene, methacrylate, calcium alginate, controlled pore glass, aluminium, titanium and porous ceramics. Alternatively, the solid surface may comprise part of a mass-dependent sensor, for example, a surface plasmon resonance detector. Further examples of commercially available supports are discussed in, for example, *Protein Immobilization*, R. F. Taylor ed., Marcel Dekker, Inc., New York, (1991).

Immobilization may be either non-covalent or covalent. In particular, non-covalent immobilization or adsorption on a solid surface of the protein binding domain, the GPCR or the complex comprising the protein binding domain and the GPCR, hereof invention, may occur via a surface coating with any of an antibody, or streptavidin or avidin, or a metal ion, recognizing a molecular tag attached to the protein binding domain or the GPCR, according to standard techniques known by the skilled person (e.g., biotin tag, Histidine tag, etc.).

In particular, the protein binding domain, the GPCR or the complex comprising the protein binding domain and the GPCR, hereof, may be attached to a solid surface by covalent cross-linking using conventional coupling chemistries. A solid surface may naturally comprise cross-linkable residues suitable for covalent attachment or it may be coated or derivatized to introduce suitable cross-linkable groups according to methods well known in the art. In one particular embodiment, sufficient functionality of the immobilized protein is retained following direct covalent coupling to the desired matrix via a reactive moiety that does not contain a chemical spacer arm. Further examples and more detailed information on immobilization methods of antibody (fragments) on solid supports are discussed in Jung et al. (2008); similarly, membrane receptor immobilization methods are reviewed in Cooper (2004); both herein incorporated by reference.

Advances in molecular biology, particularly through site-directed mutagenesis, enable the mutation of specific amino acid residues in a protein sequence. The mutation of a particular amino acid (in a protein with known or inferred structure) to a lysine or cysteine (or other desired amino acid) can provide a specific site for covalent coupling, for example. It is also possible to reengineer a specific protein to alter the distribution of surface available amino acids involved in the chemical coupling (Kallwass et al. 1993), in effect controlling the orientation of the coupled protein. A similar approach can be applied to the protein binding domains hereof, as well as to the conformationally stabilized GPCRs, whether or not comprised in a complex, so as to provide a means of oriented immobilization without the addition of other peptide tails or domains containing either natural or unnatural amino acids. In case of an antibody or an antibody fragment, such as a nanobody, introduction of mutations in the framework region is preferred, minimizing disruption to the antigen-binding activity of the antibody (fragment).

Conveniently, the immobilized proteins may be used in immunoadsorption processes such as immunoassays, for example, ELISA, or immunoaffinity purification processes by contacting the immobilized proteins hereof with a test sample according to standard methods conventional in the art. Alternatively, and particularly for high-throughput purposes, the immobilized proteins can be arrayed or otherwise multiplexed. Preferably, the immobilized proteins hereof are used for the screening and selection of compounds that specifically bind to a GPCR in a functional conformational state, in particular, a GPCR in an active conformational state.

It will be appreciated that either the protein binding domain or the GPCR in a functional conformational state, or the complex comprising the protein binding domain and the GPCR, may be immobilized, depending on the type of application or the type of screening that needs to be done. Also, the choice of the GPCR-stabilizing protein binding domain (targeting a particular conformational epitope of the GPCR), will determine the orientation of the GPCR and, accordingly, the desired outcome of the compound identification, e.g., compounds specifically binding to extracellular parts, intramembranal parts or intracellular parts of the conformationally stabilized GPCR.

In an alternative embodiment, the test compound (or a library of test compounds) may be immobilized on a solid surface, such as a chip surface, whereas the protein binding domain, the GPCR or the complex are provided, for example, in a detergent solution or in a membrane-like preparation.

Most preferably, neither the protein binding domain, nor the GPCR, nor the test compound is immobilized, for example, in phage-display selection protocols in solution, or radioligand binding assays.

Various methods may be used to determine binding between the stabilized GPCR and a test compound, including, for example, enzyme-linked immunosorbent assays (ELISA), surface Plasmon resonance assays, chip-based assays, immunocytofluorescence, yeast two-hybrid technology and phage display, which are common practice in the art, for example, in Sambrook et al. (2001), *Molecular Cloning, A Laboratory Manual*, Third Edition, Cold Spring Harbor Laboratory Press, Cold Spring Harbor, N.Y. Other methods of detecting binding between a test compound and a GPCR include ultrafiltration with ion spray mass spectroscopy/HPLC methods or other (bio)physical and analytical methods. Fluorescence Energy Resonance Transfer (FRET) methods, for example, well known to those skilled in the art, may also be used. It will be appreciated that a bound test compound can be detected using a unique label or tag associated with the compound, such as a peptide label, a nucleic acid label, a chemical label, a fluorescent label, or a radio frequency tag, as described further herein.

In addition to establishing binding to a GPCR in a functional conformational state, it will also be desirable to determine the functional effect of a compound on the GPCR. In particular, the protein binding domains or the complexes or the cellular compositions as described herein can be used to screen for compounds that modulate (increase or decrease) the biological activity of the GPCR. The desired modulation in biological activity will depend on the GPCR of choice. The compounds to be tested can be any small chemical compound, or a macromolecule, such as a protein, a sugar, nucleic acid or lipid. Typically, test compounds will be small chemical compounds, peptides, antibodies or fragments thereof. It will be appreciated that in some instances high throughput screening of test compounds is preferred and that the methods as described above may be used as a "library screening" method, a term well known to those skilled in the art. Thus, the test compound may be a library of test compounds. In particular, high-throughput screening assays for therapeutic compounds such as agonists, antagonists or inverse agonists and/or modulators form part hereof. For high-throughput purposes, compound libraries may be used such as allosteric compound libraries, peptide libraries, antibody libraries, fragment-based libraries, synthetic compound libraries, natural compound libraries, phage-display libraries and the like. Methodologies for preparing and screening such libraries are known in the art.

In one preferred embodiment, high-throughput screening methods involve providing a combinatorial chemical or peptide library containing a large number of potential therapeutic ligands. Such "combinatorial libraries" or "compound libraries" are then screened in one or more assays, as described herein, to identify those library members (particular chemical species or subclasses) that display a desired characteristic activity. A "compound library" is a collection of stored chemicals usually used ultimately in high-throughput screening. A "combinatorial library" is a collection of diverse chemical compounds generated by either chemical synthesis or biological synthesis, by combining a number of chemical "building blocks" such as reagents. Preparation and screening of combinatorial libraries are well known to those of skill in the art. The compounds thus identified can serve as conventional "lead compounds" or can themselves be used as potential or actual therapeutics. Thus, in one further embodiment, the screening methods as described hereinabove further comprise modifying a test compound that has been shown to bind to a GPCR in a functional conformational state, preferably an active conformational state, and determining whether the modified test compound binds to the GPCR when residing in the particular conformation.

In a particular embodiment, the test compound is provided as a biological sample. In particular, the sample can be any suitable sample taken from an individual. For example, the sample may be a body fluid sample such as blood, serum, plasma, spinal fluid. Alternatively, the sample is tissue or cell extract.

The compounds may bind to the target GPCR resulting in the modulation (activation or inhibition) of the biological function of the GPCR, in particular, the downstream receptor signaling. This modulation of GPCR signaling can occur ortho- or allosterically. The compounds may bind to the target GPCR so as to activate or increase receptor signaling or, alternatively, so as to decrease or inhibit receptor signaling. The compounds may also bind to the target GPCR in such a way that they block off the constitutive activity of the GPCR. The compounds may also bind to the target complex in such a way that they mediate allosteric modulation (e.g., bind to the GPCR at an allosteric site). In this way, the compounds may modulate the receptor function by binding to different regions in the GPCR (e.g., at allosteric sites). Reference is made, for example, to George et al. (2002), Kenakin (2002) and Rios et al. (2001). The compounds hereof may also bind to the target GPCR in such a way that they prolong the duration of the GPCR-mediated signaling or that they enhance receptor signaling by increasing receptor-ligand affinity. Further, the compounds may also bind to the target complex in such a way that they inhibit or enhance the assembly of GPCR functional homomers or heteromers.

In one embodiment, it is determined whether the compound alters the binding of the GPCR to a receptor ligand (as defined herein). Binding of a GPCR to its ligand can be assayed using standard ligand binding methods known in the art as described herein. For example, a ligand may be radiolabeled or fluorescently labeled. The assay may be carried out on whole cells or on membranes obtained from the cells or aqueous-solubilized receptor with a detergent. The compound will be characterized by its ability to alter the binding of the labeled ligand (see also Example section). The compound may decrease the binding between the GPCR and its ligand, or may increase the binding between the GPCR and its ligand, for example, by a factor of at least two-fold, three-fold, four-fold, five-fold, ten-fold, twenty-fold, thirty-fold, fifty-fold, or one hundred-fold.

Thus, according to more specific embodiments, the complex as used in any of the above screening methods further comprises a receptor ligand. Preferably, the receptor ligand is chosen from the group comprising a small molecule, a polypeptide, an antibody or any fragment derived thereof, a natural product, and the like. More preferably, the receptor ligand is a full agonist, or a partial agonist, or an inverse agonist, or an antagonist, as described hereinbefore.

According to a specific embodiment, the protein binding domains hereof, particularly the nanobodies, can also be useful for lead identification and the design of peptidomimetics. Using a biologically relevant peptide or protein structure as a starting point for lead identification represents one of the most powerful approaches in modern drug discovery. Peptidomimetics are compounds whose essential elements (pharmacophore) mimic a natural peptide or protein in three-dimensional space and that retain the ability to interact with the biological target and produce the same biological effect. Peptidomimetics are designed to circumvent some of the problems associated with a natural peptide, for example, stability against proteolysis (duration of activity) and poor bioavailability. Certain other properties, such as receptor selectivity or potency, often can be substantially improved. By means of a non-limiting example, the nanobodies hereof may bind with long CDR loops deep into the core of the receptor to exert a biological effect. These peptides and their concomitant structures in the nanobody-GPCR complex can serve as starting points for lead identification and the design of peptidomimetics.

Accordingly, the protein binding domains, in particular, the nanobodies hereof, can be useful in screening assays. Screening assays for drug discovery can be solid phase or solution phase assays, e.g., a binding assay, such as radio-ligand binding assays. In high-throughput assays, it is possible to screen up to several thousand different modulators or ligands in a single day in 96-, 384- or 1536-well formats. For example, each well of a microtiter plate can be used to run a separate assay against a selected potential modulator, or, if concentration or incubation time effects are to be observed, every five to ten wells can test a single modulator. Thus, a single standard microtiter plate can assay about 96 modulators. It is possible to assay many plates per day; assay screens for up to about 6,000, 20,000, 50,000, or more, different compounds are possible today.

Further, the protein binding domains, such as the nanobodies hereof, can also be useful in cell-based assays. Cell-based assays are also critical for assessing the mechanism of action of new biological targets and biological activity of chemical compounds. Current cell-based assays for GPCRs include measures of pathway activation ($Ca^{2+}$ release, cAMP generation or transcriptional activity); measurements of protein trafficking by tagging GPCRs and downstream elements with GFP; and direct measures of interactions between proteins using Förster resonance energy transfer (FRET), bioluminescence resonance energy transfer (BRET) or yeast two-hybrid approaches. Introducing the protein binding domains, in particular, the nanobodies hereof, inside the cell to the relevant compartment of the cell (intra- or extracellularly) by any means well known and commonly used in the art, may lead to new or better cell-based assays.

In particular, there is a need to "de-orphanize" those GPCRs for which a natural activating ligand has not been identified. The stabilization of GPCRs in a functional conformational state using the protein binding domains hereof enables screening approaches that may be used to identify ligands of "orphan" GPCRs where the natural ligand is unknown. Ligands of orphan GPCRs may be identified from biological samples such as blood or tissue extract or from libraries of ligands. For example, various approaches to "de-orphanization" have been adopted including array-screening against families of known ligands.

The efficacy of the compounds and/or compositions comprising the same, can be tested using any suitable in vitro assay, cell-based assay, in vivo assay and/or animal model known per se, or any combination thereof, depending on the specific disease or disorder involved.

Accordingly, in one specific embodiment, a solid support to which is immobilized a protein binding domain hereof and/or a complex comprising a protein binding domain and a GPCR in a functional conformational state, is provided for use in any of the above screening methods.

In one embodiment, the test compound as used in any of the above screening methods is selected from the group comprising a polypeptide, a peptide, a small molecule, a natural product, a peptidomimetic, a nucleic acid, a lipid, lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or nanobody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, or engineered CH2 domains (nanoantibodies), as defined hereinbefore.

The test compound may optionally be covalently or non-covalently linked to a detectable label. Suitable detectable labels and techniques for attaching, using and detecting them will be clear to the skilled person, and include, but are not limited to, any composition detectable by spectroscopic, photochemical, biochemical, immunochemical, electrical, optical or chemical means. Useful labels include magnetic beads (e.g., dynabeads), fluorescent dyes (e.g., all Alexa Fluor dyes, fluorescein isothiocyanate, Texas red, rhodamine, green fluorescent protein and the like), radiolabels (e.g., $^3$H, $^{125}$I, $^{35}$S, $^{14}$C, or $^{32}$P), enzymes (e.g., horse radish peroxidase, alkaline phosphatase), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Other suitable detectable labels were described earlier within the context of the first aspect hereof relating to a protein binding domain.

In a preferred embodiment, the test compound is an antibody or any fragment derived thereof, as described above, including a nanobody. For example, and without the purpose of being limitative, the test compound may be an antibody (as defined herein in its broadest sense) that has been raised against a complex comprising a protein binding domain hereof and a GPCR (including variants, as described hereinbefore) in a functional conformational state, preferably in an active conformational state. Methods for raising antibodies in vivo are known in the art. Preferably, immunization of an animal will be done in a similar way as described hereinbefore (immunization with GPCR in presence of receptor ligand; see also Example section) with a GPCR in the presence of a functional conformational state stabilizing protein binding domain, more preferably, an active state stabilizing protein binding domain. The invention also relates to methods for selecting antibodies specific to a GPCR in a functional conformational state, preferably an active conformational state, involving the screening of expression libraries encoding immunoglobulin genes, or portions thereof, expressed in bacteria, yeast, filamentous phages, ribosomes or ribosomal subunits or other display systems on a complex containing a GPCR and a protein binding domain that stabilizes a functional conformational state of the GPCR.

A seventh aspect hereof relates to a kit comprising a protein binding domain hereof or a complex hereof or a cellular composition hereof. The kit may further comprise a combination of reagents such as buffers, molecular tags, vector constructs, reference sample material, as well as suitable solid supports, and the like. Such a kit may be useful for any of the applications hereof as described herein. For example, the kit may comprise (a library of) test compounds useful for compound screening applications.

Finally, a last aspect hereof is the use of any protein binding domain hereof to isolate amino acid sequences that are responsible for specific binding to a conformational epitope of a functional conformational state of a GPCR, in particular, an active conformational state of a GPCR and to construct artificial protein binding domains based on the amino acid sequences. It will be appreciated that in the protein binding domains hereof, the framework regions and the complementarity-determining regions are known, and the study of derivatives of the protein binding domain, binding to the same conformational epitope of a functional conformational state of a GPCR, in particular, an active conformational state of a GPCR, will allow deducing the essential amino acids involved in binding the conformational epitope. This knowledge can be used to construct a minimal protein binding domain and to create derivatives thereof, which can routinely be done by techniques known by the skilled in the art.

The following examples are intended to promote a further understanding hereof. While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

EXAMPLES

Protein Binding Domains Stabilizing Functional Conformational States of Human $\beta_2$AR Example 1. Immunization, Library Construction and Initial Screening To obtain in vivo matured nanobodies against $\beta_2$AR, a llama (*Llama glama*) was immunized with recombinant $\beta_2$AR truncated at Gly365 ($\beta_2$AR-365) to exclude an immune response to the carboxyl terminus. $\beta_2$AR-365 was expressed in insect cells and antigen was reconstituted as previously described (Day et al. 2007). After six weekly administrations of the reconstituted truncated agonist-bound receptor, lymphocytes were isolated from the blood of the immunized llama and a phage library prepared and screened as described in Materials and Methods to the Examples (see further). Two screens identified conformational nanobodies that recognize the native β₂AR, but not the denatured receptor.

Example 2. Selection of Conformational-Specific Nanobodies by ELISA

In a first screen we compared the binding of the nanobodies on the native and heat denatured β₂AR antigen in an ELISA. For each nanobody, one well was coated with phospholipid vesicles containing agonist-bound β₂AR-365 (0.1 μg protein/well). Next, this plate was incubated at 80° C. for two hours. Next, another well of the same plate was coated with phospholipid vesicles containing agonist-bound β₂AR-365 (0.1 μg protein/well) without heating. All of the nanobodies were able to selectively bind the native receptor but not the heat inactivated receptor, indicating that 16 binders recognize conformational epitopes.

Example 3. Selection of Conformational-Specific Nanobodies by Dot Blot

In a next screen we compared the specificity of the nanobodies for a native agonist-bound β₂AR receptor, versus a native inverse agonist-bound receptor, versus an SDS denaturated receptor by dot blot analysis. The screen identified 16 different conformational nanobodies that recognize native agonist-bound β₂AR-365, but not the inverse agonist, or the heat denatured receptor (FIG. 2 (dot blots)).

Example 4. Selection of Nanobodies with G Protein-Like Behavior

The initial screen identified 16 clones that recognized native agonist-bound β₂AR, but not heat denatured receptor. Our next goal was to identify nanobodies that had G protein-like behavior. The β₂AR preferentially couples to Gs and agonist binding enhances G protein interactions. Moreover, in the presence of Gs, the β₂AR binds agonist with higher affinity. Therefore, we looked at (1) the effect of agonist on nanobody binding to the β₂AR using size exclusion chromatography, (2) the effect of nanobodies on β₂AR agonist binding affinity in membranes and (3) the effect of nanobodies on β₂AR conformational changes as monitored by the environmentally sensitive monobromobimane (mBBr) fluorophore.

Figure 1:
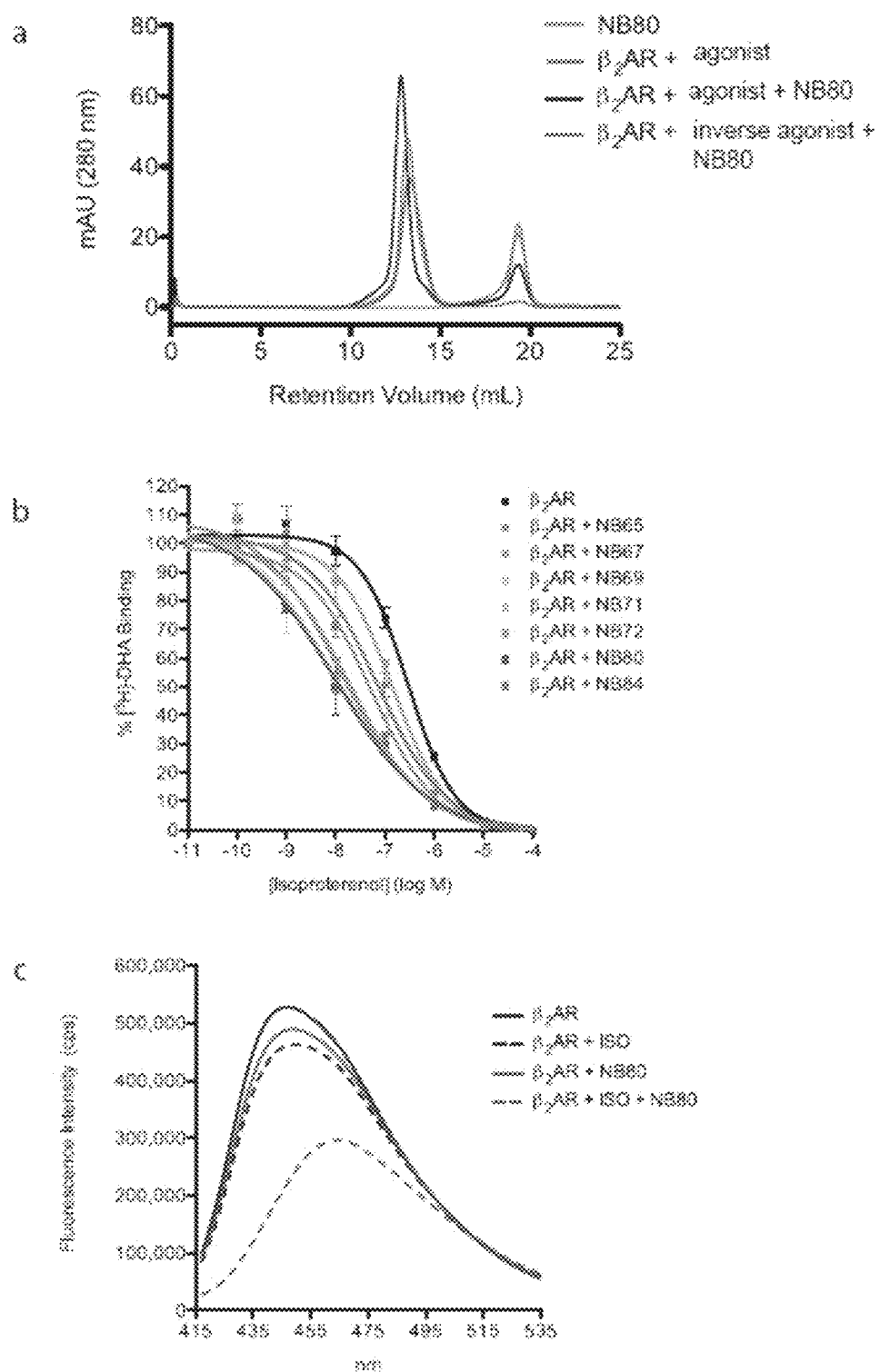
FIG. 1. $\beta_2$AR-specific nanobodies bind and stabilize an active state of the receptor.

Example 5. Nanobodies with G Protein-Like Behavior Specifically Bind to Purified Agonist-Bound Receptor Purified nanobodies were incubated with purified, detergent-solubilized β₂AR receptor in the presence of an agonist or an inverse agonist that stabilizes an inactive conformation. The mixture was then analyzed by Size Exclusion Chromatography (SEC), which separates protein on the basis of size. Seven of the nanobodies bound to purified β₂AR and migrated as a complex on SEC only in the presence of agonist and not an inverse agonist (an example is shown in FIG. 1, Panel a, FIGS. 3A, 3B, and FIG. 4). The remaining nanobodies did not bind with sufficient high affinity to shift the mobility of the β₂AR on SEC.

Example 6. Nanobodies with G Protein-Like Behavior Enhance the Affinity of β₂AR for Agonists Many GPCRs exhibit higher agonist binding affinity when complexed with G protein. This is attributed to the cooperative interaction between agonist occupied receptor and G protein. Our SEC experiments provide evidence that seven nanobodies preferentially bind to agonist occupied β₂AR and may therefore stabilize an active state in a manner similar to the G protein Gs. Agonist competition binding experiments were performed in the presence and absence of these seven nanobodies. The affinity of the β₂AR for the agonist (isoproterenol) was enhanced two- to thirty-fold in the presence of nanobodies 65, 67, 69, 71, 72, 80 and 84 (FIG. 1, Panel b, and Table 1). In contrast, Nb80 does not increase the affinity of β₂AR or β₂AR-T4L for the inverse agonist ICI-118,551 (ICI) (FIG. 15).

Example 7. Nb80 and the G Protein Induce Similar Conformational Changes at the Cytoplasmic Domain of TM6

The recent crystal structure of opsin as well as biophysical studies on rhodopsin (Park et al. 2008) and the β₂AR (Yao et al. 2009) show that the cytoplasmic end of transmembrane segment 6 (TM6) undergoes conformational changes upon agonist binding that are required for G protein coupling. To investigate the effect of nanobodies on movement of the cytoplasmic domain of TM6 we labeled purified β₂AR at C265 with monobromobimane (mBB-β₂AR). We previously showed that both agonist binding and G protein coupling-induced changes in the fluorescence of mBB-β₂AR compatible with an outward movement of TM6 (Yao et al. 2008) as observed in the opsin crystal structure (Park et al. 2008). In mBB-β₂AR, the addition of agonist together with G protein results in larger fluorescent changes than either agonist or G protein alone. This is compatible with the cooperative interactions observed in agonist competition binding assays (Yao et al. 2009). Similarly, relatively small changes in fluorescence were observed in mBB-β₂AR with the addition of either the agonist isoproterenol alone or Nb80 alone; however, larger changes were observed when both agonist and nanobody were added together (FIG. 1, Panel c). Comparable results were observed for nanobodies 65, 67, 69, 71, 72 and 84 (FIGS. 5A-5F).

Example 8. Characterization of the Nanobody-Stabilized β₂AR Active State

We then compared the effect of Nb80 with Gs on β₂AR structure and agonist binding affinity. β₂AR was labeled at the cytoplasmic end of TM6 at C265 with monobromobimane and reconstituted into HDL particles. TM6 moves relative to TM3 and TM5 upon agonist activation (FIG. 6, Panel A), and we have previously shown that the environment around bimane covalently linked to C265 changes with both agonist binding and G protein coupling, resulting in a decrease in bimane intensity and a red shift in $\lambda_{max}$ (Yao et al. 2009). The change in bimane fluorescence is compatible with movements of TM6 similar to those observed in rhodopsin by DEER spectroscopy and in the structure of low pH opsin. As shown in FIG. 6, Panel B, the catecholamine agonist isoproterenol and Gs both stabilize an active-like conformation, but the effect of Gs is greater in the presence of isoproterenol, consistent with the cooperative interactions of agonist and Gs on β₂AR structure. Nb80 alone has an effect on bimane fluorescence and $\lambda_{max}$ of unliganded β₂AR this is similar to that of Gs (FIG. 6, Panel C). This effect was not observed in β₂AR bound to the inverse agonist ICI-118, 551. The effect of Nb80 was increased in the presence of 10 μM isoproterenol. These results show that Nb80 does not recognize the inactive conformation of the β₂AR, but binds efficiently to agonist occupied $\beta_2AR$ and produces a change in bimane fluorescence that is indistinguishable from that observed in the presence of Gs and isoproterenol.

FIG. 6, Panels D and E, show the effect of Gs and Nb80 on agonist affinity for $\beta_2AR$. $\beta_2AR$ was reconstituted into HDL particles and agonist competition binding experiments were performed in the absence or presence of Nb80 and Gs. In the absence of either protein, isoproterenol has an inhibition constant (Ki) of 107 nM. In the presence of Gs two affinity states are observed, because not all of the $\beta_2AR$ is coupled to Gs. In the Gs-coupled state, the affinity of isoproterenol increases by 100-fold (Ki=1.07 nM) (FIG. 6, Panel D, and Table 4). Similarly, in the presence of Nb80 the affinity of isoproterenol increases by 95-fold (Ki=1.13 nM) (FIG. 6, Panel E, and Table 4). These binding data suggest that Nb80 stabilizes a conformation in WT $\beta_2AR$ that is very similar to that stabilized by Gs, such that the energetic coupling of agonist and Gs binding is faithfully mimicked by Nb80.

The high-resolution structure of the inactive state of the $\beta_2AR$ was obtained with a $\beta_2AR$-T4L fusion protein. We previously showed that $\beta_2AR$-T4L has a higher affinity for isoproterenol than WT $\beta_2AR$ (Rosenbaum et al. 2007). Nevertheless, in the presence of Nb80 the affinity increased by 60-fold, resulting in an affinity (Ki=0.56 nM) comparable to that of WT $\beta_2AR$ bound to Nb80 (FIG. 6, Panel F, and Table 4). While we cannot study G protein coupling in $\beta_2AR$-T4L due to steric hindrance by T4L, the results show that T4L does not prevent binding of Nb80, and the nearly identical Ki values for agonist binding to wild-type $\beta_2AR$ and $\beta_2AR$-T4L in the presence of Nb80 suggest that Nb80 stabilizes a similar conformation in these two proteins.

Example 9. Nanobodies Facilitate Crystallization of Agonist-Bound $\beta_2AR$

The $\beta_2AR$ was originally crystallized bound to the inverse agonist carazolol using two different approaches. The first crystals were obtained from $\beta_2AR$ bound to a Fab fragment that recognized an epitope composed of the amino and carboxyl terminal ends of the third intracellular loop connecting TMs 5 and 6 (Rasmussen et al. 2007). In the second approach, the third intracellular loop was replaced by T4 lysozyme ($\beta_2AR$-T4L) (Rosenbaum et al. 2007). Efforts to crystallize $\beta_2AR$-Fab complex and $\beta_2AR$-T4L bound to different agonists failed to produce crystals of sufficient quality for structure determination.

We, therefore, attempted to crystallize agonist-bound $\beta_2AR$ and $\beta_2AR$-T4L in complex with Nb80. While crystals of both complexes were obtained in lipid bicelles and lipidic cubic phase (LCP), high-resolution diffraction was obtained from crystals of $\beta_2AR$-T4L-Nb80 grown in LCP. These crystals grew at pH 8.0 in 39% to 44% PEG400, 100 mM Tris, 4% DMSO, and 1% 1,2,3-heptanetriol.

Example 10. Nb80 Contributes to the Packing of $\beta_2AR$ in a Crystal Lattice

High-resolution diffraction was obtained from crystals of $\beta_2AR$-T4L-Nb80 grown in LCP. These crystals grew at pH 8.0 in 39% to 44% PEG400, 100 mM Tris, 4% DMSO, and 1% 1,2,3-heptanetriol.

A merged data set at 3.5 Å was obtained from 23 crystals (Table 5). The structure was solved by molecular replacement using the structures of the carazolol-bound $\beta_2AR$ and a nanobody as search models. FIG. 7 shows the packing of the $\beta_2AR$-T4L-Nb80 complex in the crystal lattice. Nb80 binds to the cytoplasmic end of the $\beta_2AR$, with the third complementarity-determining region (CDR) loop projecting into the core of the receptor. The $\beta_2AR$-nanobody complexes are arranged with the lipid bilayers approximately parallel to the be plane of the crystal. Two-fold symmetry-related nanobody molecules interact along the a axis to generate a tightly packed lattice in this direction. Within the bilayer, receptor molecules interact in an antiparallel arrangement with TM1, 2, 3 and 4 of one $\beta_2AR$ molecule packing against TM4 and 5 of the adjacent molecule. Contacts are also made between helix 8 and TM5 of parallel lattice neighbor along the b axis, and between the extracellular portion of TM1 and the cytoplasmic end of TM6 of a third, antiparallel neighbor. The packing is weakest along the c axis, which may be due in part to non-specific interactions of the T4L with neighboring receptor and/or nanobody molecules. There is no interpretable electron density for the T4L, but given the visible ends of TM5 and TM6 the position of T4L is highly constrained. Presumably T4L adopts a number of orientations relative to the receptor, and perhaps a range of internal conformations due to its hinge motion (Zhang et al. 1995), that average out its density. Nonetheless, T4L likely contributes to the structure of the crystal since we were unable to produce crystals of the native $\beta_2AR$-nanobody complex under these conditions, although it is possible that the flexible loop that connects TM5 and TM6 in the native receptor prevents lattice formation.

Example 11. Structure of a Nanobody-Stabilized Active State of $\beta_2AR$

FIG. 8 compares the inactive $\beta_2AR$ structure (from the carazolol-bound $\beta_2AR$-T4L structure) with the active state of $\beta_2AR$. The largest differences are found at the cytoplasmic face of the receptor, with outward displacement of TM5 and TM6 and an inward movement of TM7 and TM3 in the $\beta_2AR$-T4L-Nb80 complex relative to the inactive structure (FIG. 8, Panels A and B). There are relatively small changes in the extracellular surface (FIG. 8, Panel C). The second intracellular loop (ICL2) between TM3 and TM4 adopts a two-turn alpha helix, similar to that observed in the turkey $\beta_1AR$ structure (Warne et al. 2008). The absence of this helix in the inactive $\beta_2AR$ structure may reflect crystal lattice contacts involving ICL2.

FIG. 9, Panels A-C, show in greater detail the interaction of Nb80 with the cytoplasmic side of the $\beta_2AR$. An eight amino acid sequence of CDR 3 penetrates into a hydrophobic pocket formed by amino acids from TM segments 3, 5, 6 and 7. A four amino acid sequence of CDR1 provides additional stabilizing interactions with cytoplasmic ends of TM segments 5 and 6. FIG. 9, Panel D, compares the cytoplasmic surface of active and inactive conformations of the $\beta_2AR$. CDR3 occupies a position similar to the carboxyl terminal peptide of transducin in opsin (Scheerer et al. 2008) (FIG. 10). The majority of interactions between Nb80 and the $\beta_2AR$ are mediated by hydrophobic contacts.

When comparing the active and inactive structures, the largest change is observed in TM6, with an 11.4 Å movement of the helix at Glu268$^{6.30}$ (part of the ionic lock) (superscripts in this form indicate Ballesteros-Weinstein numbering for conserved GPCR residues (Ballesteros and Weinstein 1995) (FIG. 9, Panel D). This large change is effected by a small clockwise rotation of TM6 in the turn preceding the conserved Pro288$^{6.50}$, enabled by the interrupted backbone hydrogen bonding at the proline and repacking of Phe282$^{6.44}$ (see below), which swings the helix outward.

The changes in the active $\beta_2$AR-T4L-Nb80 relative to the inactive carazolol-bound $\beta_2$AR-T4L are remarkably similar to those observed between rhodopsin and opsin (Scheerer et al. 2008; Park et al. 2008) (FIG. 9, Panel E, and FIG. 10). The salt bridge in the ionic lock between highly conserved Arg131$^{3.50}$ and Asp/Glu130$^{3.49}$ is broken. In opsin, Arg135$^{3.50}$ interacts with Tyr223$^{5.58}$ in TM5 and a backbone carbonyl of the transducin peptide. Arg131$^{3.50}$ of $\beta_2$AR likewise interacts with a backbone carbonyl of CDR3 of Nb80. However, Nb80 precludes an interaction between Arg131$^{3.50}$ and Tyr219$^{5.58}$, even though the tyrosine occupies a similar position in opsin and the active conformation of $\beta_2$AR-T4L-Nb80. As in opsin, Tyr326$^{7.53}$ of the highly conserved NPxxY sequence moves into the space occupied by TM6 in the inactive state. In inactive carazolol-bound $\beta_2$AR-T4L we observed a network of hydrogen bonding interactions involving highly conserved amino acids in TMs 1, 2, 6 and 7 and several water molecules (Rosenbaum et al. 2007). While the resolution of the $\beta_2$AR-T4L-Nb80 is inadequate to detect waters, it is clear that the structural changes we observe would substantially alter this network.

In contrast to the relatively large changes observed in the cytoplasmic domains of $\beta_2$AR-T4L-Nb80, the changes in the agonist-binding pocket are fairly subtle. Trp$^{6.48}$ is highly conserved in Family A GPCRs, and it has been proposed that its rotameric state plays a role in GPCR activation (rotamer toggle switch) (Shi et al. 2002). We observe no change in the side chain rotamer of Trp286$^{6.48}$ in TM6, which lies near the base of the ligand-binding pocket, although its position shifts slightly due to rearrangements of nearby residues Ile121$^{3.40}$ and Phe282$^{6.44}$. While there is spectroscopic evidence for changes in the environment of Trp$^{6.48}$ upon activation of rhodopsin (Ahuja et al. 2009), a rotamer change is not observed in the crystal structures of rhodopsin and low-pH opsin. Moreover, recent mutagenesis experiments on the histamine receptor demonstrate that Trp$^{6.48}$ is not required for activation of the 5HT4 receptor by serotonin (Pellissier et al. 2009).

It is interesting to speculate how the small changes around the agonist-binding pocket are coupled to much larger structural changes in the cytoplasmic regions of TMs 5, 6 and 7 that facilitate binding of Nb80 and Gs. A potential conformational link is shown in FIG. 11. Agonist interactions may stabilize an active receptor conformation that includes a 2.1 Å inward movement of TM5 at position 207$^{5.46}$ and 1.4 Å inward movement of the conserved Pro211$^{5.50}$ relative to the inactive structure. In the inactive state, the relative positions of TM5, TM3, TM 6 and TM7 are stabilized by interactions between Pro211$^{5.50}$, Ile121$^{3.40}$, Phe282$^{6.44}$ and Asn318$^{7.45}$. The position of Pro211$^{5.50}$ observed in the active state is incompatible with this network of interactions, and Ile121$^{3.40}$ and Phe282$^{6.44}$ are repositioned, with a rotation of TM6 around Phe282$^{6.44}$ leading to an outward movement of the cytoplasmic end of TM6.

Although some of the structural changes observed in the cytoplasmic domains of the $\beta_2$AR-T4L-Nb80 complex arise from specific interactions with Nb80, the fact that Nb80 and Gs induce or stabilize similar structural changes in the $\beta_2$AR, as determined by fluorescence spectroscopy and by agonist binding affinity, suggests that Nb80 and Gs recognize similar agonist stabilized conformations. The observation that the cytoplasmic domains of rhodopsin and the $\beta_2$AR undergo similar structural changes upon activation provides further support that the agonist-bound $\beta_2$AR-T4L-Nb80 represents an active conformation and is consistent with a conserved mechanism of G protein activation.

However, the mechanism by which agonists induce or stabilize these conformational changes likely differs for different ligands and for different GPCRs. The conformational equilibria of rhodopsin and $\beta_2$AR differ, as shown by the fact that rhodopsin can adopt a fully active conformation in the absence of a G protein whereas $\beta_2$AR cannot. Thus, the energetics of activation and conformational sampling can differ among different GPCRs, which likely gives rise to the variety of ligand efficacies displayed by these receptors. An agonist need only disrupt one key intramolecular interaction needed to stabilize the inactive state, as constitutive receptor activity can result from single mutations of amino acids from different regions of GPCRs (Parnot et al. 2002). Thus, disruption of these stabilizing interactions either by agonists or mutations lowers the energy barrier separating inactive and active states and increases the probability that a receptor can interact with a G protein.

In conclusion, these above results demonstrate the ability to generate nanobodies that recognize and stabilize an agonist-bound state of a GPCR. In the case of the $\beta_2$AR, this nanobody-stabilized state is functionally similar to the state stabilized by the G protein Gs. Finally, nanobodies facilitated the formation of diffraction quality crystals. This approach is now applied to other GPCRs and other membrane proteins.

Example 12. Nb80 Stabilizes the Active State Conformation of Members of the Adrenergic Receptor Family Active state stabilizing Nanobodies that are cross-reactive to related receptors can be used as a tool to stabilize a conformational state of those related receptors. To demonstrate this principle, we analyzed if Nb80 selectively binds the active conformation of the human $\beta_1$AR receptor. $\beta_1$AR and $\beta_2$AR are closely related adrenergic receptors. Using the PISA server (Krissinel & Henrick, 2007) and based on the crystal structure of the Nb80-$\beta_2$AR complex, 30 $\beta_2$AR AA residues were identified to interact with Nb80 in the $\beta_2$AR-Nb80 interface. An amino acid sequence alignment (FIG. 17) indicates that 28 out of these 30 residues involved in the Nb80 interaction are conserved among $\beta_1$AR and $\beta_2$AR. The remaining interface residues are lysines in $\beta_2$AR and have been substituted by arginines in $\beta$1AR corresponding to conserved substitutions (shown in grey boxes in FIG. 17). It thus appears that both receptors share a very similar binding site for Nb80. Based on this analysis, we also measured the effect of Nb80 on the affinity of $\beta_1$AR for the agonist isoproterenol and the inverse agonist CGP20712A (FIG. 18). As for $\beta_2$AR, Nb80 also induced an increased affinity of isoproterenol for $\beta_1$AR (FIGS. 18A and 18C). Nb80 does not change the affinity for the antagonist CGP20712A (FIG. 18D), demonstrating the selective stabilization of the active state conformation of $\beta_1$AR by Nb80. No such effect of Nb80 was observed on unrelated receptors like the dopamine D1 receptor (data not shown).

Example 13. $\beta_2$AR Active State Stabilizing Nanobodies are Excellent Tools for Improved Agonist Screening Many GPCRs exhibit higher agonist binding affinity when complexed with G protein. This is attributed to the cooperative interaction between agonist occupied receptor and G protein. Nanobodies with G protein-like behavior likely enhance the affinity of $\beta_2$AR for agonists (see Example 6). This behavior may have important implications in the discovery of new agonists. For example, Nbs with G protein-like behavior may increase the apparent affinity of GPCRs for agonists, compared to antagonists. This may cause a bias towards agonists among the hits when a compound library is screened against such GPCR-Nb complex. To evaluate the applicability of this approach, we analyzed the effect of the $\beta_2AR$ active state stabilizing Nanobody Nb80 on the interaction of $\beta_2AR$ with several well known $\beta_2AR$ ligands in competition radioligand binding experiments (see materials and methods). Ten agonists and five antagonists were tested: (−)isoproterenol HCl (agonist), (−)-alprenolol (antagonist), salbutamol (partial agonist), ICI118551 (inverse agonist), carvedilol (antagonist), CGP12177A (antagonist), salmeterol xinafoate (full agonist), terbutaline hemisulfate salt (partial agonist), dobutamine hydrochloride (partial agonist), metaproterenol hemisulfate salt (agonist), procaterol hydrochloride (agonist), ritodrine hydrochloride (agonist), fenoterol hydrobromide (full agonist), formoterol fumarate dihydrate (agonist) and timolol maleate salt (antagonist), all purchased via Sigma Aldrich.

Ligand competition binding experiments were performed in the presence and absence of 500 nM of Nb80 on commercial membranes containing full-length human $\beta_2AR$. $^3$H-dihydroalprenolol (DHA) was used as the competing radioligand. Representative examples of ligand competition binding experiments are shown in FIGS. 16A and 16B. For all compounds, IC50 values were obtained in the presence of excess Nb80 and compared to the IC50s obtained in the presence of an irrelevant nanobody (negative control). (Table 6). Consistent with Examples 6, 8 and 12, we observe an increase in potency for all agonists when $\beta_2AR$ is in complex with Nb80. Such effect is not observed for antagonists or inverse agonists.

Example 14. Compound Library Screening Using a $\beta_2AR$ Active State Stabilizing Nanobody Locking the GPCR in a particular conformation has an advantage over using a non-conformationally stabilized target (representing a repertoire of conformations) in screening assay with the aim to identify compounds against that particular conformation, the so-called "druggable" target conformation. The conformational selective Nb80 allows the use of wild-type receptors consequently minimizing the potential risk of artificial conformational changes as a result of site-directed mutagenesis.

In order to demonstrate whether Nb80 facilitates the identification of ligands that selectively bind $\beta_2AR$ in its active conformation, a fragment library consisting of approximately 1500 distinct low molecular weight compounds (<300 Da) is screened for agonists using a competition radioligand binding assay. For this assay, membranes containing full length $\beta_2AR$ are preincubated with Nb80 or an irrelevant Nb (negative control) and added to 96-well plates containing library compounds and 2 nM of $^3$H-dihydroalprenolol (DHA) radioligand (see materials and methods). Library compounds that significantly displace the radioligand in the sample containing $\beta_2AR$ in complex with Nb80 as compared to the sample containing the irrelevant nanobody are compounds that preferentially bind the active conformation of the receptor. Library compounds that selectively bind the active conformation of the receptor have a high propensity to behave as agonists because orthosteric or allosteric stabilization of the active conformation of the GPCR elicits biological responses. Selected library compounds have to be further screened for agonism by measuring for example by G protein coupling, downstream signaling events ore physiological output.

Example 15. Thermostabilization of the $\beta_2AR$ Receptor with Nanobodies

Structural and functional studies on integral membrane proteins have long been hampered by their instability in detergent. Although expression and purification methods are appearing that allow for the generation of milligram quantities, achieving stability with these molecules is perhaps the most difficult hurdle to overcome. Purification necessitates a release of the membrane protein from the lipid bilayer by detergent solubilization, a process during which hydrophobic surfaces of the protein are coated with surfactant monomers to form a protein-detergent complex. However, the detergent belt formed around the protein is a poor replacement for the lipid bilayer. Thus, solubilization of membrane proteins often results in destabilization, unfolding and subsequent aggregation. Thermostabilization of membrane proteins can be achieved through site directed mutagenesis (Zhou & Bowie, 2000; Magnini et al. 2008). Here, we show that binding of conformational selective nanobodies represents an innovative alternative for the thermostabilization of detergent-solubilized GPCRs.

The effect of conformational selective nanobodies on the thermostability and the subsequent aggregation of the $\beta_2AR$ receptor was analyzed using a fluorescent thermal stability assay (FIG. 13) and size exclusion chromatography (FIGS. 14A and 14B). For these experiments, recombinant $\beta_2AR$ was expressed in Sf9 insect cells, solubilized 1% dodecylmaltoside, 100 mM NaCl, 20 mM Hepes pH 7.5 and protease inhibitors, and purified by M1 FLAG affinity chromatography (see Material and Methods to the Examples).

The fluorescent thermal stability assay makes use of the thiol-specific fluorochrome N-[4-(7-diethylamino-4-methyl-3-coumarinyl)phenyl]maleimide (CPM) to measure the chemical reactivity of the native cysteines embedded in the protein interior as a sensor for the overall integrity of the folder state of membrane proteins (Alexandrov et al. 2008). For the fluorescent thermal stability assay, detergent-solubilized receptor (in 0.1% dodecylmaltoside, 100 mM NaCl and 20 mM Hepes pH 7.5) was pre-incubated with isoproterenol (10 µM) in the presence or absence of a 2:1 molar excess of Nb80 for one hour at RT. Samples were then mixed with CPM fluorophore and incubated for two minutes at temperatures ranging from 10° C. to 94° C. and fluorescence emission was collected. Experiments were performed in triplicate and resulted in melting curves resembling the stability profiles obtained for the GPCR APJ (Alexandrov et al. 2008). Unfolding transitions could be described by a simple two-state model, including the native (folded) and the denaturated state, representing the lower and upper plateaus of the melting curves. Comparison of the melting curve of the agonist-bound receptor with the melting curve of agonist-bound receptor in complex with Nb80 indicates that the nanobody stabilizes the active conformation of $\beta_2AR$ by increasing the melting temperature (Tm) of the agonist-bound receptor by 12° C.

We also analyzed the effect of Nb80 on the thermal unfolding and aggregation of the agonist-bound receptor by size exclusion chromatography (SEC). For this experiment, dodecylmaltoside-solubilized receptor was pre-incubated with isoproterenol (10 µM) in the presence or absence of a 2:1 molar excess of Nb80 for 45 minutes at RT. Samples were next incubated for 10 minutes at increasing temperatures and subsequently analyzed by SEC (FIGS. 14A and 14B). Comparison of the different chromatograms indicates that Nb80 protects the agonist-bound receptor against temperature-induced aggregation.

Protein Binding Domains Stabilizing Functional Conformational States of Rat Angiotensin II Type 1a Receptor (AT1aR)

Example 16. Immunization, Library Construction and Initial Screening

To obtain in vivo matured nanobodies against rat AT1aR, two llamas (*Llama glama*) were immunized with a recombinant AT1aR-T4lysozyme (T4L) fusion truncated after Lys318 to exclude an immune response to the carboxyl terminus. AT1aR was expressed in insect cells (Shluka et al. 2006) and antigen was reconstituted in lipid vesicles as previously described (Day et al. 2007). One llama was immunized with angiotensin- (unbiased agonist-) bound receptor, one llama was immunized with the β-arrestin biased ligand TRV023 (Violin et al. 2010) bound to the receptor. After six weekly administrations of the reconstituted truncated agonist-bound receptor, lymphocytes were isolated from the blood of the immunized llama and a phage library prepared and screened as described in Materials and Methods to the Examples. Solid-phase ELISAs identified nanobodies that recognize the AT1a receptor.

Example 17. Selection of Conformational-Specific Nanobodies by ELISA

In a first screen we compare the binding of the purified nanobodies on the native and heat denatured rat AT1aR antigen in an ELISA. For each nanobody, one well is coated with receptor. Next, this plate is incubated at 80° C. for two hours. Next, another empty well of the same plate is coated with receptor without heating. Nanobodies that are able to selectively bind the native receptor but not the heat inactivated receptor recognize conformational epitopes.

Example 18. Selection of Conformational State-Specific Nanobodies by Dot Blot In a next screen we compare the binding of those nanobodies that bind conformational epitopes to an agonist-bound AT1aR receptor versus an antagonist-bound receptor by dot blot analysis. This screen identifies nanobodies that selectively recognize a conformation of an agonist-bound (active state) versus antagonist-bound (inactive state) receptor.

Example 19. Screening for AT1aR Nanobodies Selectively Stabilizing an Active Conformation of the Receptor In addition to the binding assay for AT1aR specificity (ELISA), purified Nanobodies are evaluated in a radioligand competition experiment similar to the radioligand assays described in Examples 6, 12, and 13. Nanobodies that increase the affinity of AT1aR to an agonist are considered to stabilize an active conformation of the receptor.

Protein Binding Domains Stabilizing Functional Conformational States of Rat $M_3$-Muscarinic Receptor

Example 20. Immunization, Library Construction and Initial Screening

To obtain in vivo matured nanobodies against rat M3R, a llama (*Llama glama*) was immunized with a recombinant M3R-T4lysozyme (M3R-T4L) fusion truncated at both N- and C-terminal sites to exclude an immune response to the termini. In M3R-T4L the third intracellular loop was replaced by T4lysosyme. M3R-T4L was expressed in insect cells and antigen was reconstituted as previously described (Day et al. 2007). After six weekly administrations of the reconstituted antagonist- (tiotropium-) bound receptor, lymphocytes were isolated from the blood of the immunized llama and a phage library prepared and screened as described in Materials and Methods to the Examples.

Example 21. Selection of Conformational-Specific Nanobodies by ELISA

In a first screen we compare the binding of the purified nanobodies on the native and heat denatured rat M3R antigen in an ELISA. For each nanobody, one well is coated with receptor. Next, this plate is incubated at 80° C. for two hours. Next, another empty well of the same plate is coated with receptor without heating. Nanobodies that are able to selectively bind the native receptor but not the heat inactivated receptor recognize conformational epitopes.

Example 22. Selection of Conformational State-Specific Nanobodies by Dot Blot In a next screen we compare the binding of those nanobodies that bind conformational epitopes to an agonist-bound M3 receptor versus an antagonist-bound receptor by dot blot analysis. This screen identifies nanobodies that selectively recognize a conformation of an agonist-bound (active state) versus antagonist-bound (inactive state) receptor.

Example 23. Screening for M3R Nanobodies Selectively Stabilizing an Active Conformation of the Receptor In addition to the binding assay for M3R specificity (ELISA), purified Nanobodies are evaluated in a radioligand competition experiment similar to the radioligand assays described in Examples 6, 12, and 13. Nanobodies that increase the affinity of M3R to an agonist are considered to stabilize an active conformation of the receptor.

Materials and Methods to Examples $\beta_2$AR Preparation $\beta_2$AR truncated after amino acid 365 ($\beta_2$AR-365) having an amino terminal Flag epitope tag was expressed in Sf9 insects cells and purified by sequential M1 antibody and alprenolol affinity chromatography as previously described (Kobilka 1995). Purified $\beta_2$AR-365 was immobilized on a Flag column (Sigma) and equilibrated with 10 column volumes of a mixture of 5 mg/ml DOPC (Avanti Polar Lipids) and 0.5 mg/ml Lipid A (Sigma) in 1% (w/v) octyl-glucoside (Anatrace), 100 mM NaCl, 20 mM Hepes pH 7.5, 2 mM CaCl2 and 1 μM agonist (e.g., isoproterenol). The $\beta_2$AR was then eluted in the same buffer containing EDTA. The concentration of the eluted $\beta_2$AR was adjusted to 5 mg/ml. This usually involved diluting the protein with the same buffer, but occasionally required concentrating the protein up to two-fold with an Amicon ultrafiltration cell (100 kDa pore). The protein was then dialyzed against phosphate buffered saline containing 1 μM agonist at 4° C. to remove detergent. The reconstituted protein was stored at −80° C. prior to use for immunization.

AT1aR Preparation

AT1aR with T4lysozyme fusion in the third loop was truncated after amino acid 318 (AT1aR-318). This construct has an amino terminal Flag epitope tag and a C-terminal tag of ten histidines. AT1aR-318 was expressed in Tni insect cells and solubilized in 20 mM Hepes, pH7.4, 1 M NaCl and 0.5% MNG for two hours at room temperature. The receptor was purified by sequential Ni-NTA and FLAG-M1 antibody affinity chromatography. Purified AT1aR was reconstituted in a mixture of 5 mg/ml DOPC (Avanti Polar Lipids) and 0.5 mg/ml Lipid A (Sigma) in 1% (w/v) octylglucoside (Anatrace), 100 mM NaCl, 20 mM Hepes pH 7.5, and 100 μM agonist (e.g., angiotensin II). The concentration of the eluted At1aR was adjusted to 1-2 mg/ml. The protein was then dialyzed against phosphate buffered saline containing 100 μM agonist at 4° C. to remove detergent. The reconstituted protein was stored at −80° C. prior to use for immunization.

M3 Receptor Preparation $M_3$-muscarinic receptor with an amino terminal FLAG epitope tag and carboxy-terminal hexahistidine tag was expressed in Sf9 insect cells in the presence of 1 μM atropine (Vasudevan et al. 1995). Receptor either had intracellular loop 3 deleted (M3RΔi3) or substituted with T4 lysozyme (M3R-T4L). Cells were centrifuged and then lysed by osmotic shock, and protein was solubilized in 1% dodecyl-maltoside, 0.1% cholesterol hemisuccinate, 750 mM sodium chloride, 20 mM HEPES pH 7.5. Solubilized receptor was then purified by nickel affinity chromatography followed by FLAG affinity chromatography. Purified protein was then separated by size exclusion chromatography to select monomeric receptor, which was reconstituted as described (Day et al. 2007).

Nanobody Selection Against $\beta_2$AR

A single *llama* received six weekly administrations of the reconstituted truncated $\beta_2$AR. Lymphocytes were isolated from the blood of the immunized *llama* and total RNA was prepared from these cells. The coding sequences of the nanobody repertoire were amplified by an RT-PCR and cloned into the phage display vector pMES4 (genbank GQ907248) (Conrath et al. 2001). $\beta_2$AR-specific phages were enriched by in vitro selection on Maxisorp (Nunc) 96-well plates coated with the reconstituted $\beta_2$AR-365 receptor. Antigen-bound phages were recovered from antigen-coated wells either with thriethylamine pH11 and neutralized with Tris-HCl pH7 or by the addition of freshly grown TG1 *E. coli* cells. After two rounds of bio-panning, 96 individual colonies were randomly picked and the nanobodies produced as a soluble HIS-tagged protein in the periplasm of the TG1 cells. Solid-phase ELISAs identified 16 different conformational nanobodies that recognize native agonist-bound $\beta_2$AR-365, but not the heat denatured receptor.

Nanobody Selection Against AT1aR

One single *llama* received six weekly administrations of the reconstituted AT1aR-318 bound to its agonist angiotensin. Another single *llama* received six weekly administrations of AT1aR-318 bound to a biased agonist TRV023. After immunization, lymphocytes from each *llama* were isolated separately from the blood. Total RNA was prepared from these cells. From each sample the coding sequences of the nanobody repertoire were amplified by RT-PCR and cloned separately (Conrath et al. 2001) into the phage display vector pMESy4-vector to generate two independent libraries. pMESy4 is a derivative of pMES4 (genbank GQ907248) carrying a C-terminal His6tag followed by the amino acids EPEA (De Genst et al. 2010, *J. Mol. Biol.* 402:326-343).

AT1aR-specific phage was enriched by in vitro selection on Maxisorp (Nunc) 96-well plates coated with the reconstituted truncated AT1aR receptor (a variant of the recombinant receptor without the T4L insertion) bound to angiotensin or to TRV023, respectively. Antigen-bound phage was recovered from antigen-coated wells by trypsin digestion. After two rounds of bio-panning, 92 individual colonies (46 on AT1aR-angiotensin and 46 on AT1aR-TRV023) were randomly picked and the nanobodies were produced as a soluble HisIS-EPEA-tagged protein in the periplasm of the TG1 cells.

Nanobody Selection Against M3R

One single *llama* received six weekly administrations of reconstituted truncated M3R-T4L bound to the antagonist tiotropium. After immunization, lymphocytes from this *llama* were isolated from the blood and total RNA was prepared from these cells. The coding sequences of the nanobody repertoire were amplified by RT-PCR and cloned (Conrath et al. 2001) into the phage display vector pMESy4-vector.

To enrich for M3R-specific phages different in vitro selection strategies were followed using different formats of the antigen in the presence of the agonist carbachol or the antagonist quinuclidinyl benzylate (QNB). Antigen formats include virus-like particles (VLPs) carrying the rat M3RΔi3 receptor (i.e., the M3 receptor with a deletion in the third intracellular loop), membranes of human CHO cells containing M3R (Perkin Elmer), recombinant reconstituted M3R-T4L, or recombinant reconstituted M3RΔi3. Optionally, VLPs carrying the rat M3RΔi3 receptor or the human M3R membranes were captured by wheat germ agglutinin coated on Maxisorp (Nunc) 96-well plates. Antigen-bound phage was recovered from antigen-coated wells by a trypsin digestion. Alternatively, phage selected on agonist-bound antigen is eluted using an excess of antagonist or vice versa.

After two rounds of bio-panning, 180 colonies were randomly picked and the nanobodies were produced as a soluble His-EPEA-tagged protein in the periplasm of the TG1 cells. A comparative solid-phase ELISA on M3R-T4L receptor versus AT1aR-T4L receptor resulted in 66 M3R-specific nanobodies.

Nanobody Purification for Biochemical Characterization

HIS-tagged or HIS-EPEA-tagged nanobodies were expressed in WK6 *E. coli* cells. Periplasmic extracts were subjected to immobilized metal affinity chromatography on nickel (II) sulfate fast-flow sepharose (GE Healthcare). IMAC protein fractions were dialyzed overnight in 100 mM MES pH 6.5, 100 mM NaCl buffer. Dialyzed nanobodies were further purified by cation exchange chromatography (ÄKTA FPLC with Mono S 10/100 GL column).

Size Exclusion Chromatography

Agonist selective nanobodies were identified by size exclusion chromatography following incubation of 20 μM agonist or inverse agonist- (carazolol-) bound $\beta_2$AR-365N for one hour at RT in the absence or presence of 40 μM nanobody. Chromatography was performed in 0.1% DDM, 20 mM HEPES pH7.5, 100 mM NaCl in the presence of 1 μM of the respective ligands using an ÄKTA FPLC with Superdex 200 10/300 GL column.

Ligand Binding on the Truncated $\beta_2$AR Receptor in Membrane Preparations from Insect Cells Competition binding experiments were performed on $\beta_2$AR-365 expressed in Sf9 insect cell membranes in the absence or presence of 1 μM nanobody for 90 minutes at RT in binding buffer (75 mM Tris pH7.5, 12.5 mM $MgCl_2$, 1 mM EDTA, 0.05% BSA, and 10 μM GTPγS) containing 0.5 nM [$^3$H]-dihydroalprenolol and (−)-isoproterenol at concentrations ranging from $10^{-11}$ M to $10^{-4}$ M. Bound radioligand was separated from unbound over Whatman GF/B filters using a Brandel harvester. The data are the mean±S.E. of two independent experiments performed in triplicate.

Bimane Fluorescence

Purified $\beta_2$AR was reacted with 1:1 equivalent of monobromobimane (mBBr, Invitrogen) in 100 mM NaCl, 20 mM HEPES, pH 7.5, 0.1% dodecyl maltoside and incubated overnight on ice in the dark. The fluorophore-labeled receptor was purified right before use by gel filtration on a desalting column equilibrated with the same buffer. Fluorescence spectroscopy experiments were performed on a Spex FluoroMax-3 spectrofluorometer (Jobin Yvon Inc, NJ) with photon counting mode by using an excitation and emission bandpass of 4 nm. All experiments were performed at 25° C. For emission scans, excitation was set at 370 nm and emission was measured from 430-530 nm with an integration time of 1 s/nm. To determine the effect of nanobodies and ligands, three individual labeled protein samples were incubated with 1 μM nanobody or 10 μM Isoproterenol or both. Emission spectra of the samples were taken after 1 hour incubation. Fluorescence intensity was corrected for background fluorescence from buffer and ligands in all experiments. The data are the mean±S.E. of two independent experiments performed in triplicate.

Preparation of $\beta_2$AR-T4L and Nanobody-80 for Crystallography $\beta_2$AR-T4L was expressed in Sf-9 insect cell cultures infected with $\beta_2$AR-T4L baculovirus, and solubilized according to previously described methods (Kobilka 1995). Functional protein was obtained by M1 FLAG affinity chromatography (Sigma) prior to and following alprenolol-Sepharose chromatography (Kobilka 1995). In the second M1 chromatography step, receptor-bound alprenolol was exchanged for a high affinity agonist and dodecylmaltoside was exchanged for the MNG-3 amphiphile for increased receptor stability (Chae and Gellman, unpublished). The agonist-bound and detergent-exchanged $\beta_2$AR-T4L was eluted in 10 mM HEPES pH 7.5, 100 mM NaCl, 0.02% MNG-3, and 10 μM agonist followed by removal of N-linked glycosylation by treatment with PNGaseF (NEB). The protein was concentrated to ~50 mg/ml with a 100 kDa molecular weight cut off Vivaspin concentrator (Vivascience).

Nanobody-80 (Nb80) bearing a C-terminal His$_6$ tag was expressed in the periplasm of *E. coli* strain WK6 following induction with IPGT. Cultures of 0.6 L were grown to OD$_{600}$=0.7 at 37° C. in TB media containing 0.1% glucose, 2 mM MgCl$_2$, and 50 μg/ml ampicillin. Induced cultures were grown overnight at 28° C. Cells were harvested by centrifugation and lysed in ice-cold buffer (50 mM Tris pH 8.0, 12.5 mM EDTA, and 0.125 M sucrose), then centrifuged to remove cell debris. Nb80 was purified by nickel affinity chromatography, dialyzed against buffer (10 mM HEPES pH 7.5, 100 mM NaCl), and spin concentrated to ~120 mg/ml.

Crystallization

Agonist-bound $\beta_2$AR-T4L and nanobody (e.g., Nb80) were mixed in 1:1.2 molar ratio, incubated two hours at RT before mixing with liquefied monoolein (M7765, Sigma) containing 10% cholesterol (C8667, Sigma) in 1:1.5 protein to lipid ratio (w/w) using the twin-syringe mixing method developed by Martin Caffrey (Caffrey and Cherezov 2009). Initial crystallization leads were identified using in-house screens and optimized in 24-well glass sandwich plates using 50 nL protein:lipid drops manually delivered and overlaid with 0.8 μl precipitant solution in each well and sealed with a glass cover slip. Crystals for data collection were grown at 20° C. by hanging drop vapor diffusion using 0.8 μl reservoir solution (36 to 44% PEG 400, 100 mM Tris pH 8.0, 4% DMSO, 1% 1,2,3-heptanetriol) diluted two- to four-fold in Milli-Q water. Crystals grew to full size within seven to ten days. Crystals were flash frozen and stored in liquid nitrogen with reservoir solution as cryoprotectant.

Microcrystallography Data Collection and Processing

Diffraction data were measured at beamline 23-ID of the Advanced Photon Source, using a 10 μm diameter beam. Low dose 1.0° rotation images were used to locate and center crystals for data collection. Data were measured in 1.0° frames with exposure times typically five to ten seconds with a 5× attenuated beam. Only 5-10° of data could be measured before significant radiation damage occurred. Data were integrated and scaled with the HKL2000 package (Otwinowski 1997).

Structure Solution and Refinement

Molecular replacement phases were obtained with the program Phaser (McCoy 2007). The search models were 1) the high-resolution carazolol-bound $\beta_2$AR structure, PDB id 2RH1, but with T4L and all water, ligand and lipid molecules removed) and a nanobody (PDB id 3DWT, water molecules removed) as search models. The rotation and translation function Z scores were 8.7 and 9.0 after placing the $\beta_2$AR model, and the nanobody model placed subsequently had rotation and translation function Z scores of 3.5 and 11.5. The model was refined in Phenix (Afonine 2005) and Buster (Blanc 2004), using a group B factor model with one B for main chain and one B for side chain atoms. Refinement statistics are given in Table 5. Despite the strong anisotropy (Table 5), the electron density was clear for the placement of side chains.

Ligand Binding on the Truncated $\beta_2$AR Receptor Reconstituted in HDL Particles.

The effect of Nb80 and Gs on the receptors affinity for agonists was compared in competition binding experiments. The $\beta_2$AR and $\beta_2$AR-T4L (both truncated at position 365) purified as previously described (Rosenbaum et al. 2007; Rasmussen et al. 2007) were reconstituted in high-density lipoprotein (HDL) particles followed by reconstitution of Gs into HDL particles containing $\beta_2$AR according to previously published methods (Whorton et al. 2007). 0.6 nM [$^3$H]-dihydroalprenolol ($^3$H-DHA) was used as radioligand and (−)-isoproterenol (ISO) at concentrations ranging from $10^{-12}$ to $10^{-4}$ M as competitor. Nb80 was used at 1 μM. GTPγS was used at 10 μM. TBS (50 mM Tris pH 7.4, 150 mM NaCl) containing 0.1% BSA was used as binding buffer. Bound $^3$H-DHA was separated from unbound on a Brandel harvester by passing over a Whatman GF/B filter (presoaked in TBS with 0.3% polyethylenimine) and washed in cold TBS. Radioligand binding was measured in a Beckman LS6000 scintillation counter. Ligand binding affinity (K$_d$) of DHA was determined from saturation binding curves using GraphPad Prism software. Binding affinities of ISO (K$_i$ values, tabulated in Table 4) were determined from IC$_{50}$ values using the equation K$_i$=IC$_{50}$/(1+[L]/K$_d$).

Ligand Binding on the Full-Length $\beta_2$AR Receptor in Membrane Extracts from Insect Cells for Improved Agonist Identification Competition radioligand binding experiments on membrane extracts were performed essentially as described by Seifert and co-workers (Seifert et al. 1998. *Eur. J. Biochem.* 255:369-382). Ten μg of homogenized membrane extracts from insect cells containing human $\beta_2$AR (Perkin Elmer, cat nr 6110106400UA) were incubated with Nb80 or a non-related Nanobody (negative control; Irr Nb) for one hour at 37° C. in incubation buffer (75 mM Tris-HCl, 12.5 mM $MgCl_2$, 1 mM EDTA and 0.2% w/v BSA) in 24-well plates (Corning Costar). Nanobodies were applied at a final concentration of 500 nM, corresponding to a 3000-fold excess of nanobody versus the adrenergic receptor. Subsequently, an appropriate dilution series of the ligand under investigation was added to the nanobody-bound membrane extracts together with 2 nM of $^3$H-DHA radioligand (Perkin Elmer cat nr NET720001MC; specific activity of 104.4 Ci/mmol). The total volume per well was adjusted with incubation buffer to 500 μl and the reaction mixture was further incubated for another hour at 37° C. in a water bath. After harvesting the membrane extracts with a cell harvester (Inotech) onto glass fiber filters (Whatmann GF/B filter paper), filters were washed with ice cold wash buffer (50 mM Tris-HCl pH 7.4) and air dried filters parts were transferred to scintillation tubes containing 3.5 ml of Optiphase "Hisafe 2" scintillation liquid (Perkin Elmer). Radioactivity was measured in a LKB Wallace scintillation counter after one hour incubation at room temperature.

Compound Library Screening

A compound library was screened for agonists using a competition radioligand binding assay. For this purpose, 10 μg of in house prepared membrane extracts from HEK293T cells expressing human $β_2$AR (expression level of ~10 pmol/mg membrane protein) are pre-incubated with Nb80 or a non-related Nanobody (negative control) for one hour at 30° C. in incubation buffer (50 mM Hepes pH 7.4, 1 mM $CaCl_2$, 5 mM $MgCl_2$, 100 mM NaCl and 0.5% w/v BSA). Nanobodies are applied at a final concentration of 500 nM, roughly corresponding to a 3000-fold excess of Nanobody versus the $β_2$AR. Subsequently, the Nanobody-loaded membranes are added to 96-well plates containing library compounds and 2 nM of $^3$H-dihydroalprenolol (DHA) radioligand. The total volume per well is adjusted with incubation buffer to 100 μl and the reaction mixture is further incubated for another hour at 30° C. Subsequently, membrane-bound radioligand is harvested using a GF/B glass fiber 96-well filterplate (Perkin Elmer) presoaked in 0.3% polyethylenimine. Filter plates are washed with ice-cold wash buffer (50 mM Tris-HCl pH7.4), and dried for 30 minutes at 50° C. After adding 25 μl of scintillation fluid (MicroScint™-O, Perkin Elmer), radioactivity (cpm) is measured in a Wallace MicroBeta TriLux scintillation counter.

Bimane Fluorescence Spectroscopy on $β_2$AR Reconstituted in HDL Particles

To compare the effects on receptor conformation of Gs and Nb80 binding the purified $β_2$AR was labeled with the environmentally sensitive fluorescent probe monobromobimane (Invitrogen) at cysteine 265 located in the cytoplasmic end of TM6, and reconstituted into HDL particles (mBB-$β_2$AR/HDL). Prior to obtaining fluorescence emission spectra 10 nM mBB-$β_2$AR/HDL incubated 30 minutes at RT in buffer (20 mM HEPES pH 7.5, 100 mM NaCl) in the absence or presence of 10 μM ISO, 1 μM inverse agonist ICI-118,551 (ICI), 300 nM Gs heterotrimer, or 300 nM Nb80, or in combinations of ISO with Gs, ISO with Nb80, and ICI with Nb80. Fluorescence spectroscopy was performed on a Spex FluoroMax-3 spectrofluorometer (Jobin Yvon Inc.) with photon-counting mode, using an excitation and emission bandpass of 5 nm. Excitation was set at 370 nm and emission was collected from 415 to 535 nm in 1 nm increments with 0.3 sec/nm integration time. Fluorescence intensity was corrected for background fluorescence from buffer and ligands.

TABLE 1

List of $β_2$AR-specific nanobodies

| Nanobody reference number | Nanobody short notation | SEQ ID NO: |
|---|---|---|
| CA2764 | NB64 | 1 |
| CA3431 | NB31 | 2 |
| CA3413 | NB13 | 3 |
| CA2780 | NB80 | 4 |
| CA2765 | NB65 | 5 |
| CA2761 | NB61 | 6 |
| CA3475 | NB75 | 7 |
| CA2770 | NB70 | 8 |
| CA3472 | NB72 | 9 |
| CA3420 | NB20 | 10 |
| CA3433 | NB33 | 11 |
| CA3434 | NB34 | 12 |
| CA3484 | NB84 | 13 |
| CA2760 | NB60 | 14 |
| CA2773 | NB73 | 15 |
| CA3477 | NB77 | 16 |
| CA2774 | NB74 | 17 |
| CA2768 | NB68 | 18 |
| CA3424 | NB24 | 19 |
| CA2767 | NB67 | 20 |
| CA2786 | NB86 | 21 |
| CA3422 | NB22 | 22 |
| CA2763 | NB63 | 23 |
| CA2772 | NB72 | 24 |
| CA2771 | NB71 | 25 |
| CA2769 | NB69 | 26 |
| CA2782 | NB82 | 27 |
| CA2783 | NB83 | 28 |
| CA2784 | NB84 | 29 |

TABLE 2

CDRs of $β_2$AR-specific nanobodies

| Nanobody reference number | Nanobody short notation | CDR1 | CDR2 | CDR3 |
|---|---|---|---|---|
| CA2764 | NB64 | GSIFSINT (SEQ ID NO: 30) | IHSGGST (SEQ ID NO: 43) | NVKDYGAVLYEYDY (SEQ ID NO: 57) |
| CA3431 | NB31 | GSIFSINT (SEQ ID NO: 30) | IHSGGST (SEQ ID NO: 43) | NVKDYGAVLYEYDY (SEQ ID NO: 57) |
| CA3413 | NB13 | GSIFSINT (SEQ ID NO: 30) | IHSGGST (SEQ ID NO: 43) | NVKDYGAVLYEYDY (SEQ ID NO: 57) |
| CA2780 | NB80 | GSIFSINT (SEQ ID NO: 30) | IHSGGST (SEQ ID NO: 43) | NVKDYGAVLYEYDY (SEQ ID NO: 57) |

TABLE 2-continued

CDRs of β₂AR-specific nanobodies

| Nanobody reference number | Nanobody short notation | CDR1 | CDR2 | CDR3 |
|---|---|---|---|---|
| CA2765 | NB65 | GSIFSINT (SEQ ID NO: 30) | IHSGGST (SEQ ID NO: 43) | NVKDYGAVLYEYDY (SEQ ID NO: 57) |
| CA2761 | NB61 | GSIFSLND (SEQ ID NO: 31) | ITSGGST (SEQ ID NO: 44) | NAVVAGTFSTYDY (SEQ ID NO: 58) |
| CA3475 | NB75 | GSIFSLND (SEQ ID NO: 31) | ITSGGST (SEQ ID NO: 44) | NAVVAGTFSTYDY (SEQ ID NO: 58) |
| CA2770 | NB70 | GSIFSLND (SEQ ID NO: 31) | ISSGGRL (SEQ ID NO: 45) | NAVVAGTFSTYDY (SEQ ID NO: 58) |
| CA3472 | NB72 | GSIFSLND (SEQ ID NO: 31) | ISSGGRL (SEQ ID NO: 45) | NAVVAGTFSTYDY (SEQ ID NO: 58) |
| CA3420 | NB20 | GSIFSLND (SEQ ID NO: 31) | ITSGGST (SEQ ID NO: 44) | NAKVAGTFSIYDY (SEQ ID NO: 59) |
| CA3433 | NB33 | GSIFSLND (SEQ ID NO: 31) | VTSGGST (SEQ ID NO: 46) | NAKVAGTFSIYDY (SEQ ID NO: 59) |
| CA3434 | NB34 | GSIFSLND (SEQ ID NO: 31) | ITSGGST (SEQ ID NO: 44) | NAKVAGTFSIYDY (SEQ ID NO: 59) |
| CA3484 | NB84 | GSIFSLND (SEQ ID NO: 31) | ITSGGST (SEQ ID NO: 44) | NAKVAGTFSIYDY (SEQ ID NO: 59) |
| CA2760 | NB60 | GSIFSLND (SEQ ID NO: 31) | ITSGGST (SEQ ID NO: 44) | NAKVAGTFSIYDY (SEQ ID NO: 59) |
| CA2773 | NB73 | GSIFSLND (SEQ ID NO: 31) | ITSGRST (SEQ ID NO: 47) | NAKVAGTFSIYDY (SEQ ID NO: 59) |
| CA3477 | NB77 | GSIFSLND (SEQ ID NO: 31) | ITSGGST (SEQ ID NO: 44) | NAKVAGTFSIYDY (SEQ ID NO: 59) |
| CA2774 | NB74 | GSIFSIND (SEQ ID NO: 32) | ITSGGSV (SEQ ID NO: 48) | NAKVAGTFSIYDY (SEQ ID NO: 59) |
| CA2768 | NB68 | GTIFSNNA (SEQ ID NO: 33) | ITSGGST (SEQ ID NO: 44) | NAKVPGTFSIYDY (SEQ ID NO: 60) |
| CA3424 | NB24 | GSVFSLPT (SEQ ID NO: 34) | ITGSGST (SEQ ID NO: 49) | YYRSTFTEY (SEQ ID NO: 61) |
| CA2767 | NB67 | GTISSFIA (SEQ ID NO: 35) | ITSGGET (SEQ ID NO: 50) | NAQVFADIFNLINY (SEQ ID NO: 62) |
| CA2786 | NB86 | GTIFSPNT (SEQ ID NO: 36) | ITSGGSR (SEQ ID NO: 51) | NYQTVFFGNAEA (SEQ ID NO: 63) |
| CA3422 | NB22 | GSIFSINA (SEQ ID NO: 37) | STSGDIT (SEQ ID NO: 52) | NARGIYSDYAFADFNS (SEQ ID NO: 64) |
| CA2763 | NB63 | GSRFSFIT (SEQ ID NO: 38) | LSGDNT (SEQ ID NO: 53) | RGTSVLYDV (SEQ ID NO: 65) |
| CA2772 | NB72 | GFTFSGYA (SEQ ID NO: 39) | INSGGGST (SEQ ID NO: 54) | HARDIYSDFLGQYEYDY (SEQ ID NO: 66) |
| CA2771 | NB71 | GFAFSSYE (SEQ ID NO: 40) | ITTGGNT (SEQ ID NO: 55) | NANWDLLSDY (SEQ ID NO: 67) |
| CA2769 | NB69 | GSIFSINA (SEQ ID NO: 37) | ITSGGST (SEQ ID NO: 44) | NVQGTGPSSWLFNEYDY (SEQ ID NO: 68) |
| CA2782 | NB82 | GSIFSINS (SEQ ID NO: 41) | ITSDGST (SEQ ID NO: 56) | NADSVYSDFLGKYEYDY (SEQ ID NO: 69) |

TABLE 2-continued

CDRs of β₂AR-specific nanobodies

| Nanobody reference number | Nanobody short notation | CDR1 | CDR2 | CDR3 |
|---|---|---|---|---|
| CA2783 | NB83 | GSIFSLNA (SEQ ID NO: 42) | ITSDGST (SEQ ID NO: 56) | NADSVYSDFLGKYEYDY (SEQ ID NO: 69) |
| CA2784 | NB84 | GSIFSINA (SEQ ID NO: 37) | ITSGGST (SEQ ID NO: 44) | HVRDIYSDFLGQYEYDY (SEQ ID NO: 70) |

TABLE 3. Full Agonist Binding Properties of Membranes Expressing $\beta_2AR$ in the Presence and Absence of Nanobodies.

[3H]-DHA Competition binding was performed on Sf9 insect cell membranes expressing $\beta_2AR$, in the presence or absence of 1 μM nanobodies. Data represent the mean±s.e. of two independent experiments performed in triplicate. The IC50 values used for calculations of Ki values were obtained from means of pIC50 values determined by nonlinear regression analysis using Prism (GraphPad Software, San Diego, Calif.) and the s.e. interval from pIC50±s.e.

|  | Isoproterenol Ki [S.E. interval] (nm) |
|---|---|
| $\beta_2AR$ | 295 [211-412] |
| +NB65 | 13.8 [6.98-27.3] |
| +NB67 | 19.4 [11.3-33.1] |
| +NB69 | 53.5 [34.3-83.1] |
| +NB71 | 10.6 [3.68-30.4] |
| +NB72 | 145 [93.3-226] |
| +NB80 | 10.0 [4.74-21.0] |
| +NB84 | 75.4 [35.9-158] |

TABLE 4

Pharmacological characterization of $\beta_2AR$ reconstituted in HDL particles in complex with Gs and Nb80

|  | [³H]-DHA saturation binding $K_d$ ± S.E. nM | [³H]-DHA/(-)-isoproterenol competition binding | | |
|---|---|---|---|---|
|  |  | Low affinity state $K_i$ [S.E. interval] nM | High affinity state $K_i$ [S.E. interval] nM |  |
| $\beta_2AR$ | 0.55 ± 0.09 (n = 3) | 107.5 [103.8-111.3] |  | (n = 3) |
| $\beta_2AR$ + Gs |  | 95.3 [82.8-109.7] | 1.07 [0.96-1.19] | (n = 4) |
| $\beta_2AR$ + Gs + GTPγS |  | 95.2 [92.2-98.3] |  | (n = 3) |
| $\beta_2AR$ + NB80 |  |  | 1.13 [1.09-1.18] | (n = 3) |
| $\beta_2AR$-T4L | 0.42 ± 0.01 (n = 3) | 33.5 [31.6-35.5] |  | (n = 3) |
| $\beta_2AR$-T4L + NB80 |  |  | 0.56 [0.54-0.57] | (n = 4) |

TABLE 5

X-ray data collection and refinement statistics of the $\beta_2AR$-Nb80 complex

| A. Data collection statistics | |
|---|---|
| wavelength (Å) | 1.0332 |
| space group | C2 |
| unit cell parameters | |
| a (Å) | 236.7 |
| b (Å) | 45.7 |
| c (Å) | 71.4 |
| β (°) | 102.3 |
| number of crystals | 23 |
| resolution (Å) | 37-3.50 (3.56-3.50) |
| unique reflections | 10147 (903) |
| completeness | 94.8 (93.7) |
| multiplicity | 3.5 (3.2) |
| <I/σ(I)> | 6.7 (1.8) |
| $R_{merge}$ (%) | 0.192 (0.594) |
| B. refinement statistics | |
| resolution (Å) | 37-3.50 |
| No. of reflections working set (test set) | 9210 (937) |
| $R_{work}/R_{free}$ (%) | 0.225/0.294 |
| rmsd from ideality | |
| bond lengths (Å) | 0.010 |
| bond angles (°) | 1.3 |
| Anisotropic B correction (Å²) | $B_{11}$ = 33.5/$B_{22}$ = 2.7/ $B_{33}$ = −36.3/$B_{13}$ = 4.5 |
| Average B factor (Å²) | |
| receptor | 76.4 |
| nanobody | 96.6 |
| agonist | 62.4 |
| Ramachandran analysis | |
| residues in most-favored region (%) | 86.6 |
| additionally allowed region (%) | 13.4 |
| generously allowed region (%) | 0.0 |
| disallowed region (%) | 0.0 |

TABLE 6

Nanobody 80 induced potency shift of (ant-)agonists. Agonists show an increased affinity for the $\beta_2$AR-Nb80 complex.

| Competitor ID | Type competitor for $\beta_2$AR | Potency shift* |
| --- | --- | --- |
| isoproterenol | agonist | 8.8 |
| alprenolol | antagonist | 1.1 |
| carvedilol | antagonist | 1.2 |
| CGP12177A | antagonist | 1.0 |
| salmeterol | full agonist | 3.3 |
| terbutaline | partial agonist | 4.3 |
| dobutamine | partial agonist | 2.3 |
| salbutamol | partial agonist | 4.2 |
| ICI118,551 | Inverse agonist | 0.9 |
| metaproterenol | agonist | 2.9 |
| procaterol | agonist | 2.3 |
| ritodrine | agonist | 2.7 |
| fenoterol | Full agonist | 3.7 |
| formoterol | agonist | 4.0 |
| timolol | antagonist | 0.6 |

*Potency shifts were determined as the ratio of the IC50 measured in the presence of an irrelevant Nb (negative control) and the IC50 measured in the presence of Nb80.

REFERENCES

Afonine P. V., R. W. Grosse-Kunstleve, and P. D. Adams (2005). A robust bulk-solvent correction and anisotropic scaling procedure. Acta crystallographica. Section D, Biological crystallography, 61:850-5.

Ahuja S. and S. O. Smith. Multiple switches in G protein-coupled receptor activation. Trends Pharmacol. Sci. 30:494-502, doi:S0165-6147(09)00124-2 [pii] 10.1016/j.tips.2009.06.003 (2009).

Alexandrov A. I., M. Mileni, et al. (2008). Microscale Fluorescent Thermal Stability Assay for Membrane Proteins. Structure 16:351-359.

Altenbach C., A. K. Kusnetzow, O. P. Ernst, K. P. Hofmann, and W. L. Hubbell. High-resolution distance mapping in rhodopsin reveals the pattern of helix movement due to activation. Proc. Natl. Acad. Sci. U.S.A. 105:7439-7444, doi:0802515105 [pii] 10.1073/pnas.0802515105 (2008).

Ballesteros J. A. and H. Weinstein. Integrated methods for the construction of three-dimensional models and computational probing of structure-function relations in G-protein-coupled receptors. Meth. Neurosci. 25:366-428 (1995).

Ballesteros J. A. et al. Activation of the $\beta_2$-adrenergic receptor involves disruption of an ionic lock between the cytoplasmic ends of transmembrane segments 3 and 6. J. Biol. Chem. 276:29171-29177. (2001).

Blanc E., P. Roversi, C. Vonrhein, C. Flensburg, S. M. Lea, G. Bricogne, et al. (2004). Refinement of severely incomplete structures with maximum likelihood in BUSTER-TNT. Acta crystallographica. Section D, Biological crystallography, 60:2210-21.

Binz et al. Nature Biotech. 22:575-582 (2004).

Bokoch M. P. et al. Ligand-specific regulation of the extracellular surface of a G-protein-coupled receptor. Nature 463:108-112, doi:nature08650 [pii] 10.1038/nature08650 (2010).

Caffrey (2003). Membrane protein crystallization. J. Struct. Biol. 2003 142:108-32.

Caffrey M. and V. Cherezov. Crystallizing membrane proteins using lipidic mesophases. Nat. Protoc. 4:706-731, doi:nprot.2009.31 [pii] 10.1038/nprot.2009.31 (2009).

Chelikani et al. Protein Sci. 2006 15:1433-40.

Cherezov V. et al. High-resolution crystal structure of an engineered human $\beta_2$-adrenergic G protein-coupled receptor. Science 318:1258-1265, doi:1150577 [pii] 10.1126/science.1150577 (2007).

Chini B., and M. Parenti (2009). G-protein-coupled receptors, cholesterol and palmitoylation: facts about fats. Journal of Molecular Endocrinology 42(5):371-9.

Chomczynski P. and N. Sacchi (1987). Single-step method of RNA isolation by acid guanidium thiocyanate-phenol-chloroform extraction. Anal. Biochem. 162, p. 156.

Conrath K. E., M. Lauwereys, M. Galleni et al. Antimicrob. Agents Chemother. 45 (10):2807 (2001).

Conrath K., A. S. Pereira, C. E. Martins, C. G. Timóteo, P. Tavares, S. Spinelli, J. Kinne, C. Flaudrops, C. Cambillau, S. Muyldermans, I. Moura, J. J. Moura, M. Tegoni, and A. Desmyter. Camelid nanobodies raised against an integral membrane enzyme, nitric oxide reductase. Protein Sci. 2009 March, 18(3):619-28.

Cooper M. A. (2004). J. Mol. Recognit. 17:286-315.

Day P. W., S. G. Rasmussen, C. Parnot, J. J. Fung, A. Masood, T. S. Kobilka, X. J. Yao, H. J. Choi, W. I. Weis and D. K. Rohrer, et al. A monoclonal antibody for G protein-coupled receptor crystallography. Nat. Methods 4 (2007), pp. 927-929.

De Genst et al. (2010). J. Mol. Biol. 402:326-343.

Delean A., J. M. Stadel, et al. (1980). "A ternary complex model explains the agonist-specific binding properties of the adenylate cyclase-coupled beta-adrenergic receptor." J. Biol. Chem. 255(15):7108-7117.

Derewenda Z. S. Rational protein crystallization by mutational surface engineering, Structure (Camb) 12 (2004), pp. 529-535.

Dimitrov D. S. Engineered CH2 domains (nanoantibodies). Mabs. 2009 January-February; 1(1):26-8.

Eroglu et al. EMBO (2002) 3:491-96.

Eroglu et al. Proc. Natl. Acad. Sci. (2003) 100:10219-10224.

Faham et al. Crystallization of bacteriorhodopsin from bicelle formulations at room temperature. Protein Sci. (2005) 14:836-40.

Faham et al. Bicelle crystallization: a new method for crystallizing membrane proteins yields a monomeric bacteriorhodopsin structure. J. Mol. Biol. (2002) Feb. 8, 316(1):1-6.

Fredriksson R., M. C. Lagerstrom, et al. (2003). "The G-protein-coupled receptors in the human genome form five main families. Phylogenetic analysis, paralogon groups, and fingerprints." Molecular Pharmacology 63(6): 1256-1272.

Gebauer M., and A. Skerra. Engineered protein scaffolds as next-generation antibody therapeutics. Curr. Opin. Chem. Biol. (2009) June, 13(3):245-55.

George et al. Nat. Rev. Drug Discov. 1:808-820 (2002).

Ghanouni et al. 2000.

Ghanouni P. et al. Functionally different agonists induce distinct conformations in the G protein coupling domain of the $\beta_2$-adrenergic receptor. J. Biol. Chem. 276:24433-24436. (2001).

Gouaux, It's not just a phase: crystallization and X-ray structure determination of bacteriorhodopsin in lipidic cubic phases. Structure 1998 6:5-10.

Hamers-Casterman C., T. Atarhouch, S. Muyldermans et al. Naturally occurring antibodies devoid of light chains. Nature 363:446-448, doi:10.1038/363446a0 (1993).

Hanson M. A. et al. A specific cholesterol binding site is established by the 2.8 angstrom structure of the human $\beta_2$-adrenergic receptor. Structure 16:897-905 (2008).

Heilker et al. Drug Discovery Today (2009) 14:231-240.

Hendrickson W A. Determination of macromolecular structures from anomalous diffraction of synchrotron radiation. *Science* (1991) Oct. 4, 254(5028):51-8.

Hofmann K. P., P. Scheerer, P. W. Hildebrand, et al. *Trends Biochem. Sci.* 34(11):540 (2009).

Hunte C. and H. Michel H. Crystallization of membrane proteins mediated by antibody fragments. *Curr. Opin. Struct. Biol.* 12 (2002), pp. 503-508.

Jaakola V. P., et al. The 2.6 Angstrom Crystal Structure of a Human A2A Adenosine Receptor Bound to an Antagonist. *Science* (2008).

Kallwass et al. *Biotechnol. Lett.* (1993) 15 (1):29-34.

Kenakin. *Trends Pharmacol. Sci.* 25:186-192 (2002).

Kobilka B. K. and X. Deupi. *Trends in Pharmacological Sciences* 28(8):397 (2007).

Kobilka B. K. Amino and carboxyl terminal modifications to facilitate the production and purification of a G protein-coupled receptor. *Anal. Biochem.* 231:269-271 (1995).

Koide et al. *J. Mol. Biol.* (1998) 284:1141-1151.

Koide S. (2009). Engineering of recombinant crystallization chaperones. *Current Opinion in Structural Biology* 19:449.

Krissinel E. and K. Henrick (2007). Inference of macromolecular assemblies from crystalline state. *J. Mol. Biol.* 372:774-797.

Landau et al. Lipidic cubic phases: a novel concept for the crystallization of membrane proteins. *Proc. Natl. Acad. Sci.* 1996 93:14532-5.

Lee A. G. (2004). How lipids affect the activities of integral membrane proteins. *Biochimica et biophysica acta* 1666 (1-2):62-87.

Lefranc M. P., E. Duprat, Q. Kaas, M. Tranne, A. Thiriot, and G. Lefranc. IMGT unique numbering for MHC groove G-DOMAIN and MHC superfamily (MhcSF) G-LIKE-DOMAIN. *Dev. Comp. Immunol.* (2005) 29(11): 917-38.

Lefranc M. P., C. Pommie, et al. (2003). "IMGT unique numbering for immunoglobulin and T cell receptor variable domains and Ig superfamily V-like domains." *Developmental and Comparative Immunology* 27(1):55-77.

Li H., J. J. Dunn, B. J. Luft and C. L. Lawson. Crystal structure of Lyme disease antigen outer surface protein A complexed with a Fab. *Proc. Natl. Acad. Sci. U.S.A.* 94 (1997), pp. 3584-3589.

Li J., P. C. Edwards, M. Burghammer, C. Villa, and G. F. Schertler. Structure of bovine rhodopsin in a trigonal crystal form. *J. Mol. Biol.* 343:1409-1438 (2004).

Liapakis G. et al. The forgotten serine. A critical role for Ser-2035.42 in ligans binding to and activation of the $\beta_2$-adrenergic receptor. *J. Biol. Chem.* 275:37779-37788. (2000).

Luca et al. *Proc. Natl. Acad. Sci.* (2003) 100:10706-11.

Lynch Kevin R. (Ed). *Identification and Expression of G-Protein-Coupled Receptors* published by John Wiley & Sons (March 1998).

McCoy A. J., R. W. Grosse-Kunstleve, P. D. Adams, M. D. Winn, L. C. Storoni, R. J. Read, et al. (2007). Phaser crystallographic software. *Journal of applied crystallography*, 40(Pt 4), 658-674.

Magnani F., Y. Shibata, et al. (2008). Co-evolving stability and conformational homogeneity of the human adenosine A2a receptor. *Proc. Natl. Acad. Sci. U.S.A.* 105(31): 10744-10749.

Mansoor et al. *Proc. Natl. Acad. Sci.* (2006) 103:3060-3065.

Marchese et al. *Genomics* (1994) 23:609-618.

Nakamichi H. and T. Okada. Local peptide movement in the photoreaction intermediate of rhodopsin. *Proc. Natl. Acad. Sci. U.S.A.* 103:12729-12734, doi:0601765103 [pii] 10.1073/pnas.0601765103 (2006).

Neubig R. R., M. Spedding, et al. (2003). "International Union of Pharmacology Committee on Receptor Nomenclature and Drug Classification. XXXVIII. Update on terms and symbols in quantitative pharmacology." *Pharmacological Reviews* 55(4):597-606.

Niu et al. *Biophys. J.* (2005) 89:1833-1840.

Nollert et al. Lipidic cubic phases as matrices for membrane protein crystallization. *Methods* 2004 34:348-53.

Nygren P-A. (2008) Alternative binding proteins: affibody binding proteins developed from a small three-helix bundle scaffold. *FEBS J.* 275:2668-2676.

Ostermeier C., S. Iwata, B. Ludwig and H. Michel. Fv fragment-mediated crystallization of the membrane protein bacterial cytochrome c oxidase. *Nat. Struct. Biol.* 2 (1995), pp. 842-846.

Otwinowski Z. and W. Minor (1997). Processing of X-ray diffraction data collected in oscillation mode. *Methods in Enzymology* 276:307-325.

Palczewski K. et al. Crystal structure of rhodopsin: A G protein-coupled receptor [see comments]. *Science* 289: 739-745 (2000).

Park J. H., P. Scheerer, K. P. Hofmann, H. W. Choe, and O. P. Ernst. Crystal structure of the ligand-free G-protein-coupled receptor opsin. *Nature* 454:183-U133 (2008).

Parnot C., S. Miserey-Lenkei, S. Bardin, P. Corvol, and E. Clauser. Lessons from constitutively active mutants of G protein-coupled receptors. *Trends Endocrinol. Metab.* 13:336-343 (2002).

Pellissier L. P. et al. Conformational toggle switches implicated in basal constitutive and agonist-induced activated states of 5-hydroxytryptamine-4 receptors. *Mol. Pharmacol.* 75:982-990, doi:mol.108.053686 [pii] 10.1124/mol.108.053686 (2009).

Probst et al. (1992). *DNA Cell Biol.* 11:1-20.

Qian Z. M., H. Li, H. Sun and K. Ho (2002). Targeted drug delivery via the transferring receptor-mediated endocytosis pathway. *Pharmacol. Rev.* 54:561-587.

Rasmussen S. G., H. J. Choi, D. M. Rosenbaum, T. S. Kobilka, F. S. Thian, P. C. Edwards, M. Burghammer, V. R. Ratnala, R. Sanishvili and R. F. Fischetti et al. Crystal structure of the human $\beta_2$-adrenergic G-protein-coupled receptor. *Nature* 450 (2007), pp. 383-387.

Rios et al. *Pharmacol. Ther.* 92:71-87 (2001)).

Ritter S. L. and R. A. Hall (2009). Fine-tuning of GPCR activity by receptor-interacting proteins. Nature reviews. *Molecular Cell Biology* 10(12):819-30, Nature Publishing Group. doi: 10.1038/nrm2803).

Rosenbaum D. M., S. G. Rasmussen, and B. K. Kobilka. *Nature* 459 (7245):356 (2009).

Rosenbaum D. M., V. Cherezov, M. A. Hanson et al. *Science* 318 (5854):1266 (2007).

Rummel et al. *Lipidic Cubic Phases: New Matrices for the Three-Dimensional Crystallization of Membrane Proteins. J. Struct. Biol.* (1998) 121:82-91.

Sawant R. and V. Torchilin. Intracellular transduction using cell-penetrating peptides. *Mol. Biosyst.* (2010) April, 6(4): 628-40. Epub 2009 Dec. 21.

Scheerer P. et al. Crystal structure of opsin in its G-protein-interacting conformation. *Nature* 455:497-502 (2008).

Schertler G. F. Structure of rhodopsin and the metarhodopsin I photointermediate. *Curr. Opin.* Struct. Biol. 15:408-415 (2005).

Shi L. et al. $\beta_2$-adrenergic receptor activation. Modulation of the proline kink in transmembrane 6 by a rotamer toggle switch. *J. Biol. Chem.* 277:40989-40996 (2002).

Shimada et al. *J. Biol. Chem.* (2002) 277:31774-80.

Shukla A. K., C. Reinhart, and H. Michel H. (2006). Comparative analysis of the human angiotensin II type 1a receptor heterologously produced in insect cells and mammalian cells. *Biochem. Biophys. Res. Commun.* Oct. 13; 349(1):6-14.

Skerra *J. Molecular Recognition* 13:167-187 (2000).

Stanley A. M. and K. G. Fleming. Process of folding proteins into membranes: Challenges and progress. *Archives of Biochemistry and Biophysics* 469(1):46-66 (2008).

Starovasnik M. A., A. C. Braisted, and J. A. Wells. Structural mimicry of a native protein by a minimized binding domain. *Proc. Natl. Acad. Sci. U.S.A.* 1997 Sep. 16; 94(19):10080-5.

Steve Watson (Ed). *G-Protein Linked Receptor Factsbook*, published by Academic Press (1st edition; 1994).

Strader C. D. et al. Identification of residues required for ligand binding to the β-adrenergic receptor. *Proc. Natl. Acad. Sci. U.S.A.* 84:4384-4388 (1987).

Tatsuya Haga (Ed). *G Protein-Coupled Receptors*, published by CRC Press (Sep. 24, 1999).

Vasudevan S., E. C. Hulmez, M. Bach, W. Haase, J. Pavia, and H. Reilander (1995). *Eur. J. Biochem.* 227:466-475.

Warne T. et al. Structure of a β$_1$-adrenergic G-protein-coupled receptor. *Nature* 454:486-491, doi:nature07101 [pii] 10.1038/nature07101 (2008).

Wesolowski J., V. Alzogaray, J. Reyelt, M. Unger, K. Juarez, M. Urrutia, A. Cauerhiff, W. Danquah, B. Rissiek, F. Scheuplin, N. Schwarz, S. Adriouch, O. Boyer, M. Seman, A. Licea, D. V. Serreze, F. A. Goldbaum, F. Haag, and F. Koch-Nolte (2009). Single domain antibodies: promising experimental and therapeutic tools in infection and immunity. *Med. Microbiol. Immunol.* 198:157-174.

Wess Jurgen (Ed). *Structure-Function Analysis of G Protein-Coupled Receptors* published by Wiley-Liss (1 st edition; Oct. 15, 1999).

Whorton M. R. et al. A monomeric G protein-coupled receptor isolated in a high-density lipoprotein particle efficiently activates its G protein. *Proc. Natl. Acad. Sci. U.S.A.* 104:7682-7687, doi:0611448104 [pii] 10.1073/pnas.0611448104 (2007).

Wieland K., H. M. Zuurmond, C. Krasel, A. P. Ijzerman, and M. J. Lohse. Involvement of Asn-293 in stereospecific agonist recognition and in activation of the β$_2$-adrenergic receptor. *Proc. Natl. Acad. Sci. U.S.A.* 93:9276-9281 (1996).

Yao X. J. et al. The effect of ligand efficacy on the formation and stability of a GPCR-G protein complex. *Proc. Natl. Acad. Sci. U.S.A.* 106:9501-9506, doi:0811437106 [pii] 10.1073/pnas.0811437106 (2009).

Yoshikawa T., T. Sugita, Y. Mukai, Y. Abe, S. Nakagawa, H. Kamada, S. Tsunoda, and Y. Tsutsumi. The augmentation of intracellular delivery of peptide therapeutics by artificial protein transduction domains. *Biomaterials* 2009 July; 30(19):3318-23.

Violin J. D., S. M. DeWire, D. Yamashita, D. H. Rominger, L. Nguyen, K. Schiller, E. J. Whalen, M. Gowen, and M. W. Lark (2010). *J. Pharmacol. Exp. Ther.* 335(3):572-9.

Zhang X. J., J. A. Wozniak, and B. W. Matthews. Protein flexibility and adaptability seen in 25 crystal forms of T4 lysozyme. *J. Mol. Biol.* 250:527-552, doi:S0022-2836 (85)70396-8 [pii] 10.1006/jmbi.1995.0396 (1995).

Zhou Y. and J. U. Bowie (2000). Building a thermostable membrane protein. *J. Biol. Chem.* 275:6975-6979.

What is claimed is:

1. A polypeptide comprising an amino acid sequence that consists of 4 framework regions (FR1 to FR4, respectively) and 3 complementary determining regions (CDR1 to CDR3, respectively) according to the formula: FR1-CDR1-FR2-CDR2-FR3-CDR3-FR4, wherein CDR1 is the amino acid sequence of SEQ ID NO:31 or an amino acid sequence that has at least 80% identity with SEQ ID NO:31, wherein CDR2 is the amino acid sequence of SEQ ID NO:44 or an amino acid sequence that has at least 80% identity with SEQ ID NO:44 and wherein CDR3 is the amino acid sequence of SEQ ID NO:59 or an amino acid sequence that has at least 80% identity with SEQ ID NO:59, wherein said polypeptide has binding activity for human $\beta_2$ adrenergic receptor.

2. The polypeptide according to claim 1 comprising an amino acid sequence that has at least 80% identity with an amino acid sequence selected from the group consisting of SEQ ID NO: 14, SEQ ID NO:6, SEQ ID NO:7, SEQ ID NO:8, SEQ ID NO: 10, SEQ ID NO:11, SEQ ID NO:12, SEQ ID NO:13, SEQ ID NO: 15, SEQ ID NO:16 and SEQ ID NO:17.

3. A composition comprising the polypeptide according to claim 1.

4. A composition comprising the polypeptide according to claim 2.

* * * * *